(12) United States Patent
Torday et al.

(10) Patent No.: US 6,992,093 B2
(45) Date of Patent: Jan. 31, 2006

(54) METHOD OF INHIBITING LIPOFIBROBLAST TO MYOFIBROBLAST TRANSDIFFERENTIATION

(75) Inventors: John S. Torday, Redondo Beach, CA (US); Virender K. Rehan, Torrance, CA (US)

(73) Assignee: Los Angeles Biomedical Research Institute at Harbor UCLA Medical Center, Torrance, CA (US)

( * ) Notice: Subject to any disclaimer, the term of this patent is extended or adjusted under 35 U.S.C. 154(b) by 290 days.

(21) Appl. No.: 10/352,768

(22) Filed: Jan. 27, 2003

(65) Prior Publication Data

US 2004/0072875 A1 Apr. 15, 2004

Related U.S. Application Data

(60) Provisional application No. 60/377,665, filed on May 2, 2002, and provisional application No. 60/421,615, filed on Oct. 25, 2002.

(51) Int. Cl.
*A61K 31/4402* (2006.01)
*A61K 31/427* (2006.01)
*A61K 31/5578* (2006.01)

(52) U.S. Cl. .................. 514/342; 514/369; 514/374; 514/462; 514/568; 514/573; 514/619; 514/635

(58) Field of Classification Search ............... 514/342, 514/369, 374, 462, 568, 573, 619, 635
See application file for complete search history.

(56) References Cited

U.S. PATENT DOCUMENTS

| 5,235,033 A | 8/1993 | Summerton et al. |
| 6,028,088 A | 2/2000 | Pershadsingh et al. |

FOREIGN PATENT DOCUMENTS

| WO | WO 00/53601 | 9/2000 |
| WO | WO 00/62766 | 10/2000 |
| WO | WO 01/82868 A2 | 11/2001 |
| WO | WO 01/82980 A1 | 11/2001 |

OTHER PUBLICATIONS

Rehan et al., FASEB Journal, (Mar. 22, 2002) vol. 16, No. 5, pp. A1151.*
Demayo et al. (2002) "Mesenchymal-epithelial interaction in lung development and repair: are modeling and remodeling the same process" AJP Lung Cellular and Molecular Physiology vol. 283: Issue 3: pp. 510–517.
Torday et al. (2003) "Mechanotransduction determines the structure and function of lung and bone" Cell Biochemistry and Biophysics, vol. 37, pp. 235–246.
Torday et al. (2003) "The role of fibroblast transdifferentiation in lung epithelial cell proliferation, differentiation and in vitro" Ped, Pathol Mol Med vol. 3, pp. 189–207.

* cited by examiner

*Primary Examiner*—Phyllis G. Spivack
(74) *Attorney, Agent, or Firm*—Quine I. P. Law Group, P.C.; Tom Hunter

(57) ABSTRACT

Methods of inhibiting lipofibroblast to myofibroblast transdifferentiation in a mammal are disclosed comprising administering a PPAR gamma ligand when said mammal is exposed to a hyperoxic condition.

9 Claims, 30 Drawing Sheets

OLD PARADIGM =LINEAR

STEM CELLS⇒EMBRYONIC DEV⇒DIFF⇒HOMEOSTASIS⇒INJURY/REPAIR

METHOD OF INHIBITING LIPOFIBROBLAST TO MYOFIBROBLAST TRANSDIFFERENTIATION

CROSS-REFERENCE TO RELATED APPLICATIONS

This application claims priority to and benefit of U.S. Ser. No. 60/377,665, filed on May 2, 2002 and U.S. Ser. No. 60/421,615, filed on Oct. 25, 2002, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported, in part, by Grant No: HL55268 from the National Heart, Lung and Blood Institute of the National Institutes of Health. The government of the United States of America may have certain rights in this invention.

FIELD OF THE INVENTION

This invention pertains to the field of chronic lung disease. In particular this invention pertains to the discovery that Parathyroid Hormone-related Protein (PTHrP) can be used to detect and/or stage, and/or treat chronic lung diseases

BACKGROUND OF THE INVENTION

Among aerobic animals, the lung functions to provide an interface for the exchange of gases between blood and the atmosphere. The agents of this exchange are numerous small sacs termed alveoli (in adult humans about 150,000,000 per lung) that provide a gas permeable-liquid impermeable barrier between the gas and liquid phases. Between the alveoli are numerous capillaries carrying deoxygenated blood to the lung from the tissues and oxygenated blood from the alveoli to the tissues. The partial pressure of oxygen in the lungs is approximately 100 mm Hg at sea level; at this pressure the binding of oxygen by hemoglobin in the erythrocytes is favored. The alveoli thus provide a means for presenting the oxygen to hemoglobin to permit the conversion of deoxyhemoglobin to hemoglobin. Because the exchange occurs at the surface of the gas/blood barrier, alveoli have evolved as a means for providing extremely high surface area in a compact overall area, thus maximizing possible gas exchange. Lack of adequate gas exchange leads to disability which can progress to death.

Diseases that result in fewer alveoli and/or the deflation of alveoli therefore are quite serious, and are common causes of inadequate oxygenation and frequently resultant in disability and death. Among such diseases are chronic lung diseases such as bronchopulmonary dysplasia (BPD), asthma, emphysema, and idiopathic pulmonary fibrosis. BPD is a disease of prematurely born infants, and is characterized mainly by a failure of the infant to form a sufficient number of appropriately-sized alveoli. Emphysema, a disease of middle and advanced age, appears to be due to progressive proteinase-induced alveolar destruction. Many of these pathological conditions are characterized by the dedifferentiation of lipofibroblasts to myofibroblasts, resulting in various fibroses.

A marker for the onset or progression of these diseases, and/or for the response of a patient (or veterinary subject) to various therapeutic regimes would greatly facilitate the treatment of such conditions.

SUMMARY OF THE INVENTION

This invention pertains to the discovery that PPAR gamma, ADRP, PTHrPR, and CP-CYT expression decreases and that alpha SMA expression increases in mammals subject to hyperoxia and that these changes are associated with the transdifferentiation of lipofibroblasts to myofibroblasts. Moreover, agents that partially or fully inhibit the decrease in expression of PPAR gamma, ADRP, PTHrPR, and CP-CYT and/or partially or fully inhibit the increase in expression of alpha SMA inhibited such transdifferentiation. Without being bound to a particular theory, we believe these data provide the first evidence of in vivo lipo-to-myofibroblast transdifferentiation during hyperoxic exposure of neonatal rat pups and its inhibition using various pharmacologic agents.

In addition, this invention pertains to the discovery that Parathyroid Hormone-related Protein (PTHrP) can be detect and/or stage, and/or treat chronic lung diseases. In particular, it was discovered that PTHrP levels in broncho-alveolar lavage are indicative of lung "health" and "disease, and can be used to predict lung disease in patients at risk of chronic lung disease. In addition, treatment with the protein or with an agent that upregulates PTHrP expression or activity or that mimics or induces an activity typically induced by elevated PTHrP will mitigate one or more symptoms of a chronic lung disease.

In one embodiment, this invention provides a method of inhibiting lipofibroblast to myofibroblasts transdifferentiation in a mammal. The method involves administering to the mammal a PPAR gamma ligand in a concentration sufficient to partially or fully inhibit lipofibroblast to myofibroblast transdifferentiation in the mammal when the mammal is exposed to a hyperoxic condition. In certain embodiments, the PPAR gamma ligand is a thiozolidinedione (TZD). In certain embodiments, the PPAR gamma ligand is selected from the group consisting of rosiglitazone, troglitazone (Resulin), farglitazar, phenylacetic acid, GW590735, GW677954, Avandia, Avandamet (avandia+metformin), ciglitazone, 15 deoxy prostaglandin J2 (15PGJ2), 15-deoxy-delta12,14 PGJ2, GW-9662, MCC-555, and the like. Certain preferred PPAR gamma ligands include, but are not limited to rosiglitazone or an analogue thereof. In one embodiment, the PPAR gamma ligand is administered in a concentration of at least 0.5 mg/kg, and often in a concentration of at least 1 mg/kg. The mammal can be a human (e.g., a human having or at risk for bronchopulmonary dysplasia) or a non-human mammal.

In another embodiment, this invention provides a method of mitigating one or more symptoms of a condition characterized by transdifferentiation of lipofibroblasts to myofibroblasts in a mammal. The method involves administering to the mammal a PPAR gamma ligand in a concentration sufficient to partially or fully inhibit lipofibroblast to myofibroblast transdifferentiation in the mammal. The PPAR gamma ligands include, but are not limited to any of the ligands described herein. In one embodiment, the PPAR gamma ligand is administered in a concentration of at least 0.5 mg/kg, and often in a concentration of at least 1 mg/kg. The mammal can be a human (e.g., a human having or at risk for bronchopulmonary dysplasia) or a non-human mammal. Again, the mammal can be a human (e.g., a human having or at risk for bronchopulmonary dysplasia) or a non-human mammal. The condition can include, but is not limited to a fibrosis, scleroderma, periodontal disease, endometriosis, pancreatic disease, chronic lung disease, acute lung disease, and obesity related lung disease. In one embodiment, the condition is bronchopulmonary dysplasia.

Also provided is a kit for mitigating one or more symptoms of a condition characterized by transdifferentiation of lipofibroblasts to myofibroblasts in a mammal. The kit typically includes a PPAR gamma ligand (e.g., as described herein), and instructional materials teaching the use of a PPAR gamma ligand to inhibit the transdifferentiation of lipofibroblasts to myofibroblasts in vivo.

This invention also provides a method of mitigating one or more symptoms of a condition characterized by transdifferentiation of lipofibroblasts to myofibroblasts in a mammal. This method involves administering to the mammal an agent that inhibits downregulation of one or more components selected from the group consisting of PPARgamma, ADRP, PTHrPR, and CP-CYT in a mammal exposed to hyperoxic conditions; and/or that inhibits upregulation of alpha SMA in a mammal exposed to hyperoxic conditions (e.g. 95% $O_2$ AND 5% $CO_2$). In certain embodiments, the condition is a lung disease. In certain embodiments, the agent can be a PPAR gamma ligand.

Also provided is a method method of screening for an agent that mitigates one or more symptoms of a condition characterized by transdifferentiation of lipofibroblasts to myofibroblasts in a mammal. The method involves exposing a test mammal to hyperoxic conditions; administering a test agent to the mammal; and determining the expression of one or more components selected from the group consisting of PPARgamma, ADRP, PTHrPR, CP-CYT, and alpha SMA' where inhibition of the hyperoxic-induced downregulation of one or more components selected from the group consisting of PPARgamma, ADRP, PTHrPR, and CP-CYT in a mammal exposed to hyperoxic conditions; and/or inhibition of the hyperoxic-induced upregulation of alpha SMA in the mammal indicates that said test agent is a good candidate agent for the mitigation of one or more symptoms of a condition characterized by transdifferentiation of lipofibroblasts to myofibroblasts in a mammal. In certain embodiments, determining the expression comprises measuring mRNA or protein expression of one or more components selected from the group consisting of PPARgamma, ADRP, PTHrPR, CP-CYT, and alpha SMA.

In still another embodiment, this invention provides a method of evaluating the progression of a chronic lung disease in a mammal. The method involves providing a sample comprising a fluid, cell, or tissue from the lung, trachea, or bronchi of said mammal; and measuring the level of parathyroid hormone related protein (PTHrP) where a lower level of PTHrP, as compared to the level found in a comparable sample from a normal healthy mammal indicates an increase in severity or progression of the lung disease. In one embodiment, the sample is a tracheal aspirate. The chronic lung disease includes, but is not limited to bronchopulmonary dysplasia, asthma, emphysema, or idiopathic pulmonary fibrosis. The mammal can be a human (e.g., a human child or infant) or a non-human mammal. In certain embodiments, the mammal is a human on a respirator. In certain embodiments, the measuring comprises measuring expressed PTHrP protein (e.g., via a method selected from the group consisting of capillary electrophoresis, a Western blot, mass spectroscopy, ELISA, immunochromatography, immunohistochemistry, etc.). In certain embodiments the measuring comprises measuring the level of a nucleic acid (e.g. PTHrP mRNA) encoding the PTHrP protein (e.g. by hybridizing said mRNA to a probe that specifically hybridizes to a PTHrP nucleic acid). Various methods for measuring the nucleic acid include, but are not limited to a Northern blot, a Southern blot using DNA derived from the PTHrP RNA, an array hybridization, an affinity chromatography, an in situ hybridization, and the like. In certain embodiments, the level of PTHrP mRNA is measured using a nucleic acid amplification reaction.

This invention also provides a method of evaluating the efficacy of a therapeutic regimen for the prevention or treatment of a chronic lung disease. This method involves providing a sample comprising a fluid, cell, or tissue from the lung or bronchi of the mammal; and measuring the level of parathyroid hormone related protein (PTHrP) where a level of PTHrP, compared to the level found is a comparable sample from a normal healthy mammal indicates efficacy of the therapeutic regimen and a level of PTHrP lower than the level found in a comparable sample from a normal healthy mammal indicates that the therapeutic regimen is of lower efficacy.

In still yet another embodiment, this invention provides a method of screening for an agent that mitigate one or more symptoms of lung disease. The method involves contacting a cell or tissue with the test agent; and detecting a change in expression of PTHrP or PTHrP receptor, where a decrease in expression or activity of PTHrP or PTHrP receptor indicates that said test agent mitigates one or more symptoms of lung disease. The lung disease can include, but is not limited to chronic lung disease, and acute lung disease. In certain embodiments, the cell or tissue can be a lung or tracheal cell or tissue.

In certain embodiments, a method is provided for screening for an agent that mitigates one or more symptoms of a pathology characterized by transdifferentiation of a mesodermal cell. The method involves contacting a cell or tissue with the test agent; and detecting a change in expression of PTHrP or PTHrP receptor, where a decrease in expression or activity of PTHrP or PTHrP receptor indicates that the test agent mitigates one or more symptoms of the pathology. In certain embodiments, the pathology includes, but is not limited to one or more of acute lung disease, chronic lung disease, obesity related lung disease, fibrosis, skin lesions, endometriosis; vascular smooth muscle cell proliferative disease, and diseases associated with prematurity. In certain embodiments, the cell or tissue is a cell or tissue selected from the group consisting of a lung cell or tissue, a skin cell or tissue, a uterine cell or tissue, and a vascular cell or tissue.

In still yet another embodiment, this invention provides a method of screening for an agent that mitigates one or more symptoms of a pathology selected from the group consisting of glial scarring, scleroderma, periodontal disease, osteoporosis, post-partum bladder disease, arthritis, pancreatic disease, and stroke. The method typically involves contacting a cell or tissue with the test agent; and detecting a change in expression of PTHrP or PTHrP receptor, where a decrease in expression or activity of PTHrP or PTHrP receptor indicates that the test agent mitigates one or more symptoms of the pathology. In certain embodiments, the cell or tissue is a cell or tissue selected from the group consisting of a uterine or bladder cell or tissue, a nervous cell or tissue, a cell or tissue from an oral cavity, and a pancreatic cell or tissue. In various screening methods described herein, the sample comprises a cell or tissue selected from the group consisting of a lung cell or tissue, a tracheal cell or tissue, a cervical or uterine cell or tissue, skin cell or tissue, a neurological cell or tissue, a pancreatic cell or tissue, a bone cell or tissue, and a connective tissue or cell and/or the mammal is a non-human mammal or a human (e.g. a human child or infant). In certain embodiments, measuring the activity or level of parathyroid hormone related protein or the activity or level of PTHrP receptor protein comprises measuring the level of the expressed PTHrP protein or PTHrP receptor protein (e.g. via capillary electrophoresis, a Western blot, mass spectroscopy, ELISA, immunochromatography, immunohistochemistry, and the like). In certain embodiments, measuring the activity or level of parathyroid hormone related protein or the activity or level of PTHrP receptor protein comprises measuring the level of a nucleic acid encoding the PTHrP protein or the PTHrP receptor protein. In some embodiments, the the level of nucleic acid encoding the PTHrP protein or the level of a nucleic acid encoding a PTHrP receptor protein is detected by detecting PTHrP mRNA or PTHrP receptor mRNA in said sample (e.g. by hybridizing said mRNA to a probe that specifically hybridizes to a PTHrP nucleic acid or to a PTHrP receptor nucleic acid). The hybridizing can be by any of a variety of methods including, but not limited to a Northern blot, a Southern blot using DNA derived from the PTHrP RNA or PTHrP receptor RNA, an array hybridization, an affinity chromatography, an in situ hybridization, and the like. In certain embodiments, the level of nucleic acid encoding the PTHrP protein or the level of a nucleic acid encoding a PTHrP receptor protein is measured using a nucleic acid amplification reaction. In certain embodiments, detecting a change in expression of PTHrP or PTHrP receptor comprises comparing the level or expression or activity in a test sample to the level or activity in a control sample. The control(s) can include a positive control comprising the test agent at a higher concentration than the test sample and/or a negative control comprising the test agent at a lower concentration than the test sample. In certain embodiments, the control is a negative control comprising the absence of the test agent.

In certain embodiments, the assay is scored as positive when the difference in expression level or activity as compared to a control is detectable. In certain embodiments, the assay is scored as positive when the difference in expression level or activity as compared to a control is statistically significant.

This invention also provides a method of prescreening for an agent that modulates one or more symptoms associated with a pathology selected from the group consisting of chronic lung disease, acute lung disease, obesity related lung disease, fibrosis, hypertension, glial scarring, restenosis, osteoporosis, scleroderma, arthritis, pancreatic disease, and stroke. The method typically involves contacting a test agent with a PTHrP or a PTHrP receptor or with a nucleic acid that encodes a PTHrP or a PTHrP receptor; and detecting specific binding of said test agent to said PTHrP or a PTHrP receptor or to said nucleic acid that encodes a PTHrP or a PTHrP receptor; where specific binding indicates that said test agent is a good candidate for an agent that modulates one or more symptoms of the pathology. The method can further involve recording test agents that specifically bind to PTHrP or a PTHrP receptor or to said nucleic acid that encodes a PTHrP or a PTHrP receptor, in a database of candidate therapeutic agents. In certain embodiments, the test agent is not an antibody and/or not not a protein, and/or not a nucleic acid. In certain embodiments, the test agent is a small organic molecule.

The method of claim 70, wherein said detecting comprises detecting specific binding of said test agent to said nucleic acid encoding a PTHrP or a PTHrP receptor. In various embodiments, the binding is detected by any of a variety of methods including, but not limited to a Northern blot, a Southern blot using DNA derived from a nucleic acid encoding a PTHrP or a PTHrP receptor, an array hybridization, an affinity chromatography, and an in situ hybridization. In certain embodiments, the detecting comprises detecting specific binding of the test agent to PTHrP or to the PTHrP receptor (e.g. via a method such as capillary electrophoresis, a Western blot, mass spectroscopy, ELISA, immunochromatography, immunohistochemistry, and the like). In certain embodiments, the test agent is contacted directly to the PTHrP or PTHrP receptor. In certain embodiments, the test agent is contacted to a cell containing the PTHrP or PTHrP receptor.

In one embodiment, this invention provides a method of mitigating a symptom associated with a chronic lung disease in a mammal. The method involves increasing the level of parathyroid hormone related protein (PTHrP) in the lung tissue of said mammal, and/or increasing the expression of PTHrP receptors in the lung tissue of the mammal, and/or mimicking the effects of increased PTHrP expression or activity downstream in a PTHrP-regulated pathway. In certain embodiments, the mimicking comprises one or more activities selected from the group consisting of upregulating cAMP-dependent PKA, inactivating GSK-3beta, activating beta catenin, activating LEF-1, activating C/EBPalpha; activating PPARgamma, upregulating ADRP, and upregulating leptin. In certain embodiments, the increased expression is by administering PTHrP or an analogue thereof.

This invention also provides a method of altering the amplitude and/or frequency of uterine contractions. This method typically involves increasing PTHrP expression or activity of PTHrP or the expression or activity of a PTHrP receptor to decrease the amplitude and/or frequency of uterine contractions. The "increasing" involves in certain embodiments, administering PTHrP or an analogue thereof to the subject organism (e.g. human or non-human mammal).

Also provided is a method of mitigating a symptom associated with a pathology selected from the group consisting of hepatic fibrosis, kidney fibrosis, cerebrovascular incident, skin fibrosis, scleroderma, gingival diseases, endometriosis, bladder epithelial hypertrophy, bladder disease, incontinence, overactive bladder, arthritis, and immaturity of the mesoderm in preterm infants. This method typically involves increasing the level of parathyroid hormone related protein (PTHrP), or increasing the expression of PTHrP receptors in the mammal, or mimicking the effects of increased PTHrP expression or activity downstream in a PTHrP-regulated pathway.

Definitions.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986)

*Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach,* Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research,* Ed. Y. S. Sanghui and P. Dan Cook. Nucleic acids containing one or more carbocyclic sugars are also included within the definition of nucleic acids (see Jenkins et al. (1995), *Chem. Soc. Rev. pp* 169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "specifically binds", as used herein, when referring to a biomolecule (e.g., protein, nucleic acid, antibody, etc.), refers to a binding reaction which is determinative of the presence of a biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays,* Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.)*Vol.* 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The terms "PPAR gamma ligand" and "PPAR gamma agonist" are used interchangeably and refers to an agent that upregulates directly or indirectly activity of a pathway mediated by a PPAR gamma receptor.

The term "hyperoxic conditions" refer to conditions that produce elevated $pO_2$ in a mammal as compared to the same mammal exposed to normal atmosphere (e.g. about 20% $O_2$). In certain embodiments, hyperoxic conditions comprise greater than 21% $O_2$, preferably greater than about 30% $O_2$, preferably greater than about 50% $O_2$, more preferably greater than about 75% $O_2$, and most preferably greater than about 90% or 95% $O_2$.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below (i.e. toward the Fc domain) the disulfide linkages in the hinge region to produce F(ab)'2, a dimer of Fab which itself is a light chain joined to $V_H$—$C_H1$ by a disulfide bond. The F(ab)'2 may be reduced under mild conditions to break the disulfide linkage in the hinge region thereby converting the (Fab')2 dimer into an Fab' monomer. The Fab' monomer is essentially a Fab with part of the hinge region (see, Paul (1993) *Fundamental Immunology*, Raven Press, N.Y. for a more detailed description of other antibody fragments). While various antibody fragments are defined in terms of the digestion of an intact antibody, one of skill will appreciate that such fragments may be synthesized de novo either chemically, by utilizing recombinant DNA methodology, or by "phage display" methods (see, e.g., Vaughan et al. (1996) *Nature Biotechnology*, 14(3): 309–314, and PCT/US96/10287). Preferred antibodies include single chain antibodies, e.g., single chain Fv (scFv) antibodies in which a variable heavy and a variable light chain are joined together (directly or through a peptide linker) to form a continuous polypeptide.

A "PTHrP nucleic acid" refers to a nucleic acid that encodes all or a fragment of PTHrP. Preferred PTHrP nucleic acids encode at least 8 amino acids, preferably at least 10, 15, or 20 amino acids of PTHrP, more preferably at least 25, or 30 amino acids of PTHrP, and most preferably a full length PTHrp.

The term "a PTHrP receptor" is used to mean a receptor that binds to PTHrP, and examples include a PTHrP type I receptor (described in Japanese Patent Application Laying-Open (kohyo) No. 6-506598).

BRIEF DESCRIPTION OF THE DRAWINGS

FIG. 24A: e18 day fibroblasts exhibited a significant decrease in pentose cycle activity after 95% oxygen treatment. FIG. 24B: Mature fibroblasts also showed a significant decrease; however, this decrease was less pronounced after 10 passages in the high oxygen-treated culture as compared to the controls. (Mean±SD; n=9)

FIG. 25A: e18 day fibroblasts exhibited a significant increase in $^{13}C$ accumulation from glucose into the ribose moiety of RNA in e18 fibroblast cultures in response to 95% oxygen treatment. FIG. 25B: e21 fibroblasts showed no significant increase in the nonoxidative reactions of the pentose cycle in 95% oxygen-treated cultures. (Mean±SD; n=9)

FIG. 26A: The fraction of newly synthesized palmitate from glucose in e18 day fibroblasts, which showed a significant decrease in the de novo synthesis of palmitate after 95% oxygen treatment. FIG. 26B: e21 day fibroblasts showed a less prominent decrease in new fatty acid synthesis. (Mean±SD; n=9)

FIG. 27A: The critically low, 1% to 2% $^{13}C$ enrichment in acetyl indicates a severe imbalance in glucose carbon redistribution toward the TCA cycle and de novo lipid synthesis in e18 fibroblasts after 95% oxygen treatment. FIG. 27B: e21 day fibroblasts showed higher $^{13}C$ distribution in acetate, indicating a more balanced carbon flow between glycolysis, fatty acid synthesis and the TCA cycle in 95% oxygen-treated cells. (Mean±SD; n=9)

DETAILED DESCRIPTION

Figure 1:
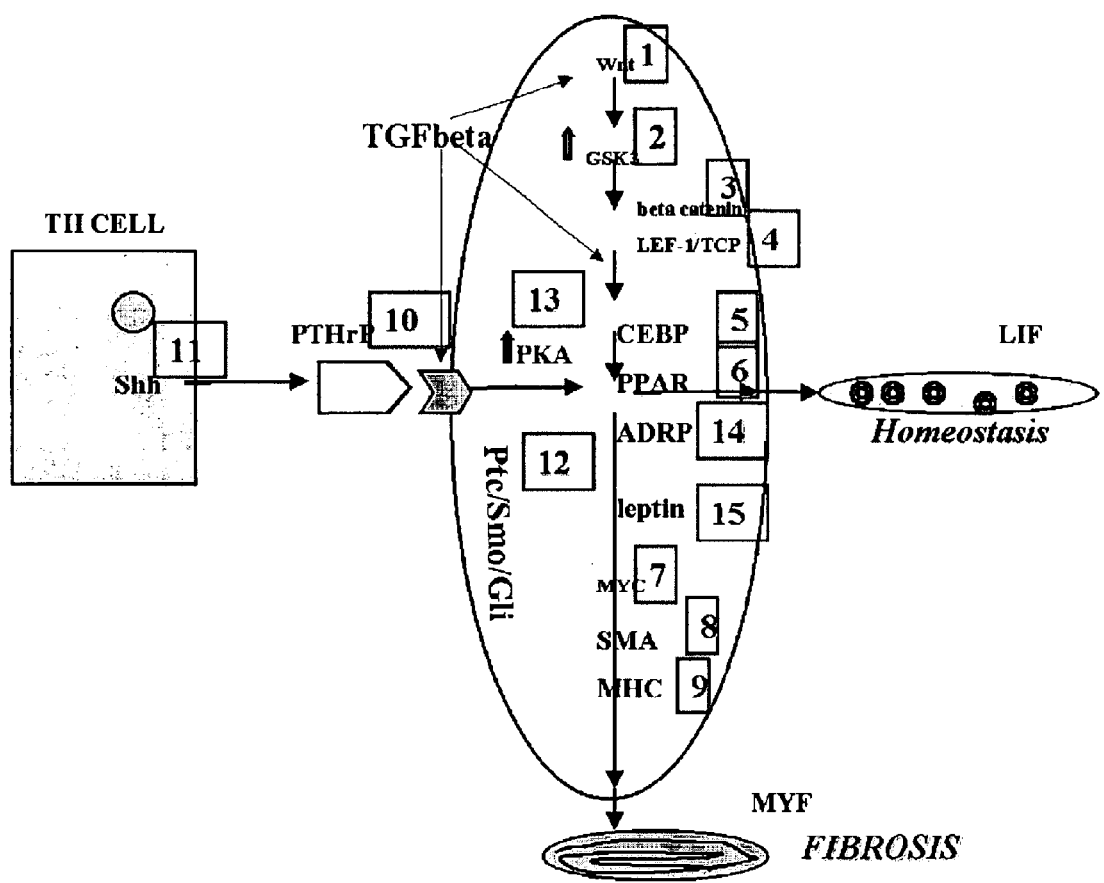
FIG. 1 shows a schema illustrating lung development.
Figure 2:
FIG. 2 shows a schematic illustrating the relationship between normal embryonic development and Injury/repair
Figure 2:
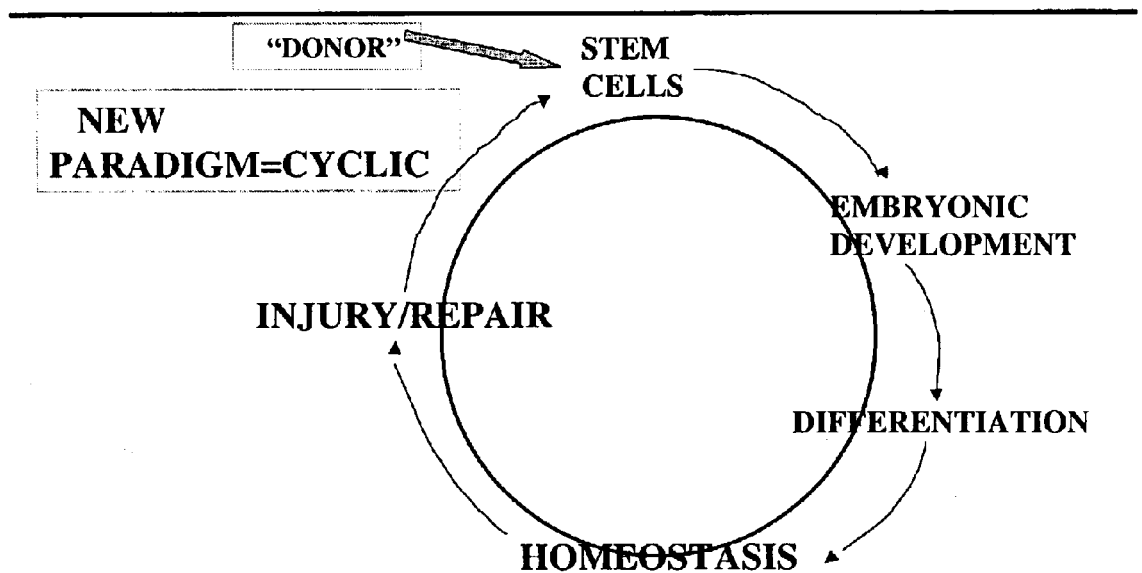
Figure 3:
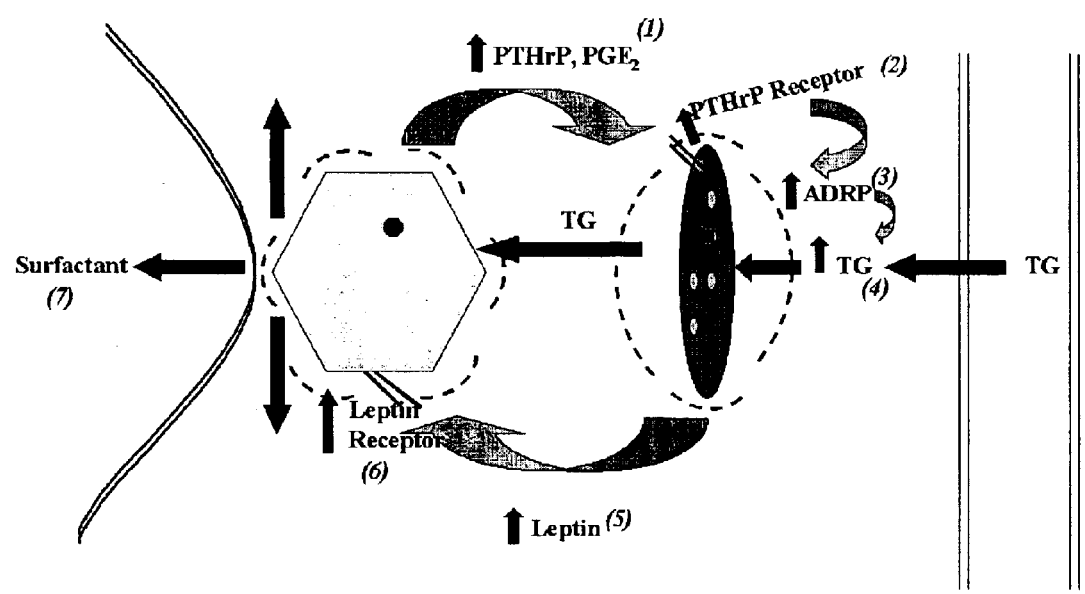
FIG. 3 shows a schematic illustrating the interrelationship between stretch, PTHrP and leptin in alveolar homeostasis.
Figure 4:
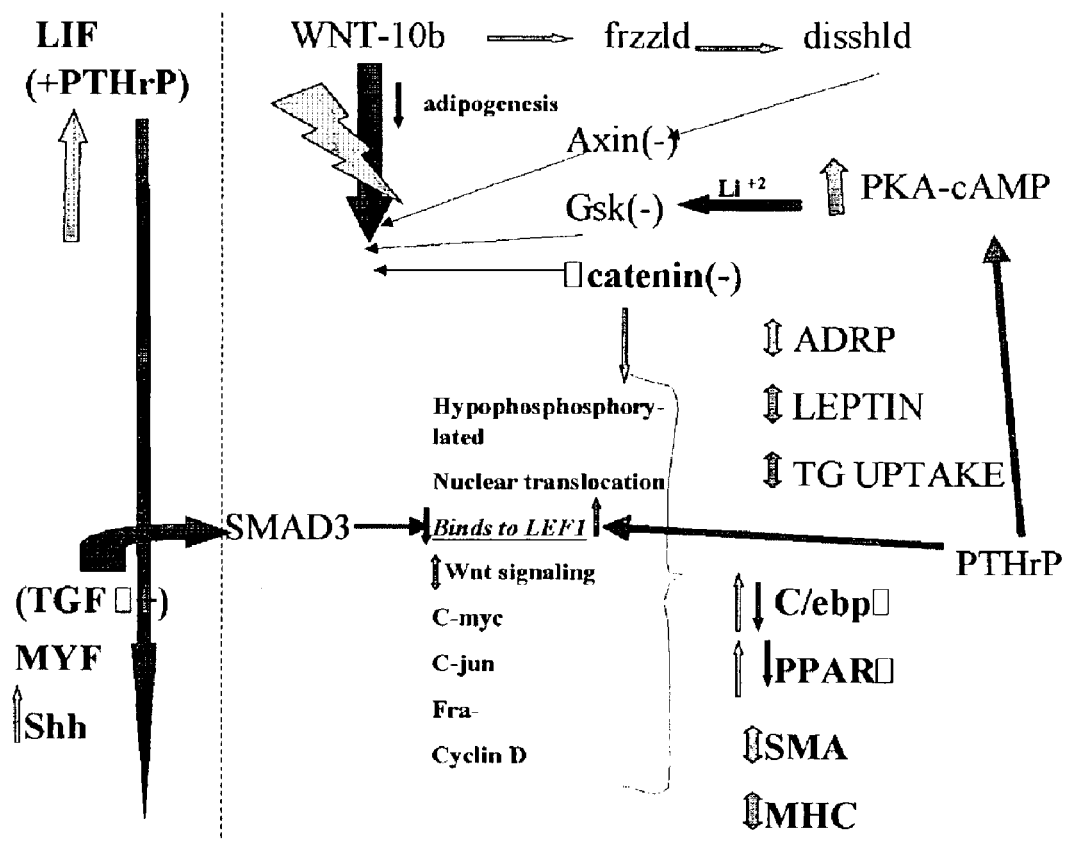
FIG. 4 provides an integrated schema showing how PTHrP reverses the dedifferentiation of lung fibroblasts. The myofibroblast is dominated by the Wnt pathway. However, PTHrP acts as a PKA agonist to inhibit Wnt signaling, shifting to the lipogenic pathway, characterized by PPAR, ADRP and leptin signaling, recapitulating the lipofibroblast-dominated alveolar homeostatic mechanism.

This invention pertains to the discovery that Parathyroid Hormone-related Protein (PTHrP) can be used to detect and/or stage, and/or treat chronic lung diseases as well as other pathologies, especially pathologies characterized by transdifferentiation of a mesodermal cell (e.g. lung disease, fibroses, etc.).

In particular, it was discovered that PTHrP levels in broncho-alveolar lavage are indicative of lung "health" and "disease, and can be used to predict lung disease in patients at risk of chronic lung disease. In the absence of PTHrP signaling through protein kinase A, the lung interstitial fibroblasts revert to myofibroblasts, the signature cell-type for fibrosis and alveolar dysfunction. Myofibroblasts utilize a different signal transduction pathway, referred to as the Wingless/Int or Wnt pathway, in which these cells produce and secrete such cell-specific products as Frizzled and cubitus interruptus, that can also be used to sensitively and specifically delineate the stage of alveolar dysfunction. Inhibitors of the Wnt pathway could also be used to prevent chronic lung diseases.

Based on this mechanism of molecular disruption of the PTHrP signal transduction pathway leading to pulmonary fibrosis, we have demonstrated that treatment with PTHrP itself early in the process reinstates the normal fibroblast phenotype. Later in the course of the loss of the normal fibroblast phenotype, when the PTHrP receptor is lost, the cells can be treated with transcription factors that can also restore the normal fibroblast phenotype. The restoration of the normal fibroblasts restores the mechanism of surfactant production, as well as the mechanism of re-epithelializing the alveolar surface layer. Therefore, by monitoring the molecular changes in the lung fibroblast population, the caregiver can effectively prevent or treat chronic lung disease.

It was also a surprising discovery that that PPAR gamma, ADRP, PTHrPR, and CP-CYT expression decrease, and that alpha SMA expression increases in mammals subject to hyperoxia and that these changes are associated with the transdifferentiation of lipofibroblasts to myofibroblasts. Moreover, agents that partially or fully inhibit the decrease in expression of PPAR gamma, ADRP, PTHrPR, and CP-CYT and/or partially or fully inhibit the increase in expression of alpha SMA inhibited such transdifferentiation and are useful lead candidates or actual compounds useful in the treatment of pathological conditions characterized by such transdifferentiation.

PTHrP metabolism also provides an important "organizing principle" for the alveolus of the lung. In the womb, lung epithelial cells express PTHrP, and the PTHrP receptor is present on neighboring mesenchymal fibroblasts. As fluid fills the lung it distends the airway, increasing both epithelial PTHrP production and mesodermal PTHrP receptor binding. The net result is induced differentiation of fibroblasts, which in turn produce leptin, that stimulates epithelial cell differentiation. This process is essential for lung function at the time of birth, as well as in newborns and throughout life.

At birth the lung fills with air (containing 21% oxygen). This sudden increase in stretch and oxygen inhibits PTHrP/ PTHrP signaling particularly by those epithelial and mesodermal cells towards the middle of the alveolar wall, but not in the corners of the alveolus. As a result, PTHrP signaling is maintained in the corners, but is "uncoupled" towards the middle, resulting (1) in the programmed cell death (apoptosis) of some mesodermal cells, (2) transdifferentiation of other mesodermal cells to myofibroblasts, (3) the formation of alveolar septa by those myofibroblasts, (4) and the transdifferentiation of the epithelial type II cells which had been associated with the apoptotic mesodermal cells to type I cells, the major lining cell type of the alveolus responsible for exchange of oxygen and carbon dioxide with the circulation. The PTHrP signaling is maintained in the corners because there is less stretching there, and because PTHrP stimulates the expression of Insulin-like Growth Factor (IGF) by the fibroblasts below them. Both IGF and the lipids contained within these type II cell-associated mesodermal fibroblasts prevent cell death.

This is an important conceptual framework in which to consider normal lung development, function and dysfunction because PTHrP is a stretch-sensitive molecular sensor that controls and integrates the synthesis of pulmonary surfactant and alveolar capillary perfusion, i.e. when alveolar volume increases, PTHrP is stimulated, causing a simultaneous increase in both surfactant production and alveolar capillary perfusion. This interrelationship between PTHrP, stretch, alveolar surfactant economy and alveolar capillary perfusion represents the first mechanism ever described for "ventilation-perfusion matching", a basic principle of pulmonary physiology.

The other affect of alveolar wall remodeling post-birth is the alveolar capillary vasculature, which invades the epithelium during the thinning of the septa. The lung receives only 10% of the blood from the heart in the womb. After birth the lung receives 100% of cardiac output, causing a 10-fold increase in blood flow to the alveoli. As a result of this increase of blood flow through the lung, blood vessel lining cells produce endothelin, which further promotes uncoupling of PTHrP/PTHrP signaling leading to programmed death of mesoderm, transdifferentiation of myofibroblasts for septation, and type II cell to type I cell conversion. The blood vessels exacerbate the stretching effect, but in the process also ensure the close association of the capillaries with the type I cells for efficient gas exchange by eliminating mesodermal cells and "carving out" (and creating) this close structural relationship between type I cells and vessels.

This model of lung structural development and homeostasis is a paradigm shift because it implies an intimate interrelationship between structure and function determined by physiologic interactions between lung cells and their physical environment. Damage to either the epithelium, mesoderm and or vasculature interrupts PTHrP signaling, leading to myofibroblast proliferation and fibrosis. Myofibroblast multiplication is acutely detrimental because these cells do not have the capacity to integrate ventilation-perfusion matching by PTHrP, resulting in chronic pulmonary insufficiency and heart disease. Myofibroblasts are chronically detrimental because unlike the normal interstitial fibroblasts, these cells cannot support growth and repair of alveoli. This model also suggests that there are many ways in which altered cellular structure can lead to altered function in readapting to changes in lung volume, blood flow, or biological and chemical factors that can molecularly disrupt these interrelationships.

I. Inhibition of the Transdifferentiation of Lipofibroblasts to Myofibroblasts In Vivo.

It was a surprising discovery that PPAR gamma ligands can be used to inhibit the transdifferentiation of lipofibroblasts to myofibroblasts in a mammal subject to hyperoxic conditions (e.g. 95% $O_2$+5% $CO_2$) (see, e.g., Example 5). Hyperoxia resulted in significant decreases in PPAR gamma, ADRP, PTHrPR, and CP-CYT mRNA and corresponding protein expressions, and a significant increase in alpha SMA mRNA expression.

The decreases in PPAR gamma, ADRP, PTHrPR, and CP-CYT expression and the increase in alpha SMA expression were partially (at 1 mg/kg rosiglitazone) or completely (at 3 mg/kg rosiglitazone) prevented by the simultaneous treatment with rosiglitazone at the beginning of the hyperoxic exposure. Without being bound to a particular theory, we believe these data provide the first evidence of in vivo lipo-to-myofibroblast transdifferentiation during hyperoxic exposure of neonatal rat pups and its complete prevention by the simultaneous administration of rosiglitazone.

We believe that treatment with PPAR gamma ligands is an effective preventive and therapeutic strategy for bronchopulmonary dysplasia and other conditions characterized by transdifferentiation of lipofibroblasts to myofibroblasts (e.g., fibrosis, scleroderma, periodontal disease, endometriosis, pancreatic disease, chronic lung disease, acute lung disease, and obesity related lung disease).

In view of these discoveries, in certain embodiments, this invention provides a method of mitigating one or more symptoms of a condition characterized by transdifferentiation of lipofibroblasts to myofibroblasts in a mammal. The methods involve administering to the mammal an agent (e.g. a PPAR gamma ligand) that inhibits downregulation of PPARgamma, and/or ADRP, and/or PTHrPR, and/or CP-CYT and/or that inhibits upregulation of alpha SMA in a mammal exposed to hyperoxic conditions.

PPAR gamma ligands are particularly well suited to the methods of this invention. PPAR gamma ligands can include PPAR gamma specific ligands and/or ligands that activate receptors other than PPAR gamma (e.g. PPAR beta). PPAR gamma ligands are well known to those of skill in the art and include, for example, t thiozolidinediones (TZD). Particularly preferred PPAR gamma ligands include, but are not limited to rosiglitazone, troglitazone (Resulin), farglitazar, phenylacetic acid, GW590735, GW677954, Avandia, Avandamet (avandia+metformin), ciglitazone, 15 deoxy prostaglandin J2 (15PGJ2), 15-deoxy-delta12,14 PGJ2, GW-9662, MCC-555, and the like.

The methods of mitigating one or more symptoms of a condition characterized by transdifferentiation of lipofibroblasts to myofibroblasts in mammal can be performed with agents other than PPAR gamma ligands. Without being bound by a particular theory, it is believed that essentially any agent that inhibits downregulation of PPAR gamma, and/or ADRP, and/or PTHrPR, and/or CP-CYT in a mammal exposed to hyperoxic conditions; and/or that inhibits upregulation of alpha SMA in a mammal exposed to hyperoxic conditions will be effective to mitigate transdifferentiation of lipofibroblasts to myofibroblasts and thus will be of use in treating conditions characterized by such transdifferentiation.

Suitable compounds can be readily identified by routine screening. For example, an animal can be exposed to one or more test agents and then subjected to hyperoxic conditions (e.g. as described in Example 5). Expression levels of PPARgamma, and/or ADRP, and/or PTHrPR, and/or CP-CYT, and/or alpha SMA can be readily ascertained and suitable effect test agents thus readily identified.

II. Administration of Agents to Mitigate Symptoms of a Condition Characterized by Transdifferentiation of Lipofibroblasts to Myofibroblasts.

In certain embodiments, one or more symptoms of a condition characterized by transdifferentiation of lipofibroblasts to myofibroblasts are mitigated by administration of one or more agents that partially or fully inhibit transdifferentiation of lipofibroblasts to myofibroblasts.

In certain embodiments, one or more of the conditions described herein are treated by modulating activity of PTHrP and/or the PTHrP, and/or PPARgamma, and/or ADRP, and/or CP-CYT and/or alpha SMA and/or other components in the PTHrP signaling pathway. In certain embodiments, this is accomplished simply by administration of PTHrP and/or a biologically active fragment thereof (e.g. (7-34) PTHrP amide) and/or an analogue thereof and/or one or more agents identified in the screening methods described herein. In certain embodiments, this is accomplished by administering a PPAR gamma ligand or other agent that inhibits hyperoxic-induced downregulation of PPARgamma, ADRP, PTHrPR, and/or CP-CYT and/or that inhibits hyperoxic-induced upregulation of alpha SMA.

A variety of reagents that alter/modulate PTHrP and/or the PTHrP receptor and/or a downstream component in the PTHrP signaling cascade are known to those of skill in the art (see, e.g., WO0102011, EP1197225, etc.).

Similarly, a number of PPAR gamma ligands are known to those of skill and include, but are not limited to rosiglitazone, troglitazone (Resulin), farglitazar, phenylacetic acid, GW590735, GW677954, Avandia, Avandamet (avandia+metformin), ciglitazone, 15 deoxy prostaglandin J2 (15PGJ2), 15-deoxy-delta12,14 PGJ2, GW-9662, MCC-555, and the like. PPAR gamma ligands are also described, for example, in U.S. Pat. Nos. 6,498,156, 6,462,046, and 3 6,022,897.

A) Formulations

In order to carry out the methods of the invention, PTHrP, PtHRP fragments, analogues thereof or the other active agents of this invention (e.g. PPAR gamma ligands) are administered, e.g. to an individual diagnosed as having one or more symptoms of the various pathologies described herein (e.g. lung disease). The agent can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more pathological conditions described herein and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The active agents of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

In certain preferred embodiments, the active agents of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) Biotechnol. Prog. 14: 108; Johnson et al. (1996), Nature Med. 2: 795; Herbert et al. (1998), Pharmaceut. Res. 15, 357) a dry powder composed of biodegradable polymeric microspheres containing the protein in a polymer matrix that can be compounded as a dry formulation with or without other agents.

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

B) Effective Dosages.

The inhibitors of transdifferentiation of lipofibroblasts to myofibroblasts will generally be used in an amount effective to achieve the intended purpose (e.g. to reduce or prevent the inhibitors of transdifferentiation of lipofibroblasts to myofibroblasts in one or more pathological conditions (e.g. lung disease)). In preferred embodiments, the agent(s) utilized in the methods of this invention are administered at a dose that is effective to partially or fully inhibit the transdifferentiation of lipofibroblasts to myofibroblasts in the pathological condition being treated. In certain instances, such a dosage is comparable to the dosage that partially or fully inhibit the transdifferentiation of lipofibroblasts to myofibroblasts in an otherwise normal mammal subject to hyperoxic conditions (e.g., a statistically significant decrease at the 90%, more preferably at the 95%, and most preferably at the 98% or 99% confidence level). The compounds can also be used prophalactically at the same dose levels.

Typically, the inhibitors of transdifferentiation of lipofibroblasts to myofibroblasts, or pharmaceutical compositions thereof, are administered or applied in a therapeutically effective amount. A therapeutically effective amount is an amount effective to reduce or prevent one or more symptom characteristic of a condition characterized by such transdifferentiation. Determination of a therapeutically effective amount is well within the capabilities of those skilled in the art, especially in light of the detailed disclosure provided herein. Thus, for example, in certain embodiments, a therapeutically effective amount of a PPAR gamma ligand (e.g. rosiglitazone) varies from about 0.1 mg/kg to about 100 mg/kg, preferably from about 1 mg/kg to about 25 or 50 mg/kg, most preferably from about 3 mg/kg to about 20 mg/kg.

In certain embodiments, an initial dosage of about 1 mg/kg daily, preferably from about 1 mg to about 1000 mg per kilogram daily will be effective. Daily dose ranges can include about 3 mg/kg to about 100 mg/kg is preferred, preferably about 3 mg/kg to about 50 mg/kg, and more preferably about 3 mg/kg to about 25 or 10 mg/kg. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. or convenience, the total daily dosage may be divided and administered in portions during the day if desired.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One skilled in the art could readily optimize administration to humans based on animal data.

Dosage amount and interval may be adjusted individually to provide plasma levels of the inhibitors which are sufficient to maintain therapeutic effect.

Dosages for typical therapeutics, particularly for PPAR gamma ligands, are known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient.

In cases of local administration or selective uptake, the effective local concentration of the inhibitors may not be related to plasma concentration. One skilled in the art will be able to optimize therapeutically effective local dosages without undue experimentation. The amount of inhibitor administered will, of course, be dependent on the subject being treated, on the subject's weight, the severity of the affliction, the manner of administration and the judgment of the prescribing physician.

The therapy may be repeated intermittently. The therapy may be provided alone or in combination with other drugs and/or procedures.

C) Toxicity.

Preferably, a therapeutically effective dose of the inhibitors of transdifferentiation of lipofibroblasts to myofibroblasts described herein will provide therapeutic benefit without causing substantial toxicity.

Toxicity of the inhibitors described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). It is noted that toxicity of numerous PPAR gamma ligands is well characterized. The dose ratio between toxic and therapeutic effect is the therapeutic index. Inhibitors which exhibit high therapeutic indices are preferred. The data obtained from these cell culture assays and animal studies can be used in formulating a dosage range that is not toxic for use in human. The dosage of the inhibitors described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al. (1975) In: *The Pharmacological Basis of Therapeutics,* Ch. 1, p. 1).

III. PTHrP in the Diagnosis, Monitoring, and Treatment of Lung Disease

We have found that the PTHrP content of the lung effluent is indicative of the physiologic or pathologic condition of the lung. Furthermore, we have found that PTHrP treatment can prevent the dedifferentiation of lipofibroblasts to myofibroblasts, therefore preventing fibrosis. If the dedifferentiation process has gone beyond the point where the PTHrP receptor is expressed, down-stream targets for PTHrP signaling can be stimulated in order to recover the lipofibroblast phenotype, i.e. "cure" pulmonary fibrosis. In addition, or alternatively, components of the Wnt pathway leading to the differentiation of lipofibroblasts to myofibroblasts can be blocked.

As illustrated in FIG. 1, lung development is determined by a series of alternating mesenchymal-epithelial-mesenchymal interactions mediated by soluble growth and differentiation factors. Mesodermal fibroblasts provide the scaffolding for the upper and lower airways and alveoli. The subsequent appearance and proliferation of the endodermally-derived epithelium along the primordial airway surface initiates cell-cell interactions which induce the definitive phenotypes of the estimated 40 different lung cell types that are derived from these two otherwise homogeneous germ layers. In the absence of an epithelial influence (see FIG. 1), the mesoderm is dominated by the Wingless/int (Wnt) pathway, which is the default program for muscle. At the same time, the Wnt pathway actively inhibits lipofibroblast formation, by down-regulating C/EBPalpha and its downstream target, PPARgamma. The functionally relevant molecular intermediates in the Wnt pathway are GSK 3beta, beta catenin, LEF-1/TCP, C/EBPalpha and PPARgamma. These molecules interact with one another through a series of canonical interactions involving a variety of mechanisms, including phosphorylation, proteolysis and ubiquitination. This cascade culminates in the expression of the c-Myc oncogene. c-Myc up-regulates alpha smooth muscle actin and myosin heavy chains, which are characteristic of the muscle phenotype.

Lung epithelium expresses Parathyroid Hormone-related Protein (PTHrP) under the control of Sonic Hedgehog (Shh). Neighboring mesodermal cells express the PTHrP receptor early in embryonic lung morphogenesis. Expression of the PTHrP receptor is under the control of the downstream targets of Shh, namely Patched(Ptc)/Smoothened(Smo) and Gli. Down-regulation of the myogenic program of mesodermal differentiation is an active process under the influence of PTHrP, cAMP-dependent PKA is up-regulated. This results in the inactivation of GSK 3beta, followed by the sequential down-stream activation of beta catenin, LEF-1, C/EBPalpha and PPARgamma. The down-stream targets for PPARgamma are adipogenic regulatory genes such as ADRP and leptin. Therefore, by stimulating the PKA pathway, PTHrP coordinately down-regulates the myogenic pathway and up-regulates the lipofibroblast phenotype, which is necessary for maintaining alveolar homeostasis.

In view of these discoveries, this invention provides methods for the diagnosis and/or treatment of lung disease (e.g. acute lung disease, chronic lung disease, obesity related lung disease, and lung diseases associated with prematurity). The diagnostic methods simply involve obtaining a biological sample (e.g. a sample of lung or tracheal tissue, cells, aspirate, etc.) from the subject (e.g. a patient, a non-human mammal, etc.) and screening them for PTHrP, and/or a downstream component of the PTHrP cascade, and/or for PTHrP receptor(s). A decrease in PTHrP expression or activity (e.g. as compared to a normal healthy mammal) indicates increasing serverity of lung disease and is an indication for treatment (e.g. provision of PTHrP or analogues thereof).

Lung disease can be treated by administering PTHrP or biologically active fragments thereof (e.g. for PTHrP(1-34), H-ala-val-ser-glu-his-gln-leu-leu-his-asp-lys-gly-lys-ser-Ile-gln-asp-leu-arg-arg-arg-phe-phe-leu-his-his-leu-Ile-ala-glu-Ile-his-thr-ala-OH (SEQ ID NO:1) which eliminates the calcium effect of PTHrP) and/or analogues thereof. Alternatively, PTHrP receptor expression can be upregulated or components of the PTHrP signaling pathway can be activated and/or upregulated.

PTHrP and PTHrP receptor levels can similarly be of diagnostic and therapeutic value in acute lung disease and obesity related lung disease.

IV. Monitoring and/or Evaluating a Ventilation Regime.

In initial studies, we found that PTHrP levels in tracheal aspirates from mechanically ventilated baboons exposed to mechanical ventilation remains low, whereas in control animals subjected to little or no mechanical ventilation the levels of PTHrP increased more than 10-fold over the course of the first 10 days of postnatal life. It was subsequently discovered that in overdistended cultured alveolar epithelial cells derived from term (day 21) down-regulation of PTHrP mRNA expression was down regulated.

It was then determined that the PTHrP content of the lung effluent is indicative of the physiologic or pathologic condition of the lung. Without being bound to a particular theory, it is believed that because PTHrP is sensitive to stretch, it mediates moment to moment ventilatory changes. If the alveolus is damaged, PTHrP/PTHrP receptor expression is lost, potentiating the dedifferentiation of lipofibroblasts to myofibroblasts, resulting in fibrosis. Therefore PTHrP is an important functional marker for the health and disease of the lung. PTHrP levels can be monitored in patients on mechanical ventilators to determine if the settings are "therapeutic".

In general, a decrease in PTHrP expression or activity (e.g. as compared to that in a healthy subject or as compared to that measured at an earlier time in the same subject) indicates that a particular ventilation regime is sub-optimal. The ventilation region can then be appropriately adjusted.

V. PTHrP in the Diagnosis, Monitoring, and Treatment of Other Pathologies.

It was also a discovery of the inventors that PTHrP and/or its cognate receptor provides an important target for use in the diagnosis, monitoring, and treatment of other pathologies. For example, it is believed that PTHrP is implicated in the etiology of various fibroses. Thus, for example, PTHrP is expressed in the liver, and, without being bound by a particular theory, we believe neutral lipid homeostasis is regulated by it. In bile duct obstruction, PTHrP is affected, leading to liver fibrosis. Thus, PTHrP expression can provide a diagnostic for liver fibrosis and modulation of PTHrP (e.g. treatment with PTHrP or a fragment or analogue thereof) can be used to mitigate liver fibrosis.

Similarly, in kidneys, PTHrP is expressed by the mesangial cells. Again, without being bound by a particular theory, we believe PTHrP acts as a mechanotransducer for matching of blood volume and urine formation. When this system breaks down, e.g., in hypertension, the dysregulation of the PTHrP signaling cascade can lead to myofibroblast proliferation as in the lung model. Moreover, PTHrP signaling has been shown to be down-regulated in a variety of conditions resulting in chronic renal failure. In fact, the down-regulation of renal PTH/PTHrP receptor mRNA occurs much earlier than other traditional markers of changes in renal function, plasma PTH, serum phosphorus and calcium in the course of human renal disease. Thus, PTHrP expression can provide a diagnostic for kidney fibrosis and modulation of PTHrP (e.g. treatment with PTHrP or a fragment or analogue thereof) can be used to mitigate kidney fibrosis.

PTHrP activity is also implicated in hypertension. The Barker Hypothesis indicates that the set point for blood pressure is set in the womb. The mesangial cells of the kidney, which signal through PTHrP, can be programmed to express PTHrP in the determination of blood pressure. The anti-endothelin effect of PTHrP can be exploited for the management of hypertension (although desensitization of vascular smooth muscle cells may be of concern).

PTHrP is also implicated in glial scarring, stroke, and Alzheimer's disease. PTHrP is expressed in the meninges, and its receptor is expressed in the neuron, indicating a signaling pathway. The dissociation of the neuron from the Schwann cell in gliosis and the subsequent glial proliferation can be due a breakdown in PTHrP signaling. In stroke, change in vascular flow may affect endothelin expression, down-regulating PTHrP signaling leading to brain injury. In addition, PTHrP regulates IGF, which is neuroprotective; PTHrP treatment protects against brain injury experimentally.

PTHrP is a member of the neuroendocrine homeostatic system of the skin. PTHrP acts as a paracrine factor for the stabilization melanocytes and keratinocytes. It is associated with specific mesodermal cells that can be implicated in autoimmune diseases like scleroderma, psoriasis, etc. Modulation of PTHrP activity and/or PTHrP receptor activity and/or treatment with PTHrP or fragments or analogues thereof can be use in the treatment of such skin diseases.

PTHrP is implicated in another skin pathology, scleroderma. In this autoimmune disease, T cells programmed to recognize self wreak havoc, particularly in skin and lung, both of which are characterized by mesodermal cells which have immunologic epitopes on their surfaces. Interaction of the T cells with these resident immunocompetent fibroblasts can induce cryptogenic inflammation, which can uncouple the PTHrP signaling cascade. Restoration or normal PTHrP signaling or induction or simulation of such signaling can rectify this pathology.

In post-balloon catheterization vascular smooth muscle cell proliferative disease PTHrP is expressed by endothelium, and has been shown to be affected by this procedure. Elsewhere, it has been shown that PTHrP is a mitogen for vascular smooth muscle cells. PTHrP expression in atherosclerotic lesions and its role in the development of arterial neointima formation following balloon dilatation of rat femoral artery has clearly demonstrated that PTHrP inhibits the development of neointimal formation.

PTHrP can also play a role in periodontal disease. Gingival fibroblasts express the PTHrP receptor. Gingivitis is characterized by an imbalance between fibroblasts and epithelial cells in the gums. Without being bound by a particular theory, we believe gingivitis can be the product of a breakdown in the epithelio-mesenchymal communication within the gums, particularly in smokers, given our data to show that nicotine inhibits PTHrP signaling.

In osteoporosis, decreased muscle tone may release tension on bone, leading to decreased PTHrP-PTHrP receptor signaling and calcium loss, i.e. osteoporosis. We have shown experimentally that microgravity causes loss of PTHrP signaling in osteoblasts (see, examples). Furthermore, analysis of bones from rats flown in space has revealed decreased PTHrP signaling, but only by weight-bearing bones, consistent with the gravity hypothesis. Again, restoration of PTHrP signaling can mitigate this condition.

PTHrP is also implicated in endometriosis. PTHrp and its receptor are expressed in the myometrium, indicating a signaling pathway. Here too infection may disrupt the pathway, leading to myofibroblast proliferation, changing the mesodermal cell population.

In rheumatoid arthritis, we believe infection disrupts PTHrP signaling, causing bone wasting. It has been observed that synovial fluid levels of C-PTHrP was markedly higher in rheumatoid arthritis (RA) patients. Overexpression of PTHrP in synovial membranes with its subsequent secretion in synovial fluid seems to reflect the activity in RA.

Islet cells express PTHrP, and PTHrP stimulates insulin secretion. Infection, hyperglycemia (as in hyperglycemia effect on lung development) can interrupts PTHrP/PTHrP receptor signaling causing dysregulation of insulin secretion and the onset of pancreatic disease. It is believed that restoration of normal PTHrP signaling or activity can mitigate such symptoms.

PTHrP expression and signaling can also be implicated in essentially all the diseases related to prematurity due to the common mesodermal immaturity respiratory distress syndrome, necrotizing enterocolitis, retinopathy of prematurity, intraventricular hemorrhage, skin barrier immaturity-like the lung, are characterized by an immature mesoderm that is sensitive to oxygen, predisposing all to fibrosis.

In addition, PTHrP signaling is implicated in post-partum bladder disease (hyperdistension incontinents)

The above-identified conditions are characterized by a breakdown in PTHrP signaling. Thus, evaluation of PTHrP expression or activity and/or PTHrP receptor expression and/or activity can provide a method of staging, prognosing, or diagnosing these conditions. Moreover, it is believed that one or more symptoms of these conditions can be reduced/alleviated by restoring normal PTHrP signaling, and/or by administration of PTHrP, PTHrP fragments or analogues, or by inducing PTHrP receptor signaling (e.g. with small organic molecules) or activating one or more downstream components of the PTHrP receptor signaling cascade. This is particularly true for Peroxisome Proliferator Activated Receptor gamma. Alternatively, inhibitors of the Wnt pathway can be used to restore PTHrP/PTrP receptor signaling.

In another embodiment, PTHrP, PTHrP fragments, and/or PTHrP analogues find use as tocolytics. PTHrP is expressed by the fetal membranes, increases with development, and rapidly decreases at parturition. PTHrP causes myometrial contraction. PTHrP causes uterine relaxation and decreases both the amplitude and frequency of uterine contractions. Intrauterine infection may stimulate cytokines that may "precociously" uncouple PTHrP signaling.

VI. Detecting and/or Monitoring PTHrP, PPARgamma, ADRP, PTHrPR, CP-CYT mRNA and/or SMA.

The expression or activity of PTHrP, and/or PTHrP receptor, and/or PPAR gamma, and/or ADRP, and/or PTHrPR, and/or CP-CYT, and/or SMA PTHrP can be monitored by any a variety of methods. Typically a biological sample is obtained from the subject of interest, e.g. human or non-human mammal. The biological sample is preferably obtained from a site or tissue relevant to the pathology of interest. Thus, for example, where the pathology of interest is lung disease, a cell or tissue from lung, trachea or aspirate therefrom is a particularly well suited biological sample.

The expression or activity of the component of interest (e.g. PTHrP, PTHrP receptor) expression and/or activity can then be measured by measuring the protein component itself, a fragment thereof, nucleic acids encoding the protein component or fragment thereof, and/or by measuring activity of the protein or receptor. Illustrative methods are described below in the context of screening for modulators of such expression or activity.

VII. Screening for Modulators of PTHrP, PTHrP, PPARgamma, ADRP, PTHrPR, CP-CYT mRNA and/or SMA As indicated above, in one aspect, this invention pertains to the discovery that PTHrP is implicated in a number of pathologies, particular pathologies characterized by transdifferentiation of a mesodermal cell. Thus, PTHrP and/or the PTHrP receptor and/or downstream component in the PTHrP signaling cascade provide good targets to screen for modulators (e.g. up regulators or inhibitors) of PTHrP signaling.

In another aspect, this invention pertains to the discovery that inhibitors of hyperoxic induced decreases in PPARgamma, and/or ADRP, and/or PTHrPR, and/or CP-CYT and inhibitors of hyperoxic induced increase in alpha SMA expression partially or completely inhibit the transdifferentiation of lipofibroblasts to myofibroblasts were, and that one good class of such inhibitors includes PPAR gamma ligands.

These modulators can be useful in a wide variety of contexts (e.g. in the treatment of one or more of the conditions described above).

In certain embodiments, methods of identifying modulators involve contacting a cell (preferably a cell a particular target tissue, e.g. a lung tissue, or an isolated fibroblast) with a test agent and detecting a change in expression or activity of PTHrP and/or the PTHrP receptor and/or another component in the PTHrP signaling cascade (e.g., PPARgamma, ADRP, PTHrPR, CP-CYT, alpha SMA, etc.). An increase in expression or activity of PTHrP and/or the PTHrP receptor and/or PPARgamma, and/or ADRP, and/or CP-CYT, and/or a decrease in expression or activity of alpha SMA indicates that the test agent can be useful in treating many of the conditions described herein.

In certain embodiments, methods of identifying modulators (i.e. potential or actual therapeutic agents) involve administering one or more test agents to a mammal and subjecting that mammal to hyperoxic conditions (e.g. as described in Example 5). Agents that inhibit the hyperoxic-induced downregulation of PPAR gamma, ADRP, PTHrPR, CP-CYT and/or the hyperoxic-induced upregulation of alpha SMA will inhibit the transdifferentiation of lipofibroblasts to myofibroblasts are good actual or candidate agents for mediating symptoms of a pathology characterized by such a transdifferentiation (e.g. pulmonary disease).

When screening for modulators, a positive assay result need not indicate that a particular test agent is a good pharmaceutical. Rather a positive test result can simply indicate that the test agent can be used to modulate expression or activity of PTHrP and/or the PTHrP receptor and/or a downstream component in the PTHrP signaling cascade and/or can also serve as a lead compound in the development of other modulators (e.g., agonists).

Using known activities, and/or nucleic acid sequences, and/or amino acid sequences of PTHrP and/or the PTHrP receptor, and/or PPAR gamma, and/or ADRP, and/or CP-CYT, and/or alpha SMA, and/or other component(s) in the PTHrP signaling cascade, expression level(s) and/or activity can readily be determined according to a number of different methods, e.g., as described below. In particular, expression levels of one or more components of the pathway can be altered by changes in the copy number of the gene(s) encoding those components, and/or by changes in the transcription of the gene product (i.e. transcription of mRNA), and/or by changes in translation of the gene product (i.e. translation of the protein), and/or by post-translational modification(s) (e.g. protein folding, glycosylation, etc.). Thus useful assays of this invention include assaying for copy number, level of transcribed mRNA, level of translated protein, activity of translated protein, etc. Examples of such approaches are described below and while the approaches illustrated below are described with respect to PTHrP and/or the PTHrP receptor they are equally applicable to PPARgamma, ADRP, CP-CYT, alpha SMA, and/or other components of a PTHrP signaling pathway.

A) Nucleic-Acid Based Assays.

1) Target Molecules.

Changes in expression level(s) of PTHrP and/or the PTHrP receptor and/or a downstream component in the PTHrP signaling cascade can be detected by measuring changes in mRNA encoding such component(s) and/or a nucleic acid derived from the mRNA (e.g. reverse-transcribed cDNA, etc.). In order to measure the expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism, or from cells in culture. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation,* Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., (1989) *Molecular Cloning: A Laboratory Manual* (2nd ed.), Vols. 1–3, Cold Spring Harbor Laboratory, or *Current Protocols in Molecular Biology,* F. Ausubel et al., ed. Greene Publishing and Wiley-Interscience, New York (1987)).

Frequently, it is desirable to amplify the nucleic acid sample prior to assaying for expression level. Methods of amplifying nucleic acids are well known to those of skill in the art and include, but are not limited to polymerase chain reaction (PCR, see. e.g., Innis, et al., (1990) *PCR Protocols. A guide to Methods and Application.* Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In a particularly preferred embodiment, where it is desired to quantify the transcription level (and thereby expression) of PTHrP and/or the PTHrP receptor and/or a downstream component in the PTHrP signaling cascade in a sample, the nucleic acid sample is one in which the concentration of the mRNA transcript(s), or the concentration of the nucleic acids derived from the mRNA transcript(s), is proportional to the transcription level (and therefore expression level) of the gene(s) of interest. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the nucleic acid sample is the total mRNA or a total cDNA isolated and/or otherwise derived from a biological sample (e.g. a neurological cell or tissue). The nucleic acid may be isolated from the sample according to any of a number of methods well known to those of skill in the art as indicated above. 2) Hybridization-Based Assays.

Using the known sequences for components of the PTHrP and/or the PTHrP receptor and/or a downstream component in the PTHrP signaling cascade, detecting and/or quantifying the transcript(s) can be routinely accomplished using nucleic acid hybridization techniques (see, e.g., Sambrook et al. supra). For example, one method for evaluating the presence, absence, or quantity of reverse-transcribed cDNA involves a "Southern Blot". In a Southern Blot, the DNA (e.g., reverse-transcribed mRNA), typically fragmented and separated on an electrophoretic gel, is hybridized to a probe specific for subject nucleic acid(s) (or to a mutant thereof). Comparison of the intensity of the hybridization signal from the probe with a "control" probe (e.g. a probe for a "housekeeping gene") provides an estimate of the relative expression level of the target nucleic acid.

Alternatively, the mRNA of interest can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target PTHrP or PTHrPr mRNA. Appropriate controls (e.g. probes to housekeeping genes) provide a reference for evaluating relative expression level.

An alternative means for determining the expression level(s) of PTHrP and/or the PTHrP receptor and/or a downstream component in the PTHrP signaling cascade is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-Based Assays.

In another embodiment, amplification-based assays can be used to measure expression (transcription) level of PTHrP and/or the PTHrP receptor and/or a downstream component in the PTHrP signaling cascade. In such amplification-based assays, the target nucleic acid sequences (e.g. cAMP-dependent PKA, GSK-3beta, beta catenin, LEF-1, C/EBPalpha; PPARgamma, ADRP, leptin, etc.) act as template(s) in amplification reaction(s) (e.g. Polymerase Chain Reaction (PCR) or reverse-transcription PCR (RT-PCR)). In a quantitative amplification, the amount of amplification product will be proportional to the amount of template in the original sample. Comparison to appropriate (e.g. tissue or cells unexposed to the test agent) controls provides a measure of the target transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

One typical internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications,* Innis et al. (1990) Academic Press, Inc. N.Y. The known nucleic acid sequence(s) for PTHrP and/or the PTHrP receptor, components of the PTHrP signaling pathway are sufficient to enable one of skill to routinely select primers to amplify any portion of the gene(s).

4) Hybridization Formats and Optimization of Hybridization Conditions.

i) Array-Based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958, Pinkel et al. (1998) *Nature Genetics* 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high-density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high-density arrays is also described in U.S. Pat. Nos. 5,744,305, 5,800,992 and 5,445,934.

ii) Other Hybridization Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands that bind to labeled antibodies, fluorophores, chemi-luminescent agents, enzymes, and antibodies that can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

ii) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.).

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13: 105–114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

iv) Labeling and Detection of Nucleic Acids.

The probes used herein for detection of PTHrP and/or the PTHrP receptor and/or a downstream component in the PTHrP signaling cascade expression levels can be full length or less than the full length of the target nucleic acid. Shorter probes are empirically tested for specificity. Preferred probes are sufficiently long so as to specifically hybridize with the target nucleic acid(s) under stringent conditions. The preferred size range is from about 10, 15, or 20 bases to the length of the target mRNA, more preferably from about 30 bases to the length of the target mRNA, and most preferably from about 40 bases to the length of the target mRNA. The probes are typically labeled, with a detectable label as described above.

B) Detection of Expressed Protein

1) Assay Formats.

In addition to, or in alternative to, the detection of PTHrP and/or the PTHrP receptor and/or a downstream component in the PTHrP signaling cascade nucleic acid(s), alterations in expression of PTHrP and/or the PTHrP receptor and/or a downstream component in the PTHrP signaling cascade can be detected and/or quantified by detecting and/or quantifying the amount and/or activity of translated PTHrP polypeptides and/or the PTHrP receptor polypeptides and/or a downstream component in the PTHrP signaling cascade.

The expression of PTHrP and/or the PTHrP receptor and/or a downstream component in the PTHrP signaling cascade can be detected and quantified by any of a number of methods well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, the PTHrP and/or the PTHrP receptor and/or a downstream component in the PTHrP signaling cascade are detected/quantified in an electrophoretic protein separation (e.g., a 1- or 2-dimensional electrophoresis). Means of detecting proteins using electrophoretic techniques are well known to those of skill in the art (see generally, R. Scopes (1982) *Protein Purification,* Springer-Verlag, N.Y.; Deutscher, (1990) *Methods in Enzymology Vol. 182: Guide to Protein Purification,* Academic Press, Inc., N.Y.).

In another embodiment, Western blot (immunoblot) analysis is used to detect and quantify the presence of PTHrP and/or the PTHrP receptor and/or a downstream component in the PTHrP signaling cascade in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target member, e.g., polypeptide(s), and can be directly labeled or alternatively may be subsequently detected using labeled antibodies (e.g., labeled sheep anti-mouse antibodies) that specifically bind to a domain of the antibody.

In certain embodiments, the PTHrP and/or the PTHrP receptor and/or a downstream component in the PTHrP signaling cascade are detected using an immunoassay. As used herein, an immunoassay is an assay that utilizes an antibody to specifically bind to the analyte (e.g., the target polypeptide(s), such as PTHrP and/or the PTHrP receptor and/or a downstream component in the PTHrP signaling cascade). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) *Methods in Cell Biology Volume 37: Antibodies in Cell Biology,* Academic Press, Inc. New York; Stites & Terr (1991) *Basic and Clinical Immunology 7th Edition.*

Immunological binding assays (or immunoassays) typically utilize a "capture agent" to specifically bind to and often immobilize the analyte (e.g., PTHrP and/or the PTHrP receptor and/or a downstream component in the PTHrP signaling cascade). In certain embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401–1406, and Akerstrom (1985) *J. Immunol.,* 135: 2589–2542).

Typical immunoassays for detecting the target polypeptide(s), e.g., PTHrP and/or the PTHrP receptor and/or a downstream component in the PTHrP signaling cascade, are either competitive or noncompetitive. Noncompetitive immunoassays are assays in which the amount of captured analyte is directly measured. In one "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (e.g., PTHrP and/or the PTHrP receptor and/or a downstream component in the PTHrP signaling cascade) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one embodiment, the antibody is immobilized on a solid substrate. The amount of target polypeptide bound to the antibody may be determined either by measuring the amount of target polypeptide present in a polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind PTHrP and/or the PTHrP receptor and/or a downstream component in the PTHrP signaling cascade, either alone or in combination. In the case where the antibody that binds a PTHrP and/or the PTHrP receptor and/or a downstream component in the PTHrP signaling cascade is not labeled, a different detectable marker, for example, an enzyme-labeled antibody capable of binding to the monoclonal antibody which binds the PTHrP and/or the PTHrP receptor and/or a downstream component in the PTHrP signaling cascade, may be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds PTHrP and/or the PTHrP receptor and/or a downstream component in the PTHrP signaling cascade is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein can be routinely produced as described below.

2) Antibodies to PTHrP and/or the PTHrP Receptor and/or a Downstream Component in the PTHrP Signaling Cascade.

Either polyclonal or monoclonal antibodies can be used in the immunoassays of the invention described herein. Polyclonal antibodies are typically raised by multiple injections (e.g. subcutaneous or intramuscular injections) of substantially pure polypeptides or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for target polypeptides, such as PTHrP and/or the PTHrP receptor and/or a downstream component in the PTHrP signaling cascade If desired, the immunizing peptide can be coupled to a carrier protein by conjugation using techniques that are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are known in the art (see, e.g., *Methods of Enzymology, "Production of Antisera With Small Doses of Immunogen: Multiple Intradermal Injections"*, Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

In certain embodiments, however, the antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and $F(ab')_2$, and/or single-chain antibodies (e.g. scFv) which are capable of binding an epitopic determinant.

The general method used for production of hybridomas secreting mAbs is well known (Kohler and Milstein (1975) *Nature*, 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

Antibody fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552–554; Hoogenboom et al. (1991) Nucleic Acids Res. 19: 4133–4137).

Since the antibody fragments on the surface of the phage are functional, phage bearing antigen binding antibody fragments can be separated from non-binding phage by antigen affinity chromatography (McCafferty et al. (1990) Nature, 348: 552–554). Depending on the affinity of the antibody fragment, enrichment factors of 20 fold–1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) Nature, 348: 552–554). Thus even when enrichments are low (Marks et al. (1991) J. Mol. Biol. 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) J. Mol. Biol. 222: 581–597; Marks et al. (1993). Bio/Technology. 10: 779–783; Griffiths et al. (1993) EMBO J. 12: 725–734; Clackson et al. (1991) Nature. 352: 624–628). Antibodies have been produced against self proteins, including human thyroglobulin, immunoglobulin, tumor necrosis factor and CEA (Griffiths et al. (1993) EMBO J. 12: 725–734). It is also possible to isolate antibodies against cell surface antigens by selecting directly on intact cells. The antibody fragments are highly specific for the antigen used for selection and have affinities in the 1:M to 100 nM range (Marks et al. (1991) J. Mol. Biol. 222: 581–597; Griffiths et al. (1993) EMBO J. 12: 725–734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

C) Assays for Activity

Another aspect of the invention is a method of assaying a compound that modulates (e.g. activates/agonizes) PTHrP and/or the PTHrP receptor and/or a downstream component in the PTHrP signaling cascade, by selecting, as a test agent, a molecule or compound or composition that modulates the activity of PTHrP and/or the PTHrP receptor and/or a downstream component in the PTHrP signaling cascade. Preferably, the agent will agonize/upregulate the activity of PTHrP and/or the PTHrP receptor and/or a downstream component in the PTHrP signaling cascade.

The ability of a test compound to modulate (e.g. increase) the activity of PTHrP and/or the PTHrP receptor and/or a downstream component in the PTHrP signaling cascade cab be ascertained by measuring the activity of one or more components of the pathway. For example, responses such as downstream signaling or the ability of a member of the cascade to bind to its ligand substrate may be determined in in vitro assays. Cellular assays can be developed to monitor a modulation of second messenger production, changes in cellular metabolism, changes in intracellular location or effects on enzymatic activity. Immunoassays and nociceptive threshold assays, such as a withdrawal threshold assay, can also be used. These assays may be performed using conventional techniques developed for these purposes.

D) Assay Optimization.

The assays of this invention have immediate utility in screening for agents that modulate PTHrP and/or the PTHrP receptor and/or a downstream component in the PTHrP signaling cascade in a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred isolation conditions), antibody conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration.

Routine selection and optimization of assay formats is well known to those of ordinary skill in the art.

VIII. Pre-Screening for Agents that Modulate PTHrP and/or the PTHrP Receptor and/or a Component in the PTHrP Signaling Pathway In certain embodiments it is desired to pre-screen test agents for the ability to interact with (e.g. specifically bind to) a PTHrP and/or the PTHrP receptor and/or PPARgamma, and/or ADRP, and/or CP-CYT and/or alpha SMA and/or other components in in the PTHrP signaling pathway, and/or to a nucleic acid that encodes such a member. Specifically, binding test agents are likely to interact with and thereby alter PTHrP and/or the PTHrP receptor and/or a component in the PTHrP signaling pathway expression and/or activity. Thus, in some preferred embodiments, the test agent(s) are pre-screened for binding to PTHrP and/or the PTHrP receptor and/or other component in the PTHrP signaling cascade and/or to a nucleic acid encoding such a member before performing the more complex assays described above. While the prescreening methods are described below respect to PTHrP and/or the PTHrP receptor they are equally applicable to PPARgamma, ADRP, CP-CYT, alpha SMA, and/or other components of a PTHrP signaling pathway.

The test agent can be contacted directly to the PTHrP and/or the PTHrP receptor and/or a downstream component in the PTHrP signaling cascade, contacted to a cell containing the PTHrP and/or the PTHrP receptor and/or a downstream component in the PTHrP signaling cascade, and/or to a tissue comprising such cells (e.g. to a lung tissue), and/or contacted to an animal (e.g., a mammal) comprising.

Such pre-screening can readily be accomplished with simple binding assays. Means of assaying for specific binding or the binding affinity of a particular ligand for a nucleic acid and/or for a protein are well known to those of skill in the art. In preferred binding assays, the PTHrP and/or the PTHrP receptor and/or a downstream component in the PTHrP signaling cascade and/or the nucleic acid(s) encoding such a member, is immobilized and exposed to a test agent (which can be labeled), or alternatively, the test agent(s) are immobilized and exposed to PTHrP and/or the PTHrP receptor and/or a downstream component in the PTHrP signaling cascade (which can be labeled). The immobilized moiety is then washed to remove any unbound material and the bound test agent or bound PTHrP and/or the PTHrP receptor and/or a downstream component in the PTHrP signaling cascade is detected (e.g. by detection of a label attached to the bound molecule). The amount of immobilized label is proportional to the degree of binding between the PTHrP and/or the PTHrP receptor and/or a downstream component in the PTHrP signaling cascade and the test agent.

In certain embodiments, the detecting is via a method selected from the group consisting of capillary electrophoresis, a Western blot, mass spectroscopy, ELISA, immunochromatography, and immunohistochemistry.

IX. Scoring the Assay(s).

The assays of this invention are scored according to standard methods well known to those of skill in the art. The assays of this invention are typically scored as positive where there is a difference between the activity seen with the test agent present or where the test agent has been previously applied, and the (usually negative) control. In certain embodiments, the change is a statistically significant change, e.g. as determined using any statistical test suited for the data set provided (e.g. t-test, analysis of variance (ANOVA), semiparametric techniques, non-parametric techniques (e.g. Wilcoxon Mann-Whitney Test, Wilcoxon Signed Ranks Test, Sign Test, Kruskal-Wallis Test, etc.). Preferably the statistically significant change is significant at least at the 85%, more preferably at least at the 90%, still more preferably at least at the 95%, and most preferably at least at the 98% or 99% confidence level). In certain embodiments, the change is at least a 10% change, preferably at least a 20% change, more preferably at least a 50% change and most preferably at least a 90% change.

X. Agents for Screening: Combinatorial Libraries (e.g., Small Organic Molecules)

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487–493, Houghton et al. (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.,* 114: 9217–9218), analogous organic syntheses of small compound libraries (Chen et al. (1994) *J. Amer. Chem. Soc.,* 116: 2661), oligocarbamates (Cho, et al., (1993) *Science,* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) *C&EN*, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

XI. High Throughput Screening

Any of the assays described herein are amenable to high-throughput screening (HTS). Moreover, the cells utilized in the methods of this invention need not be contacted with a single test agent at a time. To the contrary, to facilitate high-throughput screening, a single cell may be contacted by at least two, preferably by at least 5, more preferably by at least 10, and most preferably by at least 20 test compounds. If the cell scores positive, it can be subsequently tested with a subset of the test agents until the agents having the activity are identified.

High throughput assays for hybridization assays, immunoassays, and for various reporter gene products are well known to those of skill in the art. For example, multi-well fluorimeters are commercially available (e.g., from Perkin-Elmer).

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

XII. Modulator Databases.

In certain embodiments, the agents that score positively in the assays described herein (e.g. show an ability to inhibit the expression or activity of a member of the PTHrP and/or the PTHrP receptor and/or a component in the PTHrP signaling pathway) can be entered into a database of putative and/or actual inhibitors of the PTHrP and/or the PTHrP receptor and/or a downstream component in the PTHrP signaling cascade. The term database refers to a means for recording and retrieving information. In certain embodiments the database also provides means for sorting and/or searching the stored information. The database can comprise any convenient media including, but not limited to, paper systems, card systems, mechanical systems, electronic systems, optical systems, magnetic systems or combinations thereof. Typical databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

XIII. Kits.

In another embodiment, this invention provides kits for the screening procedures and/or diagnostic procedures and/or treatment procedures described herein. Screening/diagnositic kits typically comprise one or more reagents that specifically bind to the target that is to be screened (e.g. PTHrP, PTHrP receptor, component of the PTHrP signaling pathway, etc.).

"Therapeutic" kits typically comprise a container containing one or more modulators of the PTHrP expression or activity and/or PTHrP receptor expression and/or activity and/or expression and/or activity of a component of the PTHrP signaling pathway (e.g., PPAR gamma, ADRP, PTHrPR, CP-CYT alpha SMA, etc.).

In addition, the kits optionally include labeling and/or instructional materials providing directions (i.e., protocols) for the practice of the methods or use of the "therapeutics" or "prophylactics" of this invention. Preferred instructional materials describe the use of one or agents of this invention to mitigate one or more symptoms of the pathologies described herein or to evaluate/diagnose one or more pathologies described herein, or to inhibit transdifferentiation of lipofibroblasts to myofibroblasts. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

The Role of Fibroblast Transdifferentiation in Pulmonary Alveolar Epithelial Growth, Differentiation and Repair Parathyroid Hormone-related Protein (PTHrP) expression is necessary for the differentiation the mesenchymal lipofibroblast, which induces epithelial type II (TII) cell differentiation, both of which are vital for alveolar homeostasis. Furthermore, PTHrP deficiency is associated with chronic lung disease (CLD) and failed alveolarization in the preterm baboon model of bronchopulmonary dysplasia. Experimentally, PTHrP deficiency causes the transdifferentiation of lipofibroblasts to myofibroblasts, characterized by loss of PTHrP receptor expression, decreased ADRP expression and triglyceride content, and upregulation of alpha SMA. PTHrP treatment of transdifferentiating lipofibroblasts reverses the down-regulation of the PTHrP receptor and up-regulation of ∀SMA, returning these cells to a lipofibroblast genotype. When TII alveolar cells are co-cultured with lipofibroblasts, they proliferate and differentiate based on expression of SP-B; in contrast to this, co-culture of TII cells with myofibroblasts fails to promote TII cell development, mimicking the failed alveolarization associated with CLD. Treatment of myofibroblasts with $PGJ_2$ stimulates ADRP expression, re-establishing the lipofibroblast phenotype. These $PGJ_2$-treated myofibroblasts now promote TII cell growth and differentiation, suggesting that failed alveolarization due to transdifferentiation may be reversible.

BACKGROUND

Studies of several models of lung development (mouse, rat, rabbit, sheep, primate) have shown that lung type II cells and fibroblasts elaborate and secrete soluble growth factors that determine the structure and function of the alveolar acinus (Sugahara et al. (1998) *Cell Tissue Res.* 291:295–303; Lebeche et al. (1999) *Mech. Dev.* 86:125–136; Adamson et al. (1991) *Exp. Lung Res.* 17:821–835), culminating in surfactant synthesis (Shannon et al. (2001) *Am. J. Respir. Cell Mol. Biol.* 24:235–244; Smith et al. (1989. *Am. J. Physiol.* 257:L174–L178). Therefore, we are particularly interested in epithelially-derived growth factors since mature fibroblasts produce paracrine factors that induce and maintain type II alveolar epithelial cell differentiation, thus forming a bi-directional paracrine loop (Torday et al. (1998) *Am. J. Med. Sci.* 316:205–208). Such differentiation (Sanchez-Esteban et al. (1998) *Am. J. Med. Sci.* 316:200–204) and homeostatic factors have been documented, and have been implicated in lung injury and repair mechanisms (Hastings et al. (2000) *Am. J. Physiol. Lung Cell Mol. Physiol.* 279: L194–200; Warshamana et al. (2001) *Exp. Mol. Pathol.* 71: 13–33).

During lung development, the episodic filling and emptying of the terminal air sacs with liquid plays an important role in molding the structure and function of the alveoli (Alcorn et al. (1977) *J. Anat.* 123:649–660; Moessinger et al. (1990) *J. Clin. Invest.* 86:1270–1277; Luks et al. (2001) *J. Pediatr. Surg.* 36:196–201). Although modest distension of the alveolar acinus promotes cell proliferation (Liu and Post (2000) *J. Appl. Physiol.* 89:2078–2084) and differentiation (Torday et al. (1998) *Am. J. Med. Sci.* 316:205–208), overdistension has the opposite effect (Sanchez-Esteban et al. (1998) *Am. J. Med. Sci.* 316:200–204; Dobbs and Gutierrez (2001) *Comp. Biochem. Physiol. A Mol. Integr. Physiol.* 129:261–266). It is evident that mechanical ventilation causes chronic lung disease in preterm infants (Coalson (1997) *Biol. Neonate* 71 (Suppl 1):35–38), and that overdistension per se can be causal (Albertine et al. (1999) *Am. J. Respir. Crit. Care Med.* 159:945–958; Fukunaga et al. (1998) *Am. J. Physiol.* 275:L567–573), but the mechanism for this physicochemical effect remains unknown. It is relatively easy to attribute neonatal lung injury to hyperoxia, given the extensive knowledge regarding the toxic effects of oxygen free radicals (Warner et al. (1998) *Am. J. Physiol.* 275:L110–117). On the other hand, besides the blunt trauma which can be caused overdistension, there is very limited information regarding molecular effects of overdistension on cell physiology (Gillette and Hess (2001) *Respir. Care* 46:130–148). However, the recognition that parathyroid hormone-related protein (PTHrP) is a stretch-sensitive gene expressed by the lung, and that it plays an essential role in normal lung development and homeostasis (Sanchez-Esteban et al. (1998) *Am. J. Med. Sci.* 316:200–204; Gao and Serrero (1999) *J Biol Chem.* 274:16825–16830) has opened new avenues for investigation of its potential role in lung pathophysiology due to barotrauma/volutrauma.

In this example, we have determined the impact of overdistension on an otherwise physiologic, stretch-dependent paracrine pathway PTHrP is a stretch-sensitive gene that is expressed by the developing lung epithelium. PTHrP binds to its G protein-coupled receptor on mesenchymal cells, stimulating both cAMP and $IP_3$ production (Rubin et al. (1994) *Biochim. Biophys. Acta* 1223: 91–100). PTHrP-dependent cAMP acts via Protein Kinase A to up-regulate a lipogenic genetic program, including Adipocyte Differentiation Related Protein, which mediates the physiologic accumulation of neutral lipids by these cells. PTHrP also stimulates the elaboration of leptin by lipofibroblasts, which, in turn, stimulates surfactant phospholipid and protein expression by neighboring type II pneumocytes (Torday et al. (1998) *Am. J. Med. Sci.* 316:205–208). Deletion of the PTHrP gene prevents the normal maturation of the developing lung, resulting in failure of both mesenchymal and epithelial cells to develop their characteristic phenotypes-triglyceride storage by lipofibroblasts and surfactant phospholipid synthesis by type II cells.

As for the clinical relevance of PTHrP, in a study of tracheal aspirates obtained from human newborns, it was found that PTHrP levels were significantly lower in those infants who developed respiratory distress syndrome (Speziale et al. (1998) *Pediatr. Res.* 43:660–665), consistent with its hypothetical role in normal alveolar lung development (6,7,21,23–25). Our studies of PTHrP in tracheal aspirates predicts BPD.

Pulmonary lipofibroblasts are similar to hepatic stellate cells of the liver, whose phenotype is characterized by neutral lipid stores (Ito and Shibasaki (1968) *Arch. Histol. Jpn.* 29:137–192). When these cells are propagated in culture, they transdifferentiate into myofibroblasts, losing these lipid stores (Galli et al. (2000) *Hepatology* 31:101–108), while gaining the expression of alpha smooth muscle actin, which typifies liver fibrosis (Shimizu et al. (1999) *Life Sci.* 64:2081–2088). Since myofibroblasts are also typical of lung fibrosis (Lee et al. (1997) *Am J Physiol.* 273:G1094–1100; Gauldie et al. (1999) *Curr. Top. Pathol.* 93:35–45) and bronchopulmonary dysplasia (Toti et al. (1997) *Pediatr. Pulmonol.* 24:22–28), we hypothesize that damage to type II cells down-regulates PTHrP expression (Sanchez-Esteban et al. (1998) *Am. J. Med. Sci.* 316:200–204), leading to failed differentiation of lipofibroblasts, which subsequently transdifferentiate into myofibroblasts. We further speculate that, based on previous studies (Post et al. (1984) *Exp. Lung Res.* 7:53–65), lipofibroblasts will promote lung epithelial cell growth and differentiation, but that myofibroblasts will not, providing a mechanism for failed alveolarization in mechanically-ventilated preterm infants (Husain et al. (1998) *Hum. Pathol.* 29:710–717).

Methods

Reagents

PTHrP (1-34) and PTHrP (7-34) amide were obtained from Bachem, Torrance, Calif.

Animals

Time-mated Sprague-Dawley rats (E0=day of mating) were obtained from Charles River Breeders (Holister, Calif.). These experiments were conducted in accordance with the NIH Guide for the Care and Use of Laboratory Animals.

Cell Culture

These methods have been used extensively in our laboratory (Rubin et al. (1994) Biochim. Biophys. Acta 1223: 91–100; Torday et al. (1995) Biochim. Biophys. Acta 1254:198–206). Three to five dams were routinely used per preparation. The dams were killed with an overdose of pentobarbital (100 mg/ml, i.p.) and the pups were removed from the uterus by laparotomy and kept on ice. The lungs were removed en bloc in a laminar flow hood using sterile technique and put into ice-cold sterile Hanks' balanced salt solution without calcium or magnesium. The solution was decanted and 5 volumes of 0.05% trypsin (Worthington) were added to the lung preparation.

The lungs were dissociated in a 37° C. water bath using a Teflon™ stirring bar to physically disrupt the tissue. When the tissue was completely dispersed into a unicellular suspension (approx. 20 min.), the cells were spun down at 500×g for 10 min at room temperature in a 50 ml polystyrene centrifuge tube. The supernatant was decanted, and the cell pellet was re-suspended in minimal essential medium (MEM, GIBCO) containing 10% fetal bovine serum to yield a mixed cell suspension of approximately $3 \times 10^8$ cells, as determined by Coulter Particle Counter (Hayaleah, Fla.). The cell suspension was added to 75-cm² culture flasks (Corning Glass Works, Corning, N.Y.) for 30–60 min at 37° C. in a $CO_2$ incubator to allow for differential adherence of the fibroblasts (Smith and Giroud (1975) Can. J. Physiol. Pharmacol. 53:1037–1041). The fibroblasts were maintained in MEM/0.1% fatty acid-free bovine serum albumin until further processing.

Triglyceride Assay

The method used was described in (Torday et al. (1995) Biochim. Biophys. Acta 1254:198–206; Nunez and Torday (1995) J. Nutr. 125(Suppl): 1639S–1644S)

Isolation of Total Cellular RNA

Total cellular RNA was isolated using previously described methods in our laboratory. Cells were lysed directly by vortexing in 0.2 mL lysis solution [2M guanidium isothiocyanate, 12.5 mM sodium citrate (pH 7.0), 0.25% sarkosyl, 50 mM 2-mercaptoethanol, and 50% (vol/vol) water-saturated phenol]. Chloroform-isoamyl alcohol (49:1, vol/vol) was added to each sample and the mixture was vortexed and cooled on ice. After centrifugation at 10,000×g for 20 min at 4° C., RNA in the aq. phase was precipitated in EtOH at –20° C. The RNA was pelleted at 10,000×g for 20 min at 4° C., RNA in the aq. Phase was precipitated in EtOH at –20° C. After re-extraction in P:IC and EtOH precipitation, samples were resuspended in DEPC-treated water and quantitated by absorbance at 260 nm.

Propagation of Myofibroblasts

E21 fetal rat lung fibroblasts were serially passaged. Cells at passage 10 (P10) are devoid of PTHrP receptor, ADRP and leptin expression, but express both ∀ smooth muscle actin and desmin, which are positive markers for myofibroblasts.

Competitive RT-PCR

The appropriate cDNA fragments were amplified using 400 ng of total RNA from lung tissues or cell cultures, avian myeloblastosis virus reverse transcriptase and random hexamers and deoxyribonucleotides. The reactions were run at 42° C. for 75 min and terminated by heating at 95° C. for 5 min. Co-amplification with GAPDH cDNA was used as an internal standard. PCR was initiated by Taq DNA polymerase and allowed to proceed for 30 cycles with an annealing temperature of 50° C. We used a commercially available primer and competimer™ for 18S ribosomal RNA (Ambion, Austin, Tex.) to control for PCR reaction and aliquot loading variability across samples. The following primers were used in the RT-PCR assay: rat SP-B (sense, 5'-TAC ACA GTA CTT CTA CTA GAT G (SEQ ID NO:2); antisense, 3'-ATA GGC TGT TCA CTG GTG TTC C (SEQ ID NO:3)) human leptin (sense, 5'-CCTATCTTTTCTATGTCCAAGC (SEQ ID NO:4); antisense, 3'-GTG AGG ATC TGT TGG TAG ACT G (SEQ ID NO:5)); human leptin receptor designed to detect all of the known isoforms (sense, 5'-TAC TTT GGA AGC CCC TGA TG (SEQ ID NO:6); antisense, 3'-AAG CAC TGA GTG ACT GCA CG (SEQ ID NO:7)); rat leptin (sense, 5'-TTA TGT TCA AGC AGT GCC TAT C (SEQ ID NO:8); antisense, 3'-CAT CCA ACT GTT GAA GAA TGT C (SEQ ID NO:9)); rat leptin receptor (sense, 5'-ACC TTC AGT TCC AGA TTC GA (SEQ ID NO:10); antisense, 3'-TGA GAT TGG TCT GAT TTC CC (SEQ ID NO:11)); rat ADRP (sense, 5'-GAA CAA AGG TCC TCA TTA TGG TCA TTC ACA GCT CAC TTA TGG TCG TGC (SEQ ID NO:12); antisense, 3'-GCA CGA CCA TAA GTG AGC TGT GAA TGA CCA TAA TGA GGA CCT TTG TTC (SEQ ID NO:13)). The identities of all RT-PCR products were confirmed by Southern blotting. mRNA expression was quantitated by densitometry (Eagle Eye, Stratagene).

Protein Determination

Protein determination was made using the Bradford dye binding method (Nunez and Torday (1995) J. Nutr. 125 (Suppl): 1639S–1644S).

PTHrP ELISA

The enzyme-linked immunosorbent assay for PTHrP 1-86 was a gift from Dr. Delbert Fisher, Quest Diagnostics, San Juan Capistrano, Calif. The sensitivity of the assay is 0.3 pg/ml and it is 100% specific, showing no cross-reactivity with other isoforms of PTHrP.

Statistical Analyses

Analysis of Variance was used to compare experimental data. The null hypothesis was rejected when $p<0.05$ was not obtained.

Results

The present series of experiments was designed to elucidate how barotrauma/volutrauma may interrupt lung alveolarization in preterm animals. We have focused on the role of PTHrP because it is a stretch-regulated gene expressed by alveolar epithelial cells that affects the paracrine mechanism (s) regulating alveolar growth and differentiation.

Figure 5:
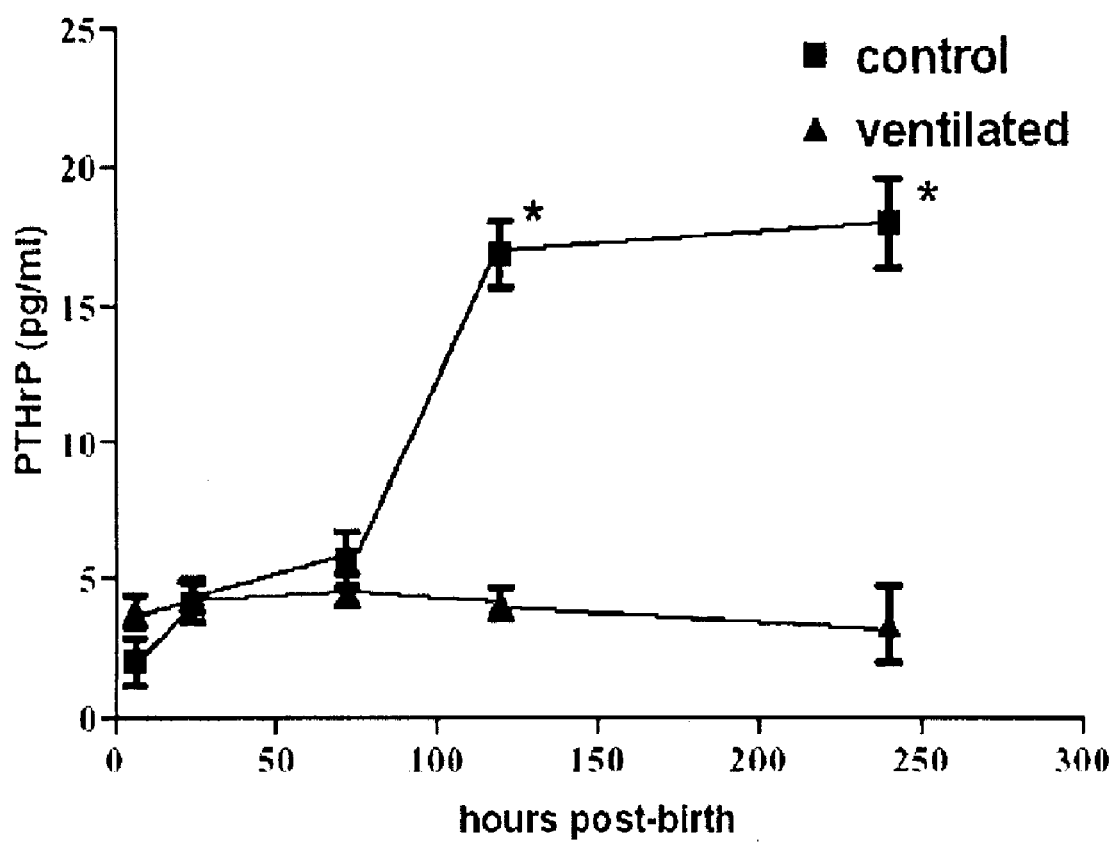
FIG. 5 illustrates the effect of mechanical ventilation on PTHrP Production in vivo. Lung lavage was collected from control and mechanically ventilated 140 day old preterm baboons and assayed for PTHrP. Data represent the mean±SD, n=3.*, $p<0.0001$ by Analysis of Variance.
Figure 6:
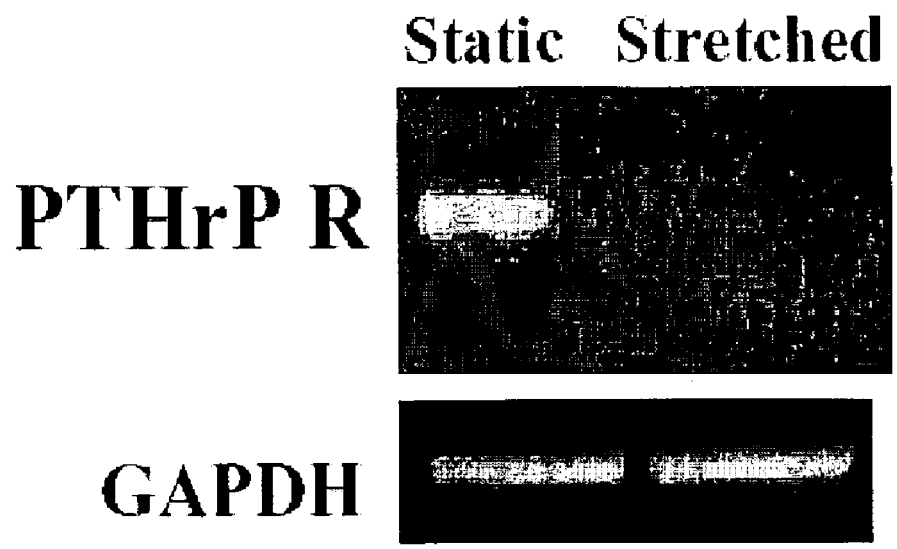
FIG. 6 illustrates the effect of stretch on PTHrP expression by type II cells. E21 fetal rat lung type II cells attached to a collagen coated silastic membrane were stretched (12–15% radial elongation, 50 cycles/min for 15 min/h×15 h). At the end of the treatment, the cells were analyzed for PTHrP mRNA expression by Competitive RT-PCR; mRNA in stretched cells was compared with static cells which were cultured under the same conditions. RNA loading was normalized using GAPDH. Representative gel, n=3.

In initial studies, we found that PTHrP levels in tracheal aspirates from mechanically ventilated baboons exposed to mechanical ventilation remains low, whereas in control animals subjected to little or no mechanical ventilation the levels of PTHrP increased more than 10-fold over the course of the first 10 days of postnatal life (FIG. 5). To determine why mechanical ventilation leads to decreased PTHrP expression, we overdistended cultured alveolar epithelial cells derived from term (day 21) fetal rats and observed down-regulation of PTHrP mRNA expression (FIG. 6).

Figure 7:
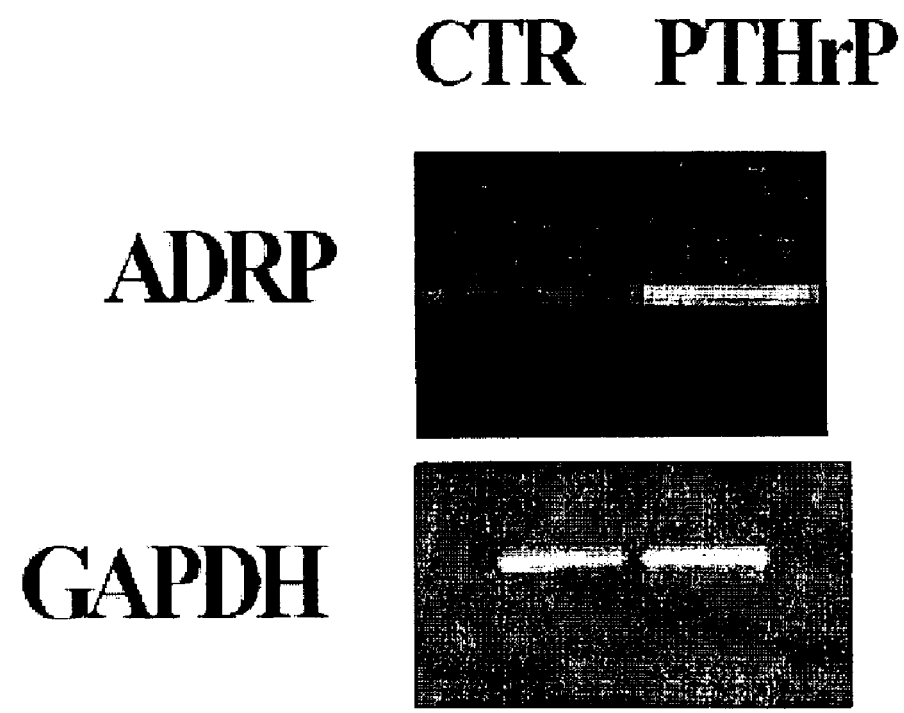
FIG. 7 shows that PTHrP up-regulates ADRP expression. E19 fetal rat lung fibroblasts were treated with 0.5:M PTHrP for 15 hours. At the end of the incubation period, the cells were analyzed for ADRP mRNA expression by Competitive RT-PCR. RNA loading was normalized using GAPDH. Representative gel, n=3.
Figure 8:
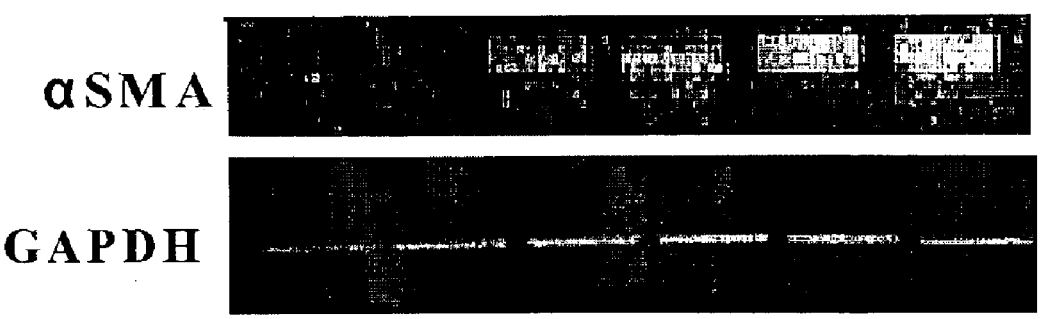
FIG. 8 shows that transdifferentiating lipofibroblasts lose triglyceride content. E21 fetal rat lung lipofibroblasts cultured for up to 10 passages in the absence of PTHrP were assayed for their triglyceride content. Triglyceride levels decreased progressively, reaching baseline levels by passage 5. Bars represent the means±SD, n=3–5 experiments. *,$p<0.05$; **,$p<0.01$ by Analysis of Variance.
Figure 9:
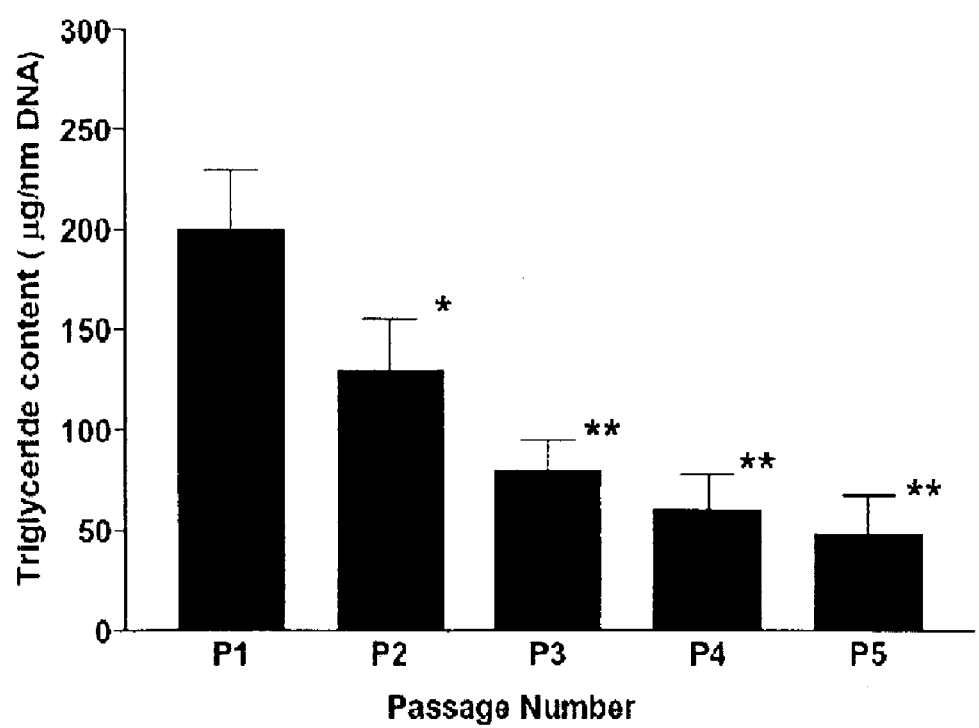
FIG. 9 illustrates down-regulation of PTHrP receptor mRNA expression in serially cultured LIF. E21 fetal rat lung lipofibroblasts were serially passaged. At each passage, when the cells were confluent they were analyzed for PTHrP receptor mRNA expression. RNA loading was normalized to GAPDH. Representative gel, n=3.

Based on this observation, subsequent experiments were designed to determine how PTHrP deprivation affects the development of the alveolar acinus, particularly its stimulation of the lipofibroblast phenotype. PTHrP stimulates lung mesenchymal cell differentiation into lipofibroblasts, as shown in FIG. 7, by inducing ADRP expression by fetal rat lung fibroblasts (similar results have been obtained by treating fetal baboon lung fibroblasts with PTHrP). ADRP expression is necessary for the uptake and accumulation of neutral lipids by these cells (Gao and Serrero (1999) *J. Biol. Chem.* 274:16825–16830). In contrast to this stimulatory effect of PTHrP on fibroblast maturation, when mature lipofibroblasts are cultured in the absence of PTHrP they lose their lipofibroblast phenotype upon serial culture, typified by a decrease in triglyceride content (FIG. 8). Mechanistically, this transdifferentiation process is associated with the down-regulation of PTHrP receptor mRNA (FIG. 8) beginning at the $4^{th}$–$5^{th}$ passage, and progressively decreasing over subsequent passages. The decrease in PTHrP receptor expression is followed subsequently by down-regulation of ADRP and leptin expression (data not shown), both of which are up-regulated by PTHrP, and are functionally significant to the lipofibroblast phenotype (Ito and Shibasaki (1968) *Arch. Histol. Jpn.* 29:137–192). As a result of the down-regulation of the PTHrP receptor, exogenous PTHrP is no longer able to stimulate ADRP or leptin expression.

Figure 10:
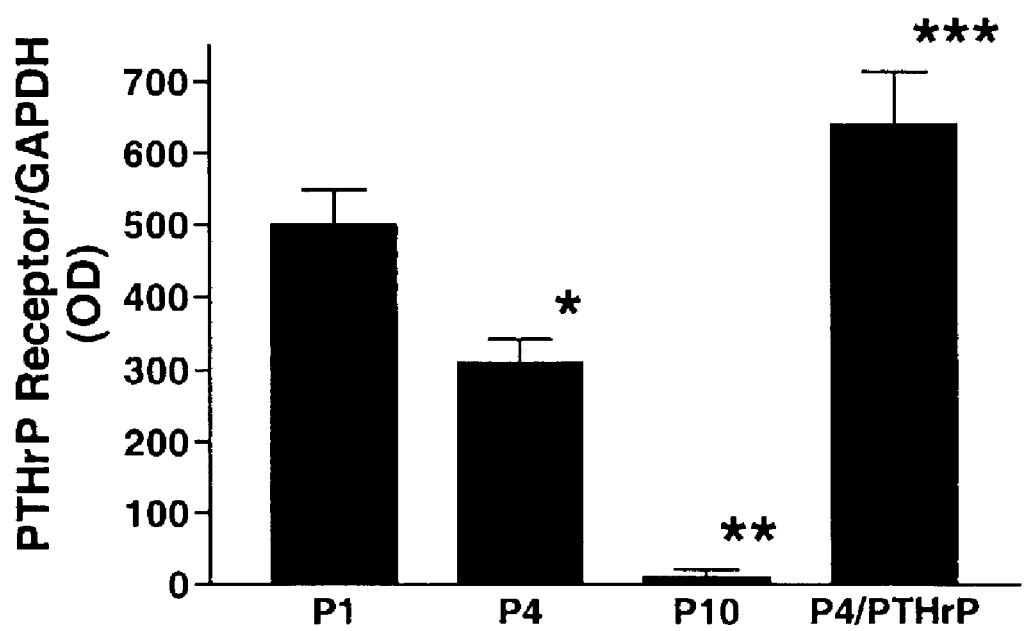
FIG. 10 illustrates upregulation of α-SMA expression by serially cultured LIF. E21 fetal rat lung lipofibroblasts were serially passaged. At each passage, when the cells reached confluence they were analyzed for PTHrP receptor mRNA expression. RNA loading was normalized to GAPDH. Representative gel, n=3.
Figure 11:
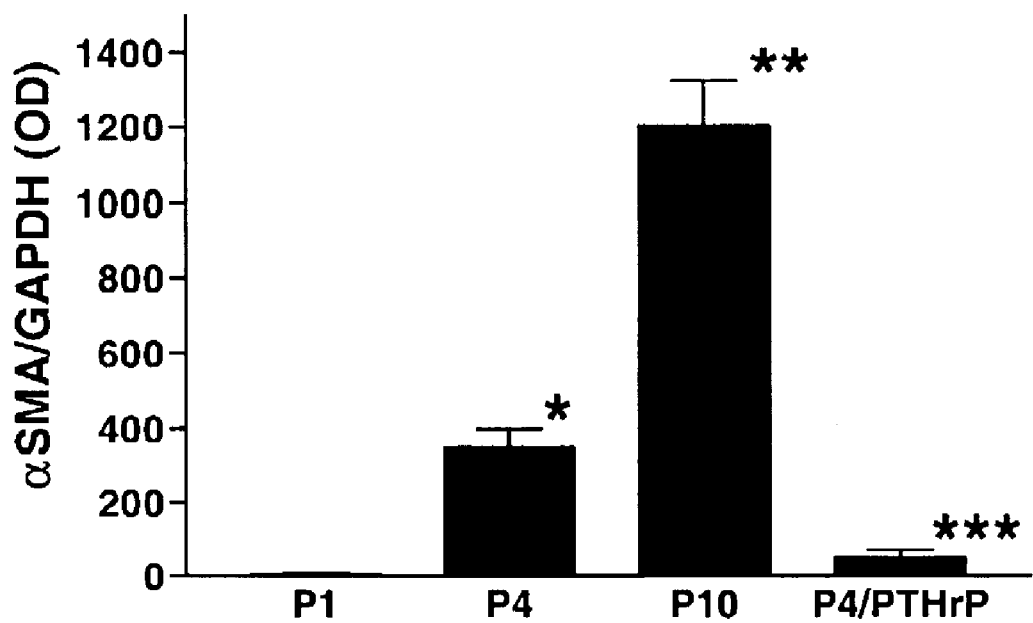
FIG. 11 shows the effect of PTHrP on PTHrP receptor expression by LIFs. LIFs were serially passaged (P1–P10). PTHrP Receptor expression was determined by Competitive RT-PCR normalized with GAPDH. At P4 the cells were treated with PTHrP (0.5:M) for 24 h. n=6, P1 v P4, P10, *$p<0.001$, $p<0.0001$; P4 v P4/PTHrP, *$p<0.01$ by Analysis of Variance.
Figure 12:
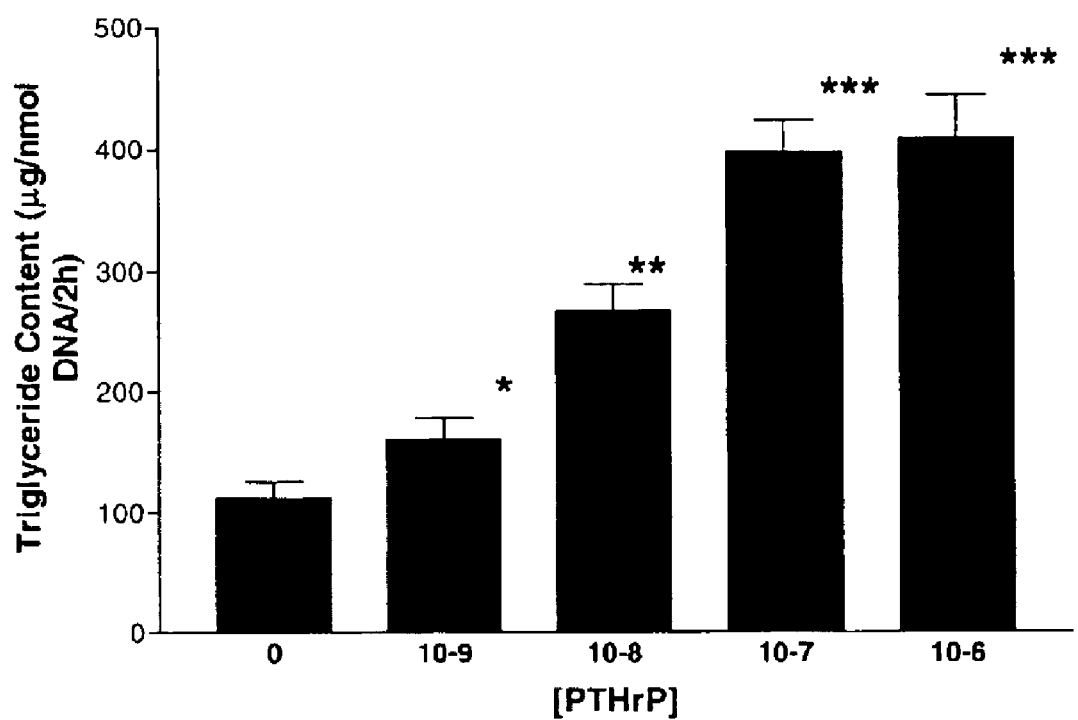
FIG. 12. shows αSMA expression by serially passaged LIFs. LIFs were serially passaged (P1–P10) and αSMA expression was determined by competitive RT-PCR normalized to GAPDH. At P4 the cells were treated with PTHrP (P4/PTHrP, 0.5:M/24 h). n=6, P1 v P4, P10, *$p<0.001$, $p<0.0001$; P4 v P4/PTHrP, *$p<0.01$ by Analysis of Variance.

During the course of lipofibroblast transdifferentiation, these cells begin expressing ∀ smooth muscle actin (alpha SMA) beginning at passage 4, increasing progressively over sequential passages; alpha SMA is indicative of the transdifferentiation of lipofibroblasts into myofibroblasts (Shimizu et al. (1999) *Life Sci.* 64:2081–2088). To further test the role of PTHrP deprivation in the transdifferentiation of lipofibroblasts to myofibroblasts, serially passaged lipofibroblasts were treated with PTHrP at Passage 4 for 24 hours and we observed an increase in PTHrP expression up to a level comparable to that of P1s, indicating "rescue" of the lipofibroblast phenotype (FIG. 10). In further support of the hypothesized role of PTHrP deprivation on the expression of the myofibroblast phenotype, 24 hour treatment of P4 lipofibroblasts with PTHrP decreased alpha SMA expression down to levels comparable to those observed for P1s, again indicating restoration of the lipofibroblast phenotype by PTHrP. The net effect of PTHrP exposure, therefore, was the re-establishment of the patterns of PTHrP receptor and alpha SMA expression by primary lipofibroblasts. We observed similar effects of PTHrP treatment on ADRP and leptin expression, and on the triglyceride content of P4 lipofibroblasts (data not shown).

Figure 13:
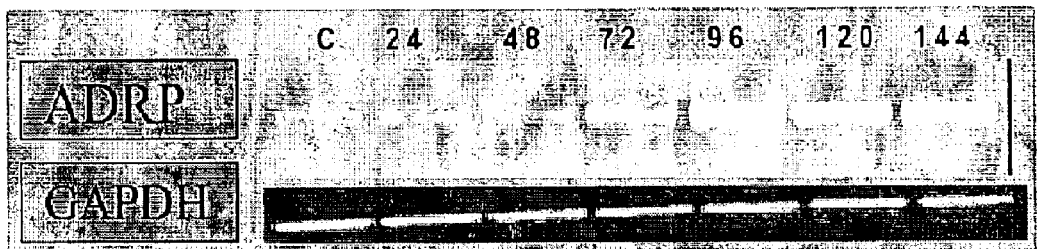
FIG. 13 illustrates the effect of $PGJ_2$ on PTHrP receptor expression by myofibroblasts. Myofibroblasts (P10s) were grown in culture in the presence of $PGJ_2$ (30:M) for up to 144 hours and were analyzed for PTHrP receptor expression at the indicated time points. PTHrP receptor expression in control cells remained low or undetectable. Representative gel, n=3
Figure 14A:
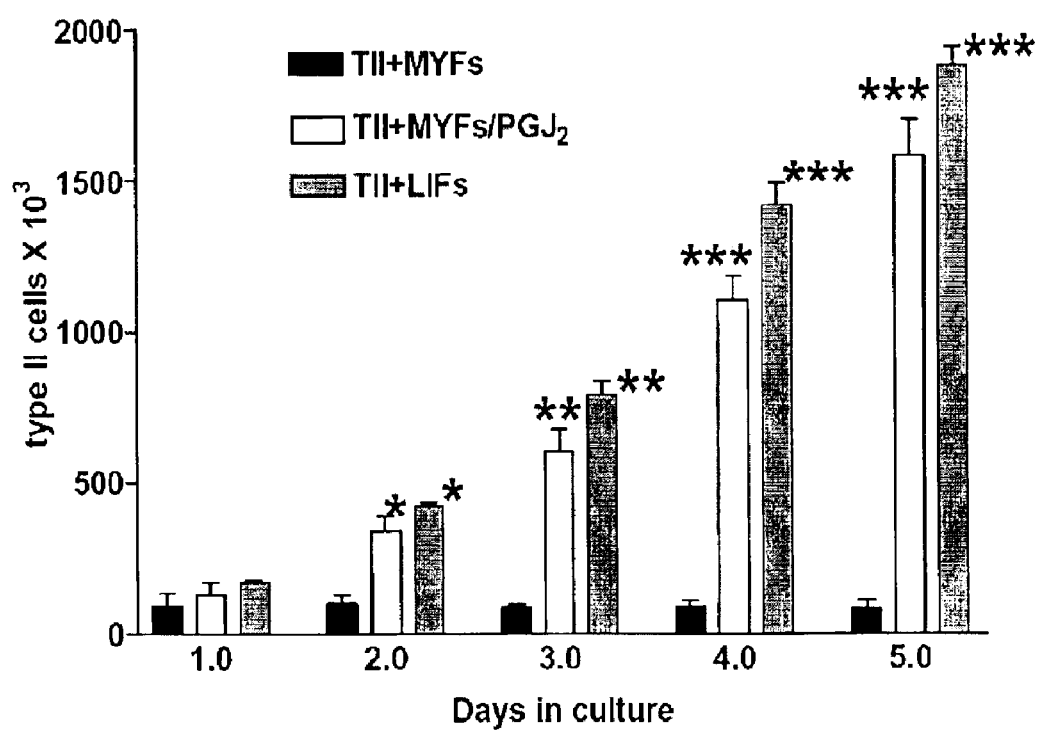
FIGS. 14A and 14B show the effect of lipofibroblasts and myofibroblasts on fetal rat type II cell growth and differentiation. Fetal type II cells were co-cultured with lipofibroblasts, myofibroblasts or myofibroblasts pretreated with $PGJ_2$. Cell growth was determined by cell count and differentiation was determined by RT-PCR for Surfactant Protein B. Note that in the presence of lipofibroblasts or myofibroblasts treated with $PGJ_2$ that type II cells grow (see Figure on left) and differentiate (Figure on right) with time in culture. Myofibroblasts failed to support type II cell growth or differentiation. Day 1 v subsequent day in culture, *, $p<0.05$; ; $p<0.01$; *, $p<0.001$ by Analysis of Variance.
Figure 14B:
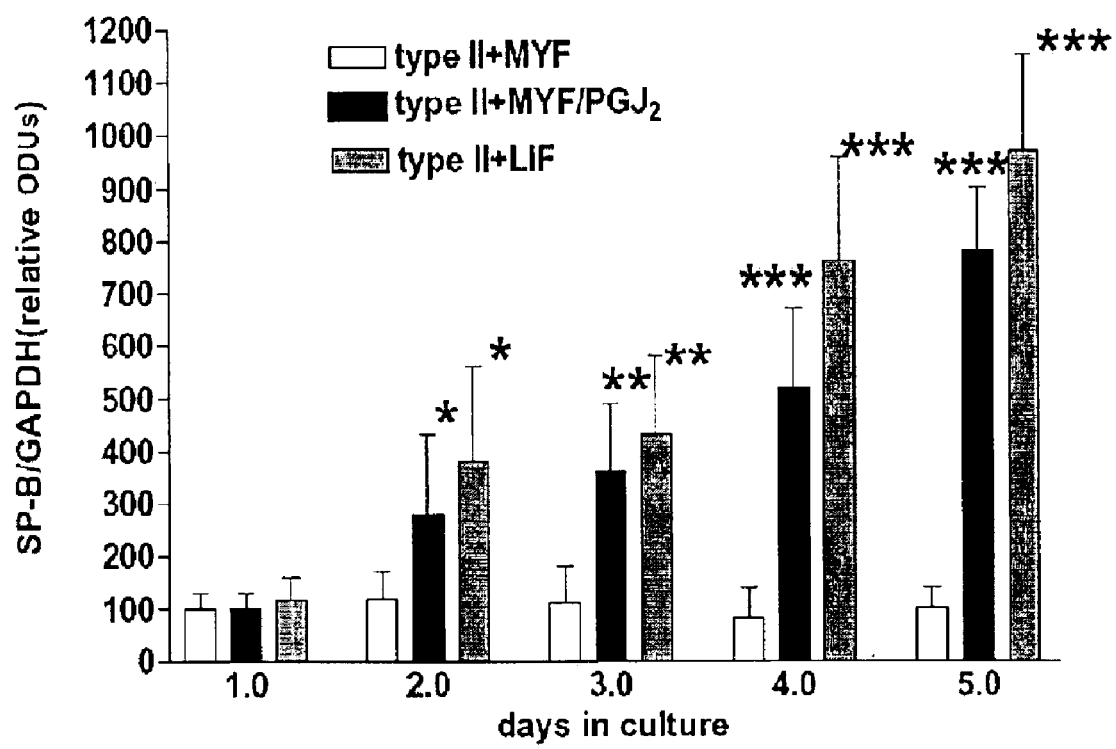

In order to link the process of fibroblast transdifferentiation to alveolarization, we recombined day 19 fetal rat lung type II cells with either P1 lipofibroblasts, P10 myofibroblasts, or P10 myofibroblasts pretreated with $PGJ_2$; $PGJ_2$ induces the transdifferentiation of myofibroblasts to lipofibroblasts (Hu et al. (1995) *Proc. Natl. Acad. Sci. USA* 92:9856–9860). For example, treatment of P10 myofibroblasts with $PGJ_2$ (FIG. 13) increased the expression of ADRP; similar effects on the expression of ADRP and leptin, and on triglyceride content were observed (data not shown). As can be seen in FIG. 14A, co-culture of E21 type II cells with E21 lipofibroblasts led to an 18–20 fold increase in the number of type II cells over the 5 day culture period. Type II cells co-cultured with myofibroblasts failed to show an increase in type II cell number; in marked contrast to the failure of myofibroblasts to support type II cell proliferation, $PGJ_2$ pre-treated myofibroblasts had an effect on type II cell proliferation comparable to that of primary lipofibroblasts. When the type II cells from this experiment were analyzed for their effect fibroblast co-culture on type II cell differentiation (FIG. 14B), a 7–8 fold increase in Surfactant Protein-B expression by type II cells cultivated with lipofibroblasts was observed; type II cells co-cultured with P10 myofibroblasts showed no increase in Surfactant Protein-B mRNA expression. However, those type II cells co-cultured with $PGJ_2$-treated P10 myofibroblasts had a stimulatory effect on Surfactant Protein-B expression by type II cells comparable to that by lipofibroblasts.

Discussion

It has long been recognized that physical force plays an important role in determining normal lung growth and differentiation (Liu and Post (2000) *J. Appl. Physiol.* 89:2078–2084), as well as in adult lung function (Faridy et al. (1966) *J Appl Physiol.* 21:1453–1462; Wyszogrodski et al. (1975) *Chest* 67(2 Suppl): 15S–16S) and injury repair (O'Reilly et al. (1997) *Microsc. Res. Tech.* 38: 473–479). Up until now, little progress has been made in elucidating the nature of this mechanism. However, we have recently discovered that PTHrP is a stretch-sensitive product of the alveolar type II cell (Torday et al. (1998) *Am. J. Med. Sci.* 316:205–208) that is necessary for epithelio-mesenchymal interactions in developing, and functioning lung. These empiric observations have provided us with an opportunity to determine how physical force affects both normal and abnormal lung development (Torday et al. (1998) *Am. J. Med. Sci.* 316:205–208; Sanchez-Esteban et al. (1998) *Am. J. Med. Sci.* 316:200–204). It is only recently that investigators have begun considering cell-cell interactions in exploring the etiology of chronic lung disease, which is characterized by proliferation of myofibroblasts, whether in BPD (Redington (2000) *Clin. Exp. Allergy* 30 (Suppl 1):42–45), asthma (Holgate (2000) *Clin. Exp. Allergy* 30 (Suppl 1):37–41) or emphysema (O'Reilly et al. (1997) *Microsc. Res. Tech.* 38: 473–479). The molecular breakdown in cell-cell signaling leading to phenotypic changes in the interstitium appears to be at the center of all of these chronic lung diseases (Sheppard (2001) *J. Clin. Invest.* 107:1501–1502), yet the underlying pathobiology has remained elusive (Selman et al. (2001) *Ann. Intern. Med.* 134:136–151).

In the present series of experiments, we have provided a mechanistic link between barotrauma and failed epithelialization of alveoli, mediated by soluble factors: overdistension of alveolar epithelial cells caused loss of PTHrP mRNA expression, leading to transdifferentiation of interstitial lipofibroblasts to myofibroblasts, which in turn failed to sustain the growth and differentiation of type II epithelial cells. The cause of newborn chronic lung disease, or bronchopulmonary dysplasia has been difficult to ascertain because there are a number of pathophysiologic variables involved, ranging from prematurity (Jobe (1999) *Pediatr. Res.* 46:641–643), to oxygen toxicity (Welty (2001) *J. Nutr.* 131: 947S–950S), and infection (Lyon (2000) *Eur. J. Pediatr.* 159:798–802), as well as the strain effects of mechanical ventilation (Albertine et al. (1999) *Am. J. Respir. Crit. Care Med.* 159:945–958). It is only recently that investigators have focused on the detrimental effects of overdistension itself, driven by the observation in an elegant preterm baboon model (Coalson (1997) *Biol. Neonate.* 71 (Suppl 1):35–38), as well as in preclinical (Albertine et al. (1999) *Am. J. Respir. Crit. Care Med.* 159:945–958) and clinical observations (34, 53) that all point to overdistension as a causal factor.

PTHrP is expressed by developing lung (Rubin et al. (1994) *Biochim. Biophys. Acta* 1223: 91–100; Campos et al. (1991) *Cancer Res.* 51:6351–6357), is up-regulated by fluid distension in utero (Torday et al. (1998) *Am. J. Med. Sci.* 316:205–208), and down-regulated in respiratory distress syndrome (Speziale et al. (1998) *Pediatr. Res.* 43:660–665), consistent with its role in alveolarization and surfactant production. PTHrP is also expressed by adult type II cells, where it appears to play a functional role in re-epithelialization of the alveolus (Hastings et al. (2000) *Am. J. Physiol. Lung Cell Mol. Physiol.* 279: L194–200). After injury, the alveolar epithelium must initiate a wound healing process in order to restore its barrier function. The effective reepithelialization of the alveolar surface by type II pneumocytes is critical to reestablishing homeostasis (Selman et al. (2001) *Ann. Intern. Med.* 134:136–151). PTHrP signals to neighboring mesenchymal cells through its 7 membrane spanning, G-protein dependent receptor (Hoare and Usdin (2001) *Curr. Pharm. Des.* 7:689–713), stimulating a cAMP-dependent PKA pathway which induces the lipofibroblast phenotype, characterized by expression of such lipogenic features as fatty acid synthetase (Torday et al. (1998) *Am. J. Med. Sci.* 316:205–208), lipoprotein lipase (Id.), ADRP (Rubin et al. (1994) *Biochim. Biophys. Acta* 1223: 91–100), leptin, and triglyceride uptake. The last two features of the lipofibroblast are of functional significance because they provide both cytoprotection against oxygen free-radicals (Dennery et al. (1990) *Am. J. Respir. Cell Mol. Biol.* 3:137–144; Spitz et al. (1992) *Pediatr. Res.* 32:366–372; Torday et al. (2001) *Pediatr. Res.* 49:843–849), and neutral lipid substrate for surfactant phospholipid synthesis at the time of birth (Husain et al. (1998) *Hum. Pathol.* 29:710–717), respectively, and may play a similar role in adult lung injury (Brooks (1971) *Lab. Invest.* 25:536–545), since the lipofibroblast is prominent during lung injury and repair.

Failure to express PTHrP results in lung immaturity and death at the time of birth associated with surfactant phospholipid deficiency, consistent with the necessity to express PTHrP during normal lung development. Furthermore, infants who develop RDS are relatively PTHrP-deficient (Speziale et al. (1998) *Pediatr. Res.* 43:660–665), supporting the role of PTHrP in alveolar development and pulmonary surfactant synthesis. In experiments designed to test the hypothesized role of PTHrP in alveolar homeostasis, we have observed that overdistension of the adult rat lung results in down-regulation of the PTHrP signaling pathway, resulting in decreased surfactant expression, extending the role of PTHrP in alveolar homeostasis to adult lung barotrauma.

Example 2

Hyperoxia Enhances Pulmonary Lipofibroblast-to-Myofibroblast Transdifferentiation Bronchopulmonary dysplasia (BPD) remains a major cause of morbidity and mortality in premature infants, and despite many advances its pathophysiology remains incompletely understood. Exposure of the premature lung to hyperoxia is commonly implicated in its pathogenesis. However, the exact link between hyperoxia and BPD, and particularly its role in the generation of myofibroblasts, the signature cell type of lung fibrosis, is not clear. There is increasing evidence that lipid interstitial fibroblasts play an important role in the injury-repair mechanisms in various organ systems. In this study we demonstrate that exposure to hyperoxia enhances the transdifferentiation of pulmonary lipofibroblasts to myofibroblast. Fetal rat lung fibroblasts (FRLF) from e (embryonic, term=22) 18 and e21 were studied. After initial culture in MEM and 10% FBS in 21% $O_2$+5% $CO_2$ at 37° C., FRLFs were maintained in MEM and 10% FBS at 37° C. under control conditions (21% $O_2$) and under experimental conditions (24 h exposure to 95% $O_2$+5% $CO_2$) at passage (P) 1 and P5. At each passage, cells were allowed to grow and attach to 100 cm² culture dishes in 21% $O_2$ before being subjected to the experimental conditions. Passage 1 and 5 cells were analyzed for the presence and absence of well characterized lipogenic and myogenic markers based on semi-quantitative competitive RT-PCR [for PTHrPR (Parathyroid Hormone related Protein Receptor), ADRP (Adipose Differentiation Related Protein), and α-SMA (Smooth Muscle Actin), triglyceride up take, and leptin assay. We observed that with passaging and maintaining cells in 21% $O_2$ resulted in a significant decrease in lipogenic marker from P1 to P5, spontaneously. This decrease was greater for e18 vs. e21 FRLF. However, exposing cells in 95% $O_2$ enhanced the loss of lipogenic markers and gain of myogenic marker from P1 to P5 in comparison to cells maintained in 21% $O_2$. The changes were also greater for e18 vs. e21 lipofibroblasts. The changes in mRNA expressions were also accompanied by changes in triglyceride up take and leptin secretion. These results suggest that exposure to hyperoxia (95% $O_2$) accelerates the transdifferentiation of pulmonary lipofibroblasts to myofibroblasts. Hyperoxia-induced transdifferentiation was at least partially attenuated with selective antioxidant and prostaglandin J2 pretreatments. We believe this lipo-to-myofibroblast transdifferentiation is an important mechanism for hyperoxic lung injury and is a key element in the pathophysiology of BPD. Induction of adipogenic transcription factors may not only prevent but, in fact, may reverse the myogenic fibroblast phenotype to the adipogenic fibroblast phenotype.

Introduction

Bronchopulmonary dysplasia (BPD) occurs primarily in premature infants who require supplemental oxygen and ventilatory support (1. Stevenson et al.(1998) *Am J Obstet Gynecol.* 179, 1632–1639; Warner et al. (1998) *Am J Physiol.* 275: L110–117; Saugstad (2001) *Acta Paediatr.* 90: 113–115; Fardy and Silverman (1995) *Arch Dis Child Fetal.* 73: F112–117; Coalson et al. (1995) *Am J Respir Crit Care Med.* 152: 640–646. Despite numerous advances, its pathogenesis remains incompletely understood. However, lung injury, abnormal repair, and truncation of alveolarization are its cardinal pathological features (5. Coalson et al. (1995) *Am J Respir Crit Care Med.* 152: 640–646; Jobe (1999) *Ped Res.* 46: 641–643; Husain et al. (1998) Hum Pathol. 29: 710–717). Although multiple factors, acting additively or synergistically, are known to be important in its causation, exposure to relative hyperoxia (at least in comparison to in utero oxygen tension) and alveolar stretch are the principal contributing factors. But the exact underlying mechanism linking hyperoxia to BPD remains poorly defined. In this study, we sought to determine whether exposure to hyperoxia accelerates the spontaneous in vitro transdifferentiation of pulmonary lipofibroblast to myofibroblasts, the characteristic cell seen in chronic lung disease (Phan et al. (1999) *Curr Top Pathol.* 93: 173–182; Gauldie et al. (1997) *Curr. Top. Pathol.* 93: 35–45; Toti et al. (1997) *Pediatr. Pulmonol.* 24: 22–28; Rehan et al. (2001) *Academy of Pediatric Societies,* Baltimore. A1716).

Lung interstitial fibroblasts play an important role in lung development and repair (Martinet et al. (1996) *Arch Toxicol Suppl.* 18: 127–139; Dooley et al. (2000) *Hepatology.* 31: 1094–1096; Shimizu et al. (1999) *Life Sci.* 64: 2081–2088; McGowan and Torday (1997)*Annu Rev Physiol.* 59: 43–62). Normal cell-cell communications between primordial interstitial fibroblasts and the developing lung epithelium seem to be essential for normal lung development and repair (Sugahara et al. (1998) *Cell Tissue Res.* 291: 295–303; Lebeche et al. (1999) *Mech. Dev.* 86: 125–136; Adamson et al. (1991) *Exp. Lung Res.* 17: 821–835; Shannon et al. (2001) *Am. J. Respir. Cell Mol. Biol.* 24:235–244; Smith and Post (1989) *Am. J. Physiol.* 257: L174–L178; O'Reilly et al. (1997) *Microsc Res Tech.* 38: 473–479). Disruption of the communications, from lipofibroblasts to epithelial cells and/or vice versa, by any factor may severely affect lung growth may play an important role in lung injury/BPD. Recent work has suggested that during specific developmental stages and in response to lung injury, interstitial fibroblasts differentiate along adipogenic or myogenic pathways and may transdifferentiate from one phenotype to the other (Heath et al. (2000) *Exp Cell Res.* 254: 91–98; Bruce et al. (1999) *Am J Respir Cell Mol Biol.* 20: 228–236; Gressner (1996) *Kidney Int Suppl.* 54: S39–45). The phenotypic characteristics of interstitial fibroblasts are of obvious central importance in determining the nature of signaling communications between the mesenchyme and the epithelium. In this study, we determined the effects of hyperoxia on characteristic lipogenic markers in the immature [(e) embryonic18] and relatively more mature (e21) fetal rat lung lipofibroblasts. We tested the hypothesis that hyperoxia will enhance the spontaneously occurring transdifferentiation of interstitial fibroblasts from an adipogenic to a myogenic phenotype and that this process is developmentally regulated.

Material and Methods

Reagents

Rat leptin antibody assay kit (rat, polyclonal) was acquired from Linco (St. Charles, Mo.). $^3$H-choline chloride and $^3$H-triolein were purchased from New England Nuclear, Boston, Mass. 2',7'-dichlorofluorescein diacetate was purchased from Molecular Probes, Inc (Eugene, Oreg.).

Animals

Time-mated Sprague-Dawley rats (time E0=day of mating) were obtained from Charles River Breeders (Holister, Calif.). These experiments were conducted in accordance with the NIH Guide for the Care and Use of Laboratory Animals.

Isolation of Fetal Rat Lung Fibroblasts (27)

Three to five time-mated (e18 and e21) Sprague Dawley rat dams were used per preparation depending on the number of experimental variables to be tested. The fetal lungs were removed into Hanks' balanced salt solution (HBSS). The HBSS was decanted and 5 volumes of 0.05% trypsin were added to the lung preparation. The lungs were dissociated in a 37° C. water bath using a Teflon™ stirring bar to disrupt the tissue mechanically. Once the tissue was dispersed into a unicellular suspension, the cells were pelleted at 500×g for 10 min at room temperature in a 50 ml polystyrene centrifuge tube. The supernatant was decanted and the pellet was resuspended in Dulbecco's Minimal Essential Medium (DMEM) containing 20% fetal bovine serum (FBS) to yield a mixed cell suspension of ca. 3×10$^8$ cells, as determined by Coulter particle counter (Beckman-Coulter, Hayaleah, Fla.). The cell suspension was then added to culture flasks (75 cm$^2$) for 30–60 min to allow for differential adherence of lung fibroblasts. These cells are greater than 95% pure fibroblasts based upon vimentin positive staining.

Cell Culture e18 (pre-term) and e21 (near term) fetal rat lung fibroblasts were maintained in DMEM+10% fetal bovine serum in 21% (control) or 95% (experimental) $O_2$+5% $CO_2$ in sealed modular incubator chambers (Billups-Rothenberg, Del Mar, Calif.) kept at 37 C in standard incubators. Modular incubators were flushed for 3 min at a flow rate of 10 liters/min with either 21 or 95% $O_2$+5% $CO_2$ with remainder of the gas mixture as $N_2$. Modular incubators were then sealed and then put in standard cell culture incubators. When confluent, cells were passaged and allowed to grow in 21% $O_2$ for 24 h. Subsequently, control cells were maintained in 21% $O_2$+5% $CO_2$ and experimental cells in 95% $O_2$+5% $CO_2$ in modular incubators as described above This was continued up to passage 5. Passage 1 and 5 cells were studied for the expression of various lipogenic and myogenic markers by reverse transcriptase-polymerase chain reaction (RT-PCR).

Isolation of Total Cellular RNA

Total cellular RNA was isolated using previously described methods (28). Cells were lysed directly by vortexing in 0.2 mL lysis solution [2M guanidium isothiocyanate, 12.5 mM sodium citrate (pH 7.0), 0.25% sarkosyl, 50 mM 2-mercaptoethanol, and 50% (vol/vol) water-saturated phenol]. Chloroform-isoamyl alcohol (49:1, vol/vol) was added to each sample and the mixture was vortexed and cooled on ice. After centrifugation at 10,000×g for 20 min at 4° C., RNA in the aq. phase was precipitated in EtOH at −20° C. The RNA was pelleted at 10,000×g for 20 min at 4° C., RNA in the aq. Phase was precipitated in EtOH at −20° C. After re-extraction in P:IC and EtOH precipitation, samples were resuspended in DEPC-treated water and quantitated by absorbance at 260 nm.

RT-PCR.

RT PCR probes used included-Rat Parathyroid Hormone related Protein Receptor (PTHrPR): 5' CTC TTC TTG ACT GTT GTC GCT GGT (SEQ ID NO:14) and 3'TTCTC-CTGGGTACCAGTTGGT (SEQ ID NO:15); Rat Peroxisome Peroliferator Activated Receptor (PPAR)γ 5' TAC ACA GTA CTT CTA CTA GAT G (SEQ ID NO:16) and 3' ATA GGC TGT TCA CTG GTG TTC C (SEQ ID NO:17); Rat Adipocyte Differentiation Related Protein (ADRP) Rat SP-C 5' ATC GTG GTT GTG GTG GTA GTC C (SEQ ID NO:18) and 3' CCC AGA AGA ATC AGA ATC GG (SEQ ID NO:19). Rat alpha Smooth Muscle Actin (SMA). RT-PCR was carried out for 2 hours at 37° C. in 50 mM Tris buffer, pH 8.3 containing 75 mM KCl, 3 mM MgCl2 and 10 mM DTT. The total volume of incubation was 20 µl and it contained 0.5 mM each of dNTP, 20 U of RNasin, 25 pmol of oligo(dt) primer and 200 U of Moroney murine leukemia virus reverse transcriptase. At the end of incubation, the reaction was stopped by heating a 90° C. for 5 minutes. PCR amplification was performed in 75 µl final reaction volume which contained the cDNA mixtures from various experimental conditions diluted with the reaction buffer (X10) to a final composition of 10 mM Tris buffer, pH 8.3; 50 mM KCl, 1.5 mM MgCl2 and 100 µM dNTPs, 2.5 U Taq polymerase and 55 pmol of each primer. The cDNA is adjusted to equal concentrations as assessed by the PCR of the constitutively expressed gene, GAPDH (rat lung GAPDH). The amount of 18 s synthesised from each cDNA template was visualized by ethidium bromide stained agarose gel electrophoresis. The reactions were run according to the standard protocols at 42° C. for 75 minutes and terminated by heating at 95° C. for 5 min. Co-amplification with 18 s cDNA will be used was the internal standard. PCR reaction was terminated by Taq DNA polymerase and allowed to proceed for 30 cycles with an annealing temperature at 50° C.

Measurement of Reactive Oxygen Species (ROS) level (2',7'-dichlorofluorescein Diacetate Assay)

The intracellular ROS was measured using a fluorescent dye, 2',7'-dichlorofluorescein diacetate (DCFH-DA) according to manufacturer's instructions (Molecular Probes, Inc, Eugene, Oreg.). DCFH-DA, a non-polar compound that readily diffuses into cells. There, it is hydrolyzed to a polar derivative, DCFH, and thereby trapped within the cells. In the presence of an oxidant, DCFH is converted to the highly fluorescent 2',7'-dichlorofluorescein. For assays, 5,000 cells were plated per well in 96-well microtiter plates and, when ready, exposed to experimental conditions. Cells were then loaded with 10 μM DCFH-DA, and incubated in the dark. After specified time points, the microtiter plates were analyzed for fluorescence using a fluorescein filter (485 nm/535 nm).

Statistical Analysis

Student's t-test or analysis of variance for multiple comparisons were used to analyze the experimental data, as indicated. $p<0.01$ was considered to indicate significant differences in the expression of lipogenic and myogenic markers of e18 and e21, P1 and P5 FRLF, in response to 21% and 95% $O_2$ exposures.

Results.

As our previous studies have demonstrated that when developing pulmonary lipofibroblasts are cultured in vitro, these spontaneously transdifferentiate to myofibroblasts (Rehan et al. (2001) *Academy of Pediatric Societies*, Baltimore. A1716), this series of experiments was designed to elucidate whether exposure to hyperoxia enhances this transdifferentiation process, and whether this effect is developmentally regulated. We have focused on the effect of hyperoxic exposure on PTHrPR expression and its downstream targets in interstitial fibroblasts as we have previously identified PTHrP to be a key molecule that links the paracrine signaling between the developing pulmonary fibroblasts and alveolar type II cells (Torday and Rehan (2000) *Am J Physiol Lung Cell Mol Physiol.* 283: L130–L135).

Figure 15:
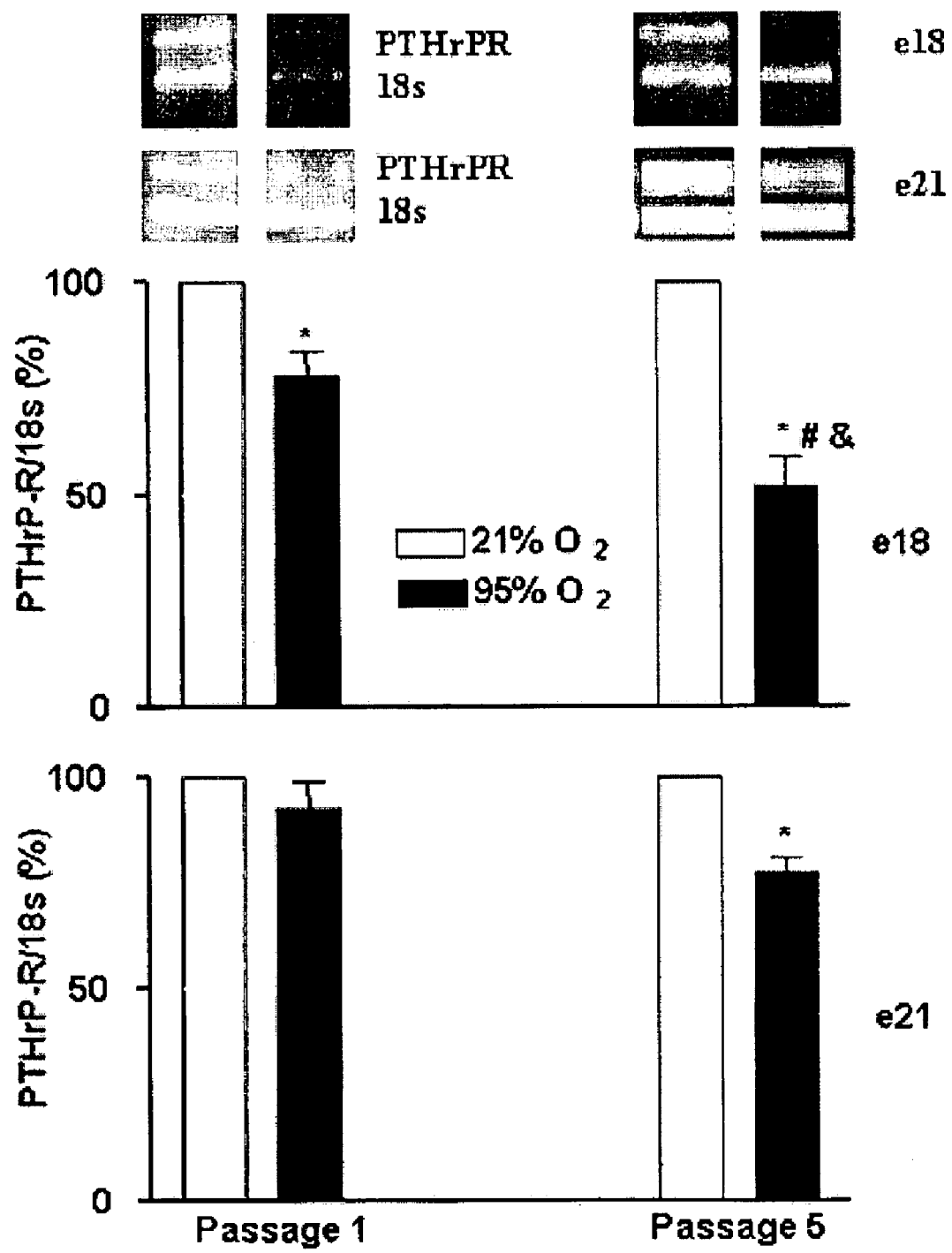
FIG. 15 shows that exposure to hyperoxia (95% $O_2$ for 24 h) caused a decrease (*=$p<0.05$ vs. 21% $O_2$) in PTHrPr mRNA expression in FRLFs at both passages 1 and 5; this effect being more pronounced for cells at passage 5 (#=$p<0.05$ vs. P1). Further, the decrease in PTHrPR mRNA expression was greater (&=$p<0.05$) for immature (e18) vs. relatively mature (d21) FRLF.
Figure 16:
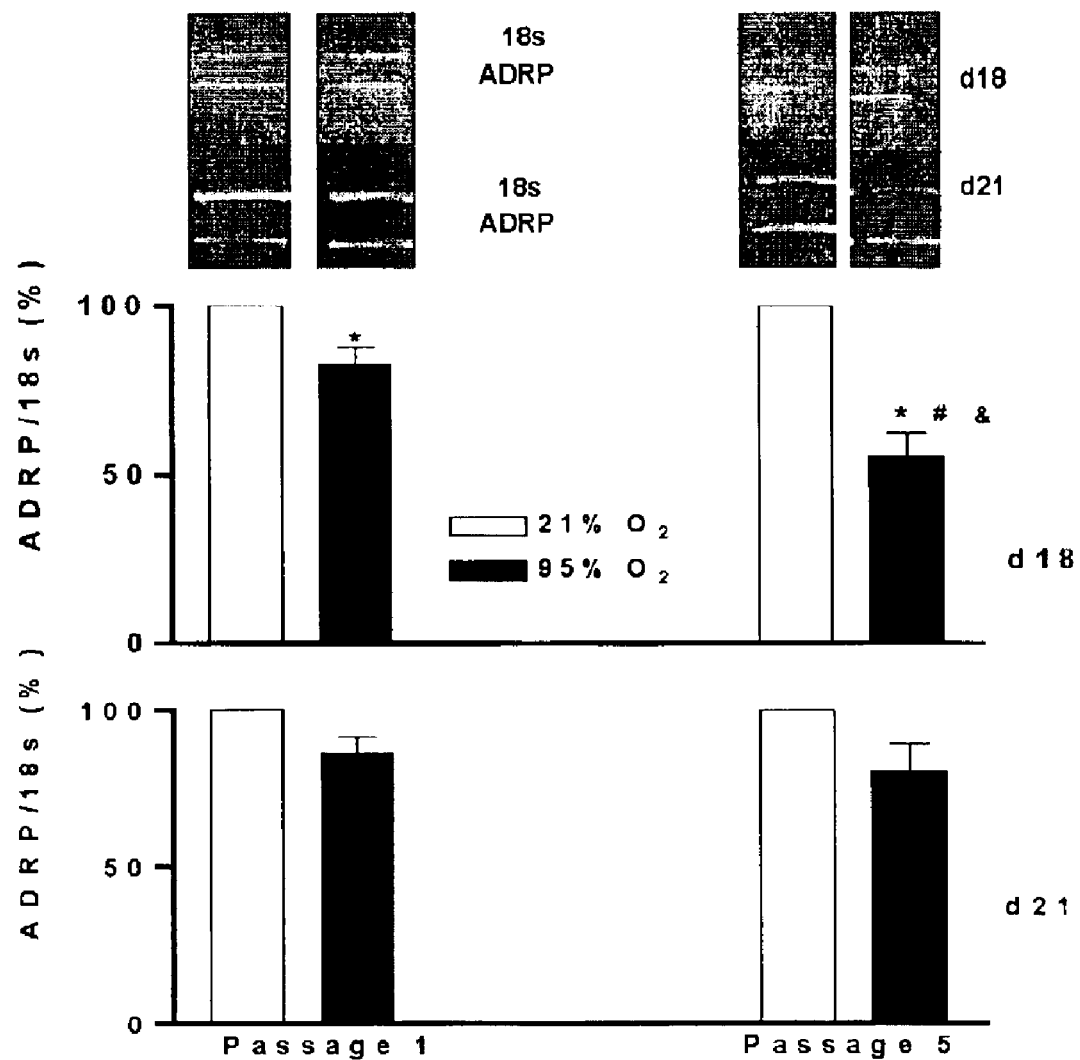
FIG. 16 shows that exposure to hyperoxia (95% $O_2$ for 24 h) caused a decrease (*=$p<0.05$ vs. 21% $O_2$) in ADRP mRNA expression in FRLFs at both passages 1 and 5; this effect being more pronounced for cells at passage 5 (#=$p<0.05$ vs. P1). Further, the decrease in ADRP mRNA expression was greater (&=$p<0.05$) for immature (e18) vs. relatively mature (e21) FRLF.
Figure 17:
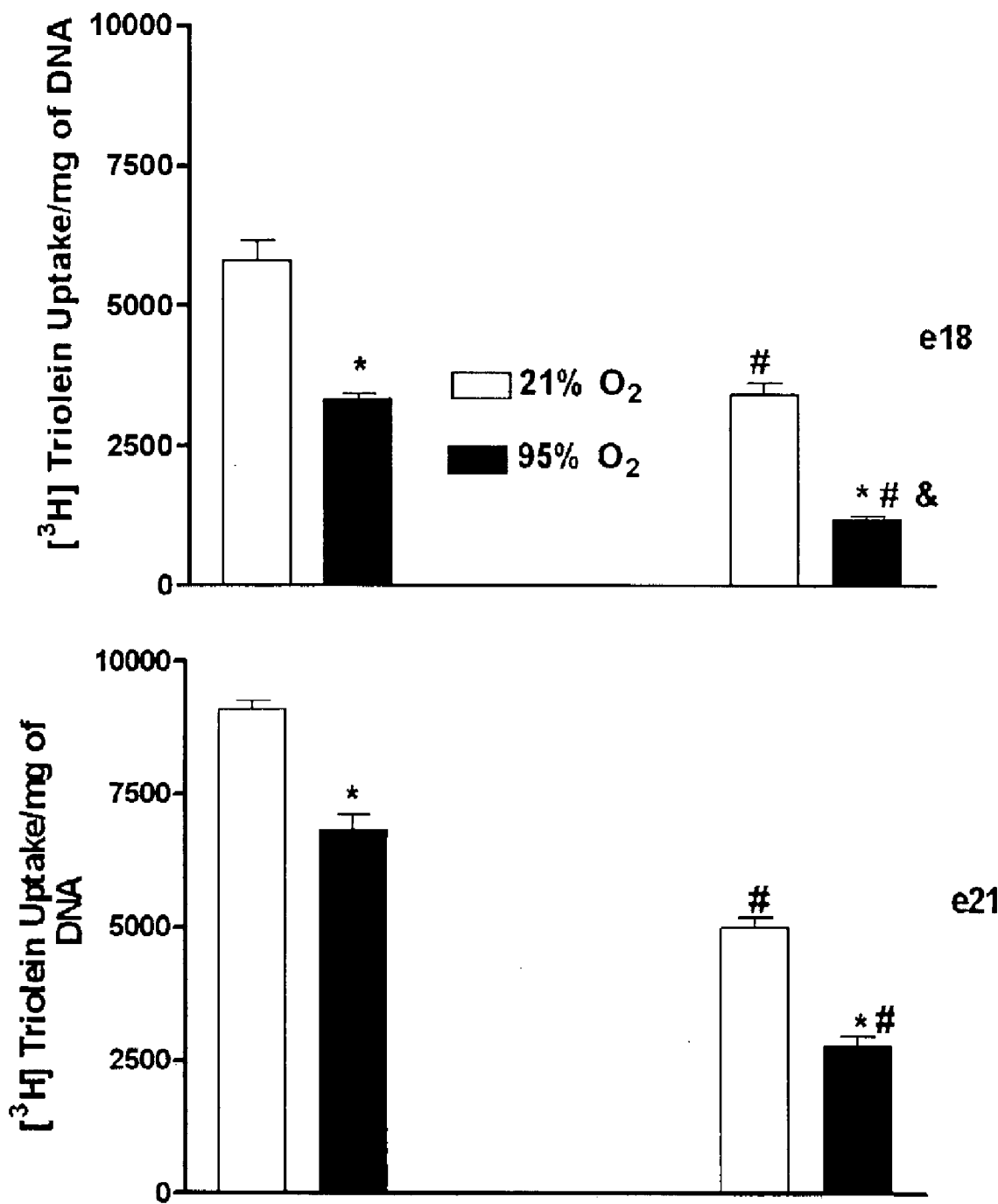
FIG. 17 shows that exposure to hyperoxia (95% $O_2$ for 24 h) caused decrease (*=$p<0.05$ vs. 21% $O_2$) in triolein uptake by FRLFs at both passages 1 and 5; the decrease in triolein uptake was more pronounced for cells at passage 5 (#=$p<0.05$ vs. P1) both spontaneously (in 21% $O_2$) and in response to hyperoxia exposure. Further, the decrease in triolein uptake was greater (&=$p<0.05$) for immature (e18) vs. relatively mature (e21) FRLF.
Figure 18:
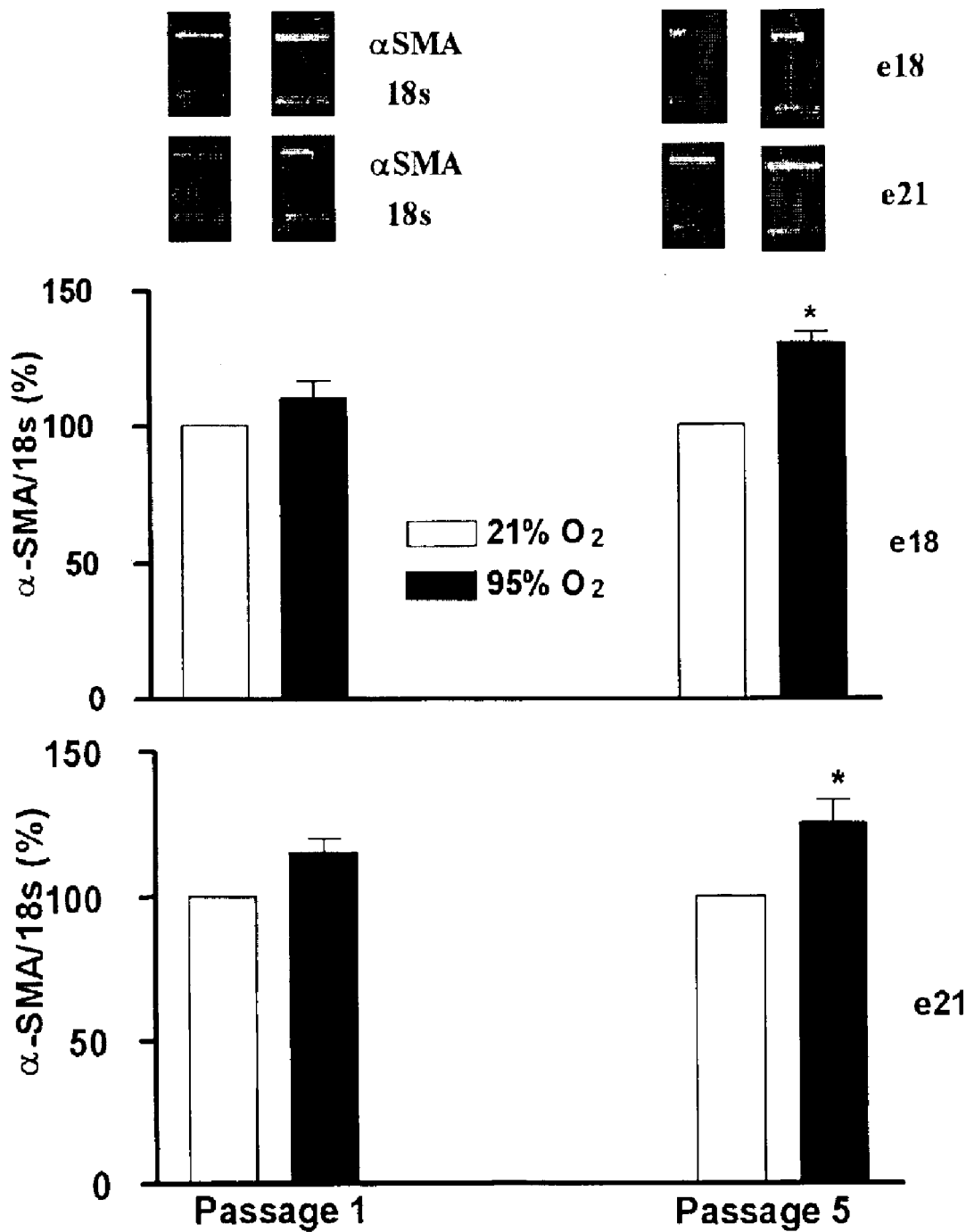
FIG. 18 shows that exposure to hyperoxia (95% $O_2$ for 24 h) caused an increase (*=$p<0.05$ vs. 21% $O_2$) in αSMA mRNA expression in FRLFs at passage 5 in both e18 and e21 FRLF; this effect was more pronounced in being more pronounced for cells at passage 5 (#=$p<0.05$ vs. P1).

Exposure to hyperoxia (95% $O_2$ for 24 h) at passages 1 and 5 caused significant decreases (*=p<0.05 vs. 21% $O_2$) in PTHrPR mRNA expression in the d18 fibroblasts (FIG. 15). This decrease was more pronounced in P5 fibroblasts (#=p<0.05, P7 vs. P1). In contrast, d21 fibroblasts were more resistant to the effects of hyperoxia than d18 fibroblasts. Since downstream effect of PTHrPR activation affects lipid metabolism through ADRP, we next tested the effect of hyperoxic exposure on both ADRP mRNA expression and the triglyceride uptake. Exposure to hyperoxia decreased ADRP mRNA expression (FIG. 16) and triglyceride uptake (FIG. 17). These effects were also more pronounced in d18 vs. d21 fibroblasts and in P5 vs P1 cells. The decreases in lipogenic markers (PTHrPR and ADRP mRNA expression and triglyceride up take), on exposure to hyperoxia, was accompanied by a concomitant increase in (x-smooth muscle actin (SMA) mRNA expression (FIG. 18). These changes were also most pronounced in d18 fibroblasts at P5.

Figure 19:
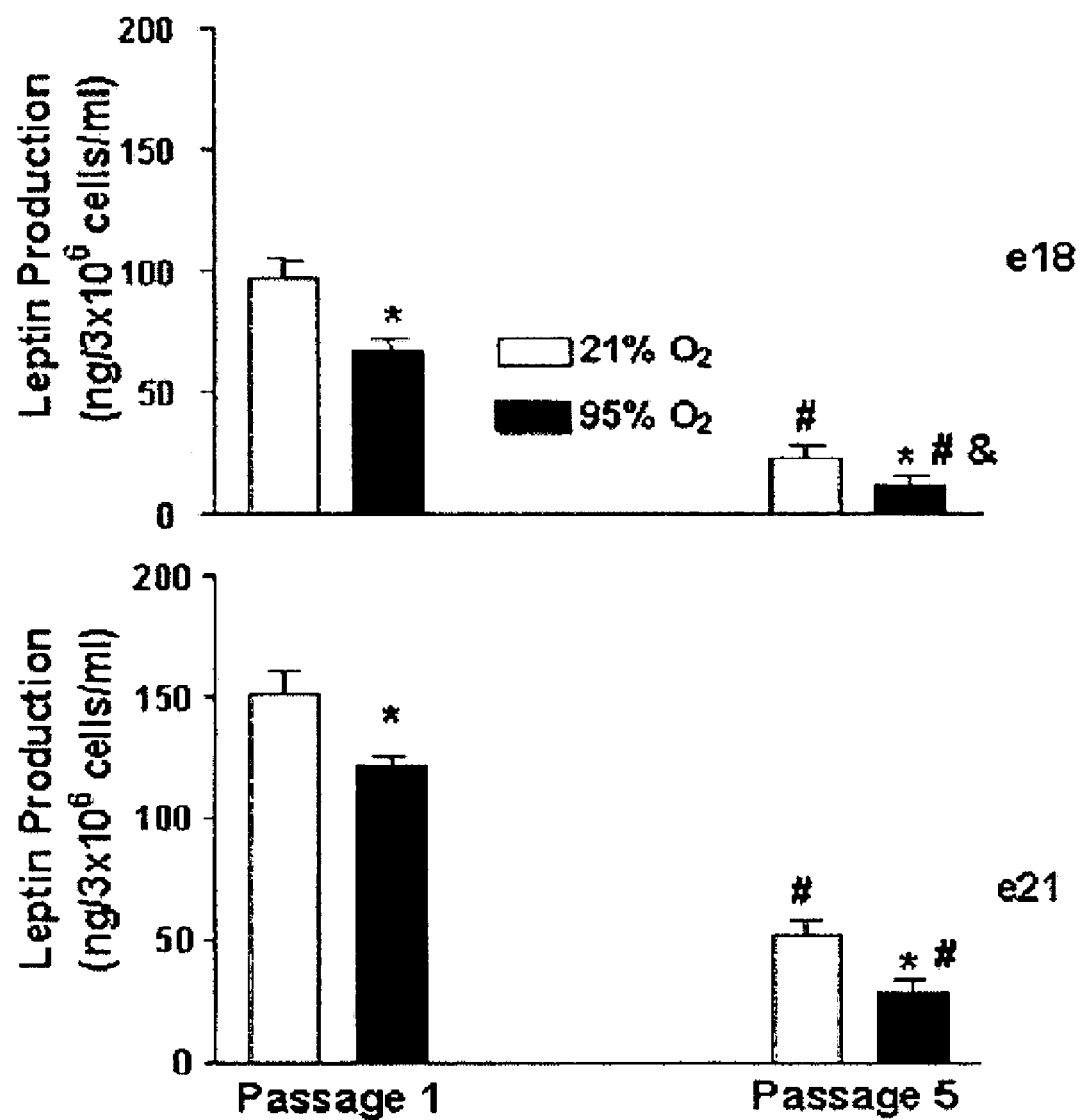
FIG. 19 shows that exposure to hyperoxia (95% $O_2$ for 24 h) caused a decrease (*=$p<0.05$ vs. 21% $O_2$) in leptin secretion in FRLFs at both passages 1 and 5; the decrease in leptin secretion was more pronounced for cells at passage 5 (#=$p<0.05$ vs. P1) both spontaneously (in 21% $O_2$) and in response to hyperoxia exposure. Further, the decrease in leptin secretion was greater (&=$p<0.05$) for immature (e18) vs. relatively mature (e21) FRLF.
Figure 20:
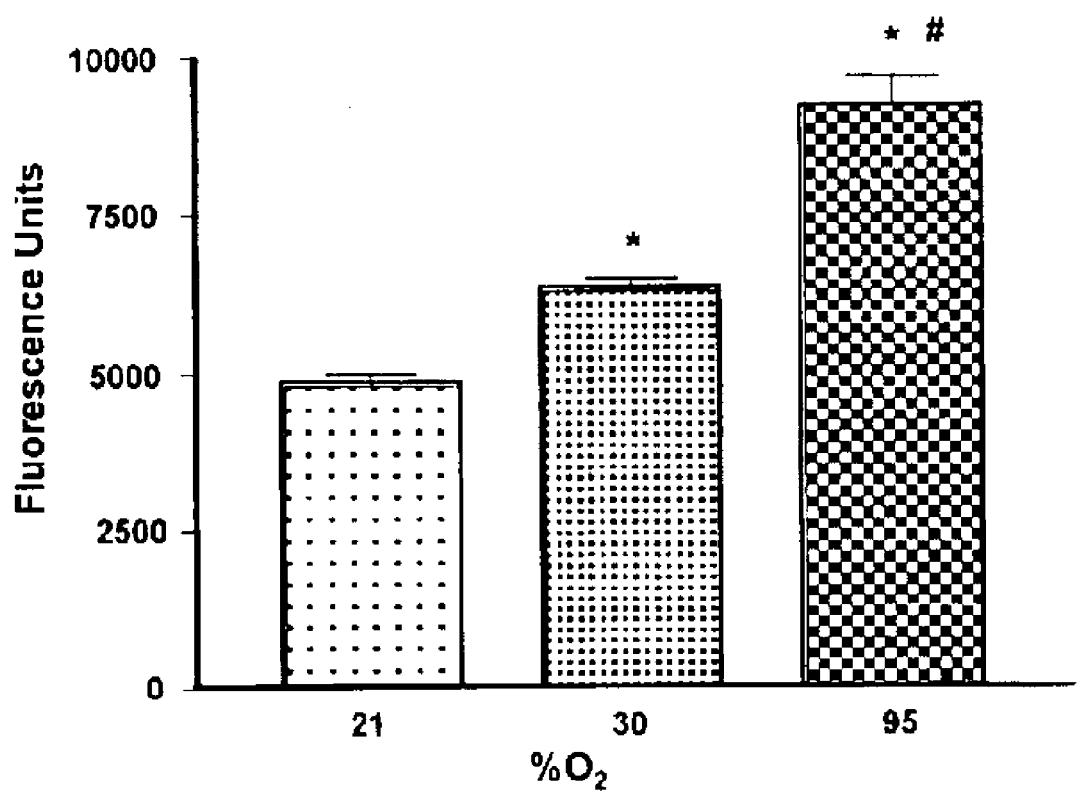
FIG. 20 shows that dose-dependent increases in ROS content occur when d18 FRLFs are exposed to increasing doses of oxygen (60 min. exposure). *=$p<0.05$ vs 21% $O_2$ control and #=$p<0.05$ vs 30% $O_2$.

Based on our recent demonstration that leptin expression by lipofibroblasts completes the mesenchymal-epithelial-mesenchymal paracrine loop between ATII cells and lipofibroblasts for PTHrP to stimulate the surfactant synthesis by type II cells, we next examined the effect of hyperoxia on leptin secretion by lipofibroblasts. Exposure to hyperoxia, significantly decreased leptin expression by lipofibroblasts (FIG. 19). The most prominent decrease was observed in d18 P5 fibroblasts. In order to study the mechanism of hyperoxia-enhanced transdifferentiation of pulmonary lipo-to-myofibroblasts, we next studied the generation of reactive oxygen species, by the fibroblasts on exposure to hyperoxia. Using 2',7'-dichlorofluorescein diacetate (DCFH) assay, we demonstrated a dose-dependent increases in ROS content of d18 FRLFs (60 min. exposure) (FIG. 20).

Figure 21:
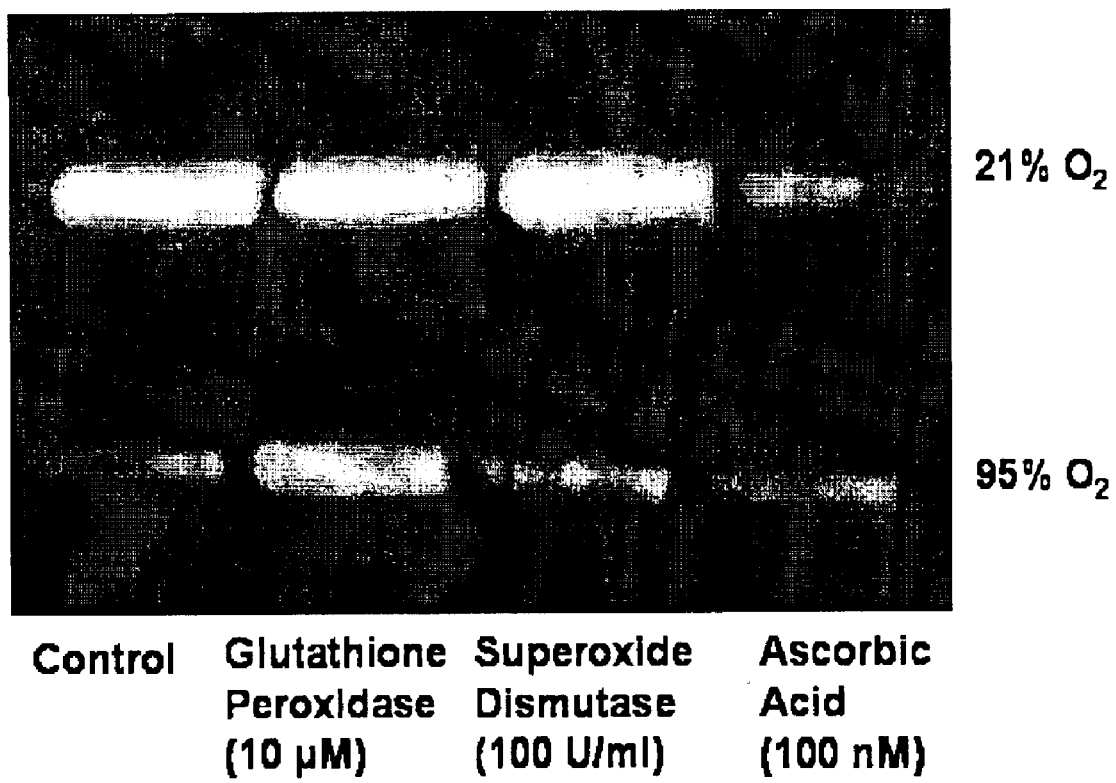
FIG. 21 shows that exposure of d18 FRLFs to hyperoxia (95% $O_2$) for 24 h caused a dramatic decrease in ADRP mRNA expression. This effect was prevented only by glutathione peroxidase preincubation, while superoxide dismutase and ascorbate were ineffective, suggesting the involvement of specific oxygen radicals in reducing ADRP mRNA expression in response to hyperoxia.
Figure 22:
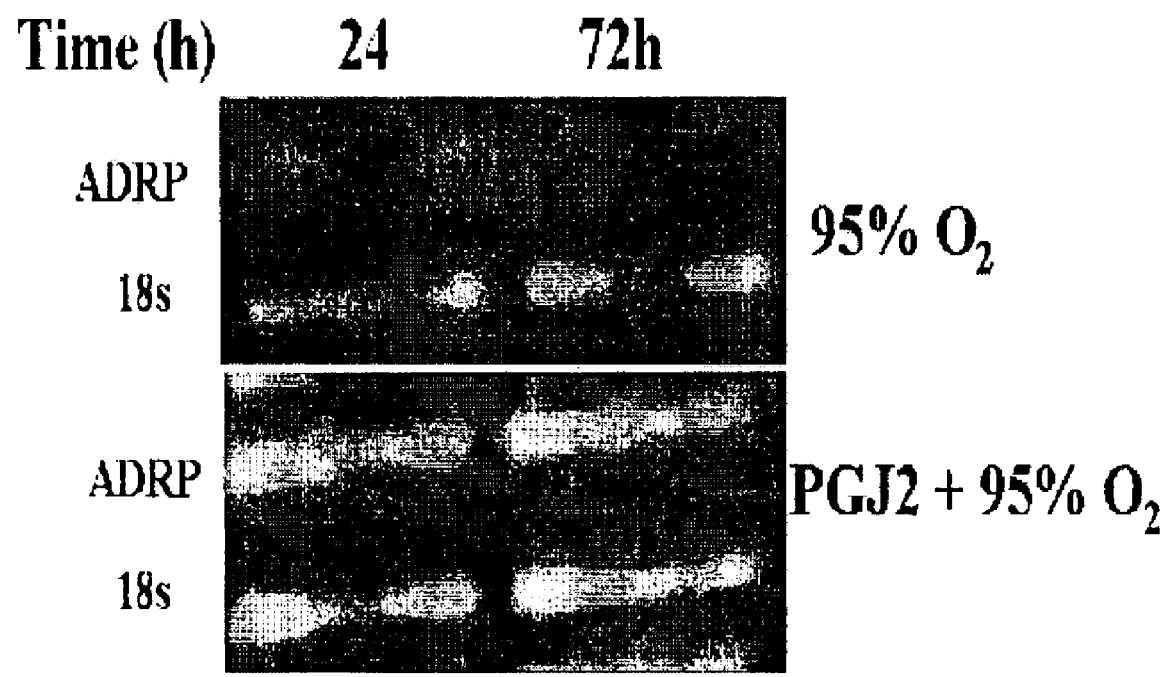
FIG. 22 shows that treatment with $PGJ_2$ (30 $\mu$M) attenuated (bottom panel) the spontaneous decrease (upper panel) in ADRP mRNA expression up to 72 h in culture.

In order to assess the role of reactive oxygen species in this transdifferentiation process, we studied the effect of antioxidant pretreatment on ADRP mRNA expression as a marker of lipogenic status of lipofibroblasts. Cultured FRLFs were exposed to 21% or 95% $O_2$ for 24 h following one hour pretreatment with antioxidants (FIG. 21). Hyperoxia-induced lipo-to-myofibroblast transdifferentiation was, at least partially, attenuated with selective antioxidant pretreatment, further reinforcing the role of specific ROS in this process. As a further evidence that enhanced lipogenic status may have preventive effect on oxygen-enhanced transdifferentiation, the effect of treatment with PGJ2, an agent that is known to boost the lipogenic status of these fibroblasts, was tested; we determined that 24 h treatment with $PGJ_2$ (30 μM) attenuates the spontaneous decrease in lipogenic (FIG. 22), and at least, partially blunts the hyperoxia induced lipo-to-myofibroblast transdifferentiation.

Discussion

Our data for the first time provides evidence that exposure to hyperoxia enhances lipo-to-myofibroblast transdifferentiation in FRLFs. This process is developmentally affected as it was more pronounced in relatively immature e18 vs more mature e21 fibroblasts. The underlying mechanisms involve intricate signaling pathways, which are the focus of our on-going studies. Treatment with lipogenic agents, at least, partially prevented the lipo-to-myofibroblast transdifferentiation. Given the critical importance of lipofibroblasts in maintaining pulmonary epithelial integrity, it is likely that hyperoxia-enhanced transdifferentiation of lipofibroblast to a myofibroblast phenotype plays a critical and possibly a central role in the pathogenesis of BPD.

During lung development, epithelial-mesenchymal communications through various soluble factors, including growth factors and cytokines play a key role in normal growth and development, and response to lung injury (Sugahara et al. (1998) *Cell Tissue Res.* 291: 295–303; Lebeche et al. (1999) *Mech. Dev.* 86: 125–136; Adamson et al. (1991) *Exp. Lung Res.* 17: 821–835; Shannon et al. (2001) *Am. J. Respir. Cell Mol. Biol.* 24:235–244; Smith and Post (1989) *Am. J. Physiol.* 257: L174–L178; O'Reilly et al. (1997) *Microsc Res Tech.* 38: 473–479; Torday and Rehan (2000) *Am J Physiol Lung Cell Mol Physiol.* 283: L130–L135). For instance, primordial epithelial cells produce PTHrP and express leptin receptor, and the neighboring undifferentiated fibroblasts produce leptin and express PTHrP receptor. This specific paracrine loop creates specific signal transduction pathways that induce the fibroblast and epithelial phenotypes that maintain alveolar homeostasis (Torday and Rehan (2000) *Am J Physiol Lung Cell Mol Physiol.* 283: L130–L135). Specifically, PTHrP induces primordial fibroblasts to become lipofibroblasts, which promote alveolar homeostasis by providing substrates for surfactant phospholipid synthesis, retinoic acid which maintains epithelial differentiation, and stores neutral lipids which act as anti-oxidants to protect the alveolar acinus against oxygen free radical (McGowan and Torday (1997) *Annu Rev Physiol.* 59: 43–62; Torday et al. (2001) *Pediatr. Res.* 49: 1–7; Torday et al. (1995) *Biochim Biophys Acta.* 1254: 198–206). When pulmonary epithelial-mesenchymal communications are disrupted by any mechanism, e.g., down regulation of PTHrP receptor on exposure to hyperoxia, as observed by us, it is likely to disrupt the normal growth and development, and impair the normal repair mechanisms. Our data clearly shows that down regulation of PTHrP receptor on hyperoxic exposure leads to the loss of lipid storage and lipid trafficking function of lipofibroblasts that are so crucial not only for optimal functioning of fibroblasts but also of the neighboring type II cells. On the contrary, it has been shown that factors that promote fibroblast development may augment mesenchymal-epithelial communications and may have the potential to stabilize the alveoli and prevent lung injury (O'Reilly et al. (1997) *Microsc Res Tech.* 38: 473–479; Mendelson (2000) *In Endocrinology of the Lung,* Humana Press, Totowa, N.J.).

PTHrP binding to PTHrP receptor on the surface of mesenchymal fibroblasts triggers both the protein kinase A and protein kinase C pathways, stimulating the lipogenic phenotype, including lipoprotein lipase, fatty acid synthase and ADRP (Rubin et al. (1994) *Biochim Biophys Acta.* 1223: 91–100; Rubin and Torday (2000) Pages 269–297 In: *Endocrinology of the Lung.* Humana Press, Totowa, N.J.) expressions. On exposure to hyperoxia, we found that down regulation with PTHrP receptor is associated with down regulation of ADRP, which is a recently identified marker for specialized cells containing lipid droplets (Londos et al. (1999) *Semin Cell Dev Biol.* 10: 51–8; Schultz et al. (2002) *Am J Physiol Lung Cell Mol Physiol.* 283(2): L288–296). This novel 50 kDa membrane-associated protein is necessary for sorting and exocytosis of lipid droplets. ADRP is expressed in a variety of adipogenic tissues and cultured cell lines, where it is localized on the surface of neutral lipid storage droplets. ADRP mRNA levels are rapidly and maximally induced upon triggering adipocyte differentiation. It has been recently shown that ADRP mRNA and protein are stimulated during pulmonary lipofibroblast differentiation and by treatment with PTHrP (Schultz et al. (2002) *Am J Physiol Lung Cell Mol Physiol.* 283(2): L288–296). Therefore, it not surprising that PTHrP receptor down regulation, on exposure to hyperoxia, was accompanied by decreased ADRP mRNA expression. Further, as ADRP plays an important role in surfactant synthesis in the developing lung, its down regulation on exposure to hyperoxia suggests not only the loss of lipogenic characteristic for the lipofibroblast but also impaired function of the pulmonary type II cell.

The possibility that exposure of cultured fibroblasts (which, at P1, comprise almost entirely of lipofibroblasts based on lipid and vimentin staining) to hyperoxia is associated with adaptation of clones or subpopulation of fibroblasts (~myofibroblasts) that continue to divide and maintain a selective advantage. However, it is noteworthy that clastogenesis is more likely to occur following low level oxidants exposure rather than in cells exposed to 95% $O_2$ (Gille and Joenje (1992) *Mutat Res.* 275: 405–414). The cellular mechanisms by which hyperoxia accelerates the observed lipo-myofibroblast transdifferentiation remains to be explored and is currently under investigation. It is likely that the generation of ROS, on exposure to hyperoxia, acts as a second messenger to stimulate protein kinase cascades coupled to the expression of key lipogenic markers (Hashimoto et al. (2001) *Am J Respir Crit Care.* 163: 152–157). Relative lack of antioxidant defenses in e18 compared to e21 lung fibroblasts renders them more susceptible to the damaging effects of ROS (Torday et al. (2001) *Pediatr. Res.* 49: 1–7). These findings confirm and support our recent observations that metabolic enzymes affecting ribose acid synthesis and lipogenesis from glucose by these fibroblasts show maturation dependent sensitivity to hyperoxia, and may play a key role in the transdifferentiation of lung fibroblasts to myofibroblasts in the pathogenesis of BPD.

Experimental evidence for plasticity between the lipofibroblastic and myofibroblastic phenotypes largely comes from studies on the role of stellate cells in liver fibrosis and on the transcriptional control of adipogenesis (Gao and Serrero (1999) *J Biol Chem.* 274: 16825–16830; Dooley et al. (2000) *Hepatology.* 31: 1094–1096; Shimizu et al. (1999) *Life Sci.* 64: 2081–2088). When rat stellate cells are cultured in vitro, they rapidly lose neutral lipid stores, acquire characteristics of proliferating myofibroblast-like cells (Potter et al. (1999) *Liver* 19: 135–144), and increase secretion of collagen, mainly type I, but also types III and VI (Weber (1997) *Semin Nephrol.* 17: 467–491; Tang et al. (1997) *Kidney Int.* 51: 926–931). This transdifferentiation process can be altered by treatment with specific agents. For example, PPAR treatment of transdifferentiating stellate cells in culture inhibits expression of α-SMA and other myogenic markers (Marra et al. (2000) *Gastroenterology.* 119: 466–478; Galli et al. (2000) *Hepatology.* 31: 101–108). There is evidence to suggest that myofibroblasts are not terminally differentiated, and that specific transcriptional agonists can induce their re-differentiation into their parent fibroblast phenotype. Demonstration by us that treatment with PGJ2, at least, could partially prevent the hyperoxia-enhanced transdifferentiation of lipofibroblast to myofibroblasts suggests that treatment with either PGJ2 or similar agents can prevent this process and may inhibit or prevent fibrosis. We have recently shown that lipofibroblast differentiation to myofibroblasts can be rescued by PTHrP early in the course of lipofibroblast-to-myofibroblast conversion. However, once these cells lose their ability to express the PTHrPR, they can no longer be rescued by PTHrP. The data presented here and our previous metabolic enzymatic changes in response to hyperoxia suggest significant metabolic adaptations in conjunction with the key molecular alterations in the developing FRLF. The mechanism through which hyperoxia induces transdifferentiation of lipofibroblastic to a myofibroblastic phenotype remains unknown and better understanding of this process will allow designing newer preventive strategies that will potentially reduce the fibrotic response during hyperoxia induced pulmonary injury.

Example 3

Oxygen-Induced Metabolic Changes and Transdifferentiation in Immature Fetal Rat Lung Lipofibroblasts Preterm infants lack adequate surfactant production and often require oxygen support for adequate oxygenation. Prolonged oxygen treatment leads to the development of bronchopulmonary dysplasia (BPD), a disease process characterized by the blunting of alveolarization and proliferation of myofibroblasts. In the present study, we investigated metabolic adaptive changes in cultured fibroblasts isolated from immature (d18) and near-term (d21) fetal rat lungs in response to normoxic (21%) and hyperoxic (95%) exposures. We used the $[1,2-^{13}C_2]$-D-glucose tracer and gas chromatography/mass spectrometry to characterize glucose carbon redistribution between the nucleic acid ribose, lactate, and palmitate synthetic pathways, and reverse transcriptase-polymerase chain reaction to assess Adipose Differentiation Related Protein mRNA expression in response to hyperoxic exposure. Exposure to hyperoxia at each passage caused decrease (*=$p<0.05$ vs. 21% $O_2$) in ADRP mRNA expression in the immature (e18) fibroblasts. This passage dependent transdifferentiation is accompanied by a moderate (9% to 20%) increase in the synthesis of nucleic acid ribose from glucose through the non-oxidative steps of the pentose cycle. In contrast, immature fibroblasts (d18) showed over an 85% decrease in the de novo synthesis of palmitate from glucose, while more mature fibroblasts (d21) showed a less pronounced 32% to 38% decrease in de novo lipid synthesis in hyperoxia-exposed cultures. It can be concluded from these studies that 1) there is a maturation dependent sensitivity to hyperoxia; 2) transdifferentiation of fibroblast as demonstrated by changes in ADRP expression is accompanied by metabolic enzymes changes affecting ribose acid synthesis from glucose, and 3) hyperoxia specifically inhibits lipogenesis from glucose. Hyperoxia-induced metabolic changes thus play a key role in the transdifferentiation of lung fibroblasts to myofibroblasts and the pathogenesis of BPD.

Introduction:

Resident lipofibroblasts of the neonatal lung interstitium are supportive cells that provide lipids and various nutrients to type II pneumocytes for the synthesis and release of phospholipid and protein rich surfactant necessary for normal lung function (Vaccaro and Brody (1978) *Anat. Rec.* 192:467–79; McGowan and Torday (1997) *Annu. Rev. Physiol.* 59:43–62). The immature lung is deficient in surfactant and usually requires oxygen and ventilatory support for adequate oxygenation (Abman and Groothius (1994) *Pediatr. Clin. North Am.,* 41:277–315). However, immature lipofibroblasts, on exposure to hyperoxia, show a tendency to transdifferentiate towards a phenotype with contractile elements and a high proliferating potential, and are referred to as myofibroblasts (Pache et al. (1998) *Mod. Pathol.* 11:1064–1070). Pulmonary lipofibroblasts, like hepatic lipofibroblasts, accumulate lipid droplets and exhibit related differentiated functions. However, these specific functions do not appear to reflect a state of terminal differentiation, because under specific stimuli, these lipofibroblasts can transdifferentiate to myofibroblasts and vice versa (Bruce et al. (1999) *Am. J. Respir. Cell Mol Biol.,* 20:228–236; Gressner (1996) *Kidney Int. Suppl.,* 54:S39–45; Potter et al. (1999) *Liver,* 19:135–144). Although transdifferentiation occurs spontaneously, we have observed that it is accelerated on exposure to hyperoxia (Rehan et al. (2001) *Academy of Pediatric Societies,* Baltimore, April).

The transdifferentiation of lipofibroblasts into myofibroblasts is accompanied by the gradual loss of several lipogenic markers, such as lipid stores, expression of the Parathyroid Hormone-related Protein receptor, Adipose Differentiation Related Protein (ADRP) and Peroxisome Proliferator-activated Receptor gamma (PPAR( ). Myofibroblasts express and produce actin, exhibit a highly proliferative phenotype, and are devoid of lipid inclusions and ADRP. In addition to such molecular genetic markers, transdifferentiation is also known to be associated with metabolic changes resulting in their limited capacity for providing valuable nutrients and lipid precursors needed by type II pneumocytes for adequate surfactant production (Torday et al. (1995) *Biochim Biophys Acta.* 1254:198–206) and antioxidant protection (Torday et al. (2001) *Pediatr. Res.* 49(6): 843–849).

Here we report metabolic changes associated with transdifferentiation of lung lipofibroblasts, exposed to hyperoxia, using $[1,2-^{13}C_2]$glucose. Metabolic pathways of glucose metabolism can be traced by the specific incorporation of $^{13}C$ into glucose metabolic intermediates. Glucose oxidation in the tricarboxylic acid (TCA) cycle, de novo lipid synthesis as well as utilization of glucose carbon for ribose synthesis can be studied using as a single tracer. These changes are correlated to markers of transdifferentiation. The effect of immaturity (both in terms of gestational age and cell passage number) on the sensitivity to hyperoxia-induced changes were also examined.

Materials and Methods:

Animals: Isolation of Fetal Rat Lung Fibroblasts:

Fetal rat lung fibroblasts were isolated as previously described (Torday et al. (1995) *Biochim Biophys Acta.* 1254:198–206; Torday et al. (2001) *Pediatr. Res.* 49(6):843–849). Briefly, five to ten time-mated (e18 and e21) Sprague Dawley rat dams were used. The fetal lungs were removed into Hanks' balanced salt solution (HBSS), the HBSS was decanted and 5 volumes of 0.05% trypsin were added. The lungs were incubated in a 37° C. water bath using a Teflon™ stirring bar to mechanically disrupt the tissue. Once the tissue was dispersed into a unicellular suspension, the cells were pelleted at 500×g for 10 min at room temperature in a 50 mL polystyrene centrifuge tube. The supernatant was decanted and the pellet was re-suspended in Dulbecco's Minimal Essential Medium (DMEM) containing 20% fetal bovine serum (FBS) to yield a mixed cell suspension of ca. $3\times10^8$ cells, as determined by Coulter particle counter (Beckman-Coulter, Hyaleah, Fla.). The cell suspension was then added to T75 culture flasks for 30–60 min to allow for differential adherence of lung fibroblasts. Unattached cells were removed by serial washes using HBSS. Cell cultures contained greater than 95% pure fibroblasts based upon their positive vimentin staining, and all the cells contain neutral lipid pools by electron microscopy.

Cell Culture e18 (immature) and e21 (near-term) fetal lung fibroblasts were maintained in DMEM+10% FBS in 21% (control) or 95% (experimental) $O_2+5\% CO_2$ at 37° C. in a humidified incubator. When confluent, cells were subcultured in a ratio of 1:3 and allowed to grow in 21% $O_2$ for 24 h. Billup-Rothenburg modular incubators were used to expose the cell cultures to the desired oxygen concentrations. Incubators were flushed for 3 min at a flow rate of 10 liters/min with either 21% or 95% $O_2+5\% CO_2$, with $N_2$ as the balance gas for the mixture. Modular incubators were sealed and then put into the incubator for 72 hours. Control cells were maintained in 21% $O_2+5\% CO_2$, and experimental cells were maintained in 95% $O_2+5\% CO_2$ This was continued for up to 10 passages. Passage 1, 4, and 7 cells were studied for the expression of ADRP through RT-PCR, and passage 1, 4, 7, and 10 cells were studied for stable isotope labeling of intracellular glucose metabolites, as described below.

Competitive RT-PCR

Competitive RT-PCR: was performed as described by the standard protocol (Ambion, Austin, Tex.). We used the commercially available primer and competimer™ for 18 s ribosomal RNA to control for the variables in the PCR reaction (i.e. time, temperature, number of cycles, reaction components) and aliquot loading variability across samples. Optimal primer/competimer pairs were constructed for the optimization of quantitative RT-PCR. The following primers were used: rat ADRP sense, 5'-GAA CAA AGG TCC TCA TTA TGG TCA TTC ACA GCT CAC TTA TGG TCG TGC-3' (SEQ ID NO:20); antisense, 5'-GCA CGA CCA TAA GTG AGC TGT GAA TGA CCA TAA TGA GGA CCT T T GTT C-3' (SEQ ID NO:21), and rat α-SMA, sense 5'-GAG ATG GCC ACT GCT GCT TCC-3' (SEQ ID NO:22); antisense 5'-GCC GCC GAT CCA GAC AGA ATA-3' (SEQ ID NO:23).

Stable Isotope Labeling of Intracellular Glucose Metabolites

This was performed according to the previously described methods (Sherry and Malloy (1996) *Cell Biochem. Funct.* 14:259–268; Lee (1996) *Adv. Exp. Med. Biol.* 399:95–114; Lee et al. (1995) *Anal. Biochem.* 226:100–112; Poot (1991)

Mutat. Res. 256:177–189; Chesney et al. (1999) *Proc Natl Acad Sci USA* 96:3047–3052; Lee et al. (1998) *Am. J. Physiol.* 274:E843–851; Barth et al. (1998 *Isotopes Environ. Health Stud.,* 34:209–213; Boros et al. (2001) *Pancreas* 22:1–7; Horecker et al. (1958) *Archives of Biochemistry and Biophysics* 18:510–517; Bunt et al. (1998) *Am. J. Respir. Crit. Care Med.,* 157:810–814). Briefly, pulmonary fibroblasts obtained from e18 and e21 fetal rats were incubated in the presence of DMEM containing 180 mg/dl $[1,2-^{13}C_2]$ glucose in order to determine the changes in carbon flux in response to control (21%) and hyperoxic (95%) exposures. The $^{13}C$ label from glucose is readily incorporated into various metabolites in mammalian cells, including ribonucleic acid (through ribose synthesis), lactate (through glycolysis), glutamate (through the TCA cycle) and palmitate (through the formation of acetyl-CoA) (Sherry and Malloy (1996) *Cell Biochem. Funct.* 14:259–268). As the molecular weight (atomic mass unit, AMU) of these molecules increases upon incorporation of the heavier $^{13}C$ carbon atoms derived from $[1,2,^{13}C_2]$ glucose, they can be separated and quantitatively analyzed by gas chromatography/mass spectrometry (GC/MS) based on changes in their mass/charge ratios. This method allows estimation of the relative synthetic rates of macromolecules using their common precursors in response to various treatments (Lee (1996) *Adv. Exp. Med. Biol.* 399:95–114). The stable isotope $[U-^{13}C]$glucose has previously been used to study surfactant synthesis and turnover in vivo in pre-term infants as the precursor for palmitic acid incorporation into the fatty acyl moiety of surfactant phosphatidylcholine (Bunt et al. (1998) *Am. J. Respir. Crit. Care Med.,* 157:810–814).

$[1,2-^{13}C_2]$glucose was purchased with >99% enrichment for the specified carbon positions from Isotech (Miamisburg, Ohio). Fibroblasts were plated onto T75 tissue culture flasks and incubated in the presence of 50% isotope-enriched glucose for 72 hours at passages 1, 4, 7 and 10. Experimental cells were simultaneously exposed to hyperoxia and isotope labeling for 72 hours at the desired passages.

Recovery of Glucose Metabolites from Lung Fibroblasts

Media glucose and lactate levels were directly measured using a Cobas Mira chemical analyzer (Roche Diagnostics). Glucose oxidation by fibroblasts was determined based on the media $^{13}C/^{12}C$ ratios in released $CO_2$ by a Finnegan Delta-S Isotope Ratio Mass Spectroscope (GC/C/IRMS). The rate of $^{13}CO_2$ release was measured to estimate the rate of glucose carbon oxidation by the cells, expressed as the atom percent excess, which is the proportion of $^{13}C$ produced by the cultured cells above background in calibration standard samples (Barth et al. (1998 *Isotopes Environ. Health Stud.,* 34:209–213).

RNA Ribose

RNA ribose was isolated by acid hydrolysis (2N HCL for two hours) of cellular RNA after Trizol-extraction of cell pellets. Ribose isolated from RNA was derivatized to its aldonitrile acetate form using hydroxyl-amine in pyridine and acetic anhydride. We monitored the ion clusters around m/z256 (carbons 1–5 of ribose, chemical ionization, CI), m/z217 (carbons 3–5 of ribose) and m/z242 (carbons 1–4 of ribose, electron impact ionization, EI) in order to detect the molar enrichment for, and the positional distribution of $^{13}C$ label in ribose (Boros et al. (2001) *Pancreas* 22:1–7; Horecker et al. (1958) *Archives of Biochemistry and Biophysics* 18:510–517).

Lactate

Lactate in the cell culture medium (0.2 ml) was extracted with ethyl acetate after acidification with HCl. Lactate was derivatized to its propylamine-heptafluorobutyric anhydrate form, and the m/z328 ion cluster (carbons 1–3 of lactate, chemical ionization, CI) was monitored for the detection of m1 (recycled lactate through the PC) and m2 (lactate produced by the Embden-Meyerhof-Parnas pathway) in order to estimate pentose cycle activity (Lee et al. (1998) *Am. J. Physiol.* 274:E843–851).

Fatty Acids

Fatty acids in the cell culture medium were extracted by saponification of the Trizol cell extract after removal of the RNA-containing supernatant. Cell debris was treated with 30% KOH and 100% ethanol overnight, and lipid extraction was performed using petroleum ether. Fatty acids were converted to their methylated derivatives using 0.5N methanolic-HCL. Palmitate was monitored at ion cluster m/z270. The enrichment of acetyl units and the de novo synthesis of the lipid fraction were determined using the Mass Isotopomer Distribution analysis (MIDA) approach for different isotopomers of palmitate (Lee et al. (1995) *Anal. Biochem.* 226:100–112).

Gas Chromatography/Mass Spectrometry (GC/MS).

Mass spectral data were obtained on an HP5973 mass-selective detector connected to an HP6890 gas chromatograph. The settings were as follows: GC inlet 230° C., transfer line 280° C., MS source 230° C., MS Quad 150° C. An HP-5 capillary column (30 m length, 250 μm diameter, 0.25 μm film thickness) was used for glucose, ribose, and lactate analyses. A Bpx70 column (25 m length, 220 μm diameter, 0.25 μm film thickness, SGE Inc., Austin, Tex.) was used for fatty acid analysis with specific temperature programming for each compound studied.

Data Analysis and Statistical Methods:

In vitro experiments were carried out using three cultures for each treatment regimen, and the experiments were repeated 1 to 3× times. Mass spectral analyses were carried out by three independent, automated injections of a 1 μl sample, and accepted only if the sample standard deviation was less than 1% of the normalized peak intensity Statistical analysis was performed using the unpaired, two-tailed independent sample Student's t-test, with 99% confidence intervals ($\mu$+/-2.58σ). A p value of <0.01 was considered to indicate significant differences in glucose carbon metabolism of immature and near-term, and different passage rat lung fibroblasts in response to 21% and 95% $O_2$ oxygen exposures.

Results

Figure 23:
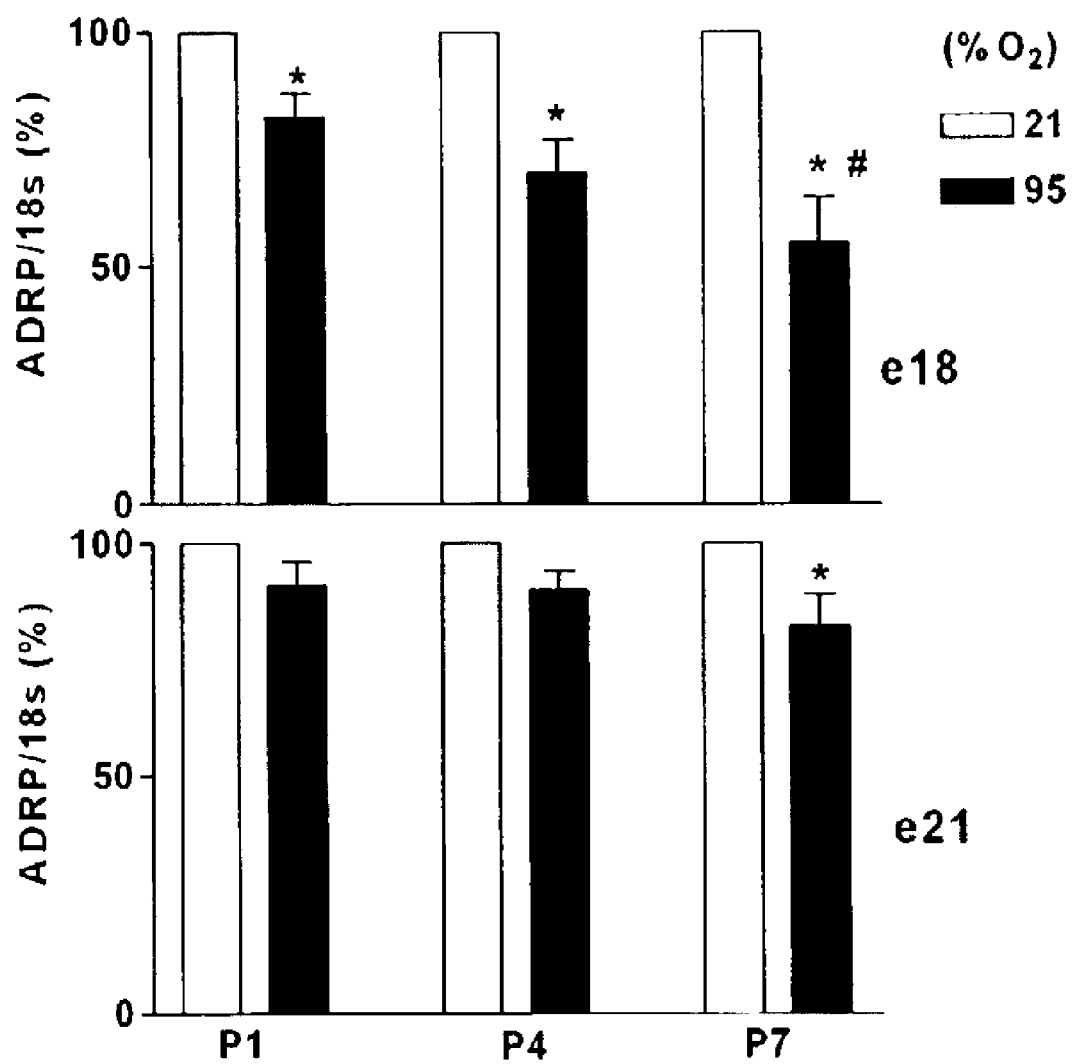
FIG. 23 shows that exposure to hyperoxia (95% $O_2$ for 24 h) at each passage (passage 1, 4, and 7) caused a decrease (*=$p<0.05$ vs. 21% $O_2$) in ADRP mRNA expression for the immature (e18) fibroblasts. This decease was more pronounced in P7 cells vs. P1 cells (#=$p<0.05$ vs. 21% $O_2$). In contrast, e21 fibroblasts were more resistant to the effects of hyperoxia. (Mean±SD; n=3)

Exposure to hyperoxia (95% $O_2$ for 24 h) at each passage (1, 4, and 7) caused decrease (*=p<0.05 vs. 21% $O_2$) in ADRP mRNA expression in the immature (e18) fibroblasts (FIG. 23). This decrease was most pronounced in P7 fibroblasts (#=p<0.05, P7 vs P1). In contrast, e21 fibroblasts were more resistant (reaching statistical significance only at P7) to the effects of hyperoxia than e18 fibroblasts. The decrease in ADRP mRNA expression, on exposure to hyperoxia, was accompanied by a concomitant increase in α-smooth muscle actin (SMA) mRNA expression (data not shown). This change was also most pronounced in e18 fibroblasts at P7.

Figure 24:
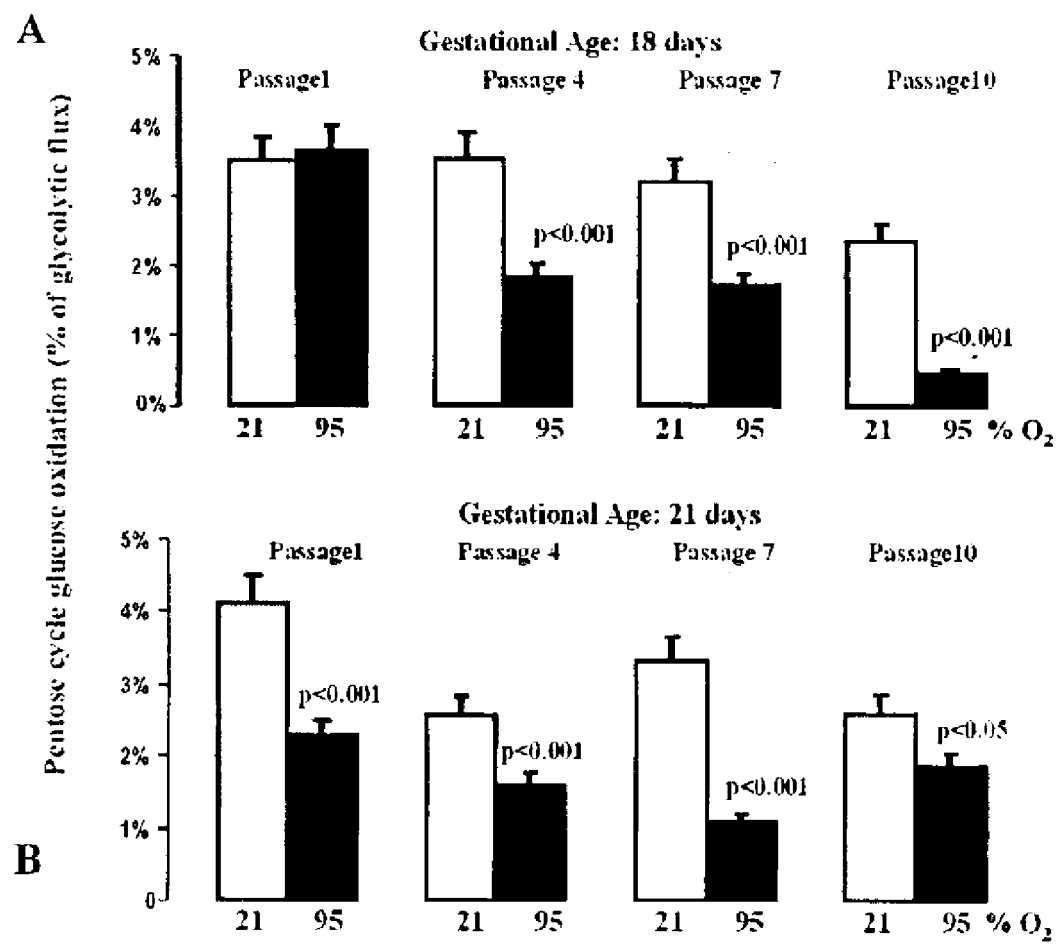
FIGS. 24A and 24B show a comparison of pentose cycle activity in e18 and e21 days rat lung fibroblasts in response to (21% (open bars) and 95% (black bars) oxygen tensions.

Accompanying the oxygen-induced decrease in ADRP, and the concomitant increase in α-SMA expression during the lipo-to-myofibroblast transdifferentiation, there were parallel changes in the pentose cycle metabolism affecting ribonucleic acid synthesis. FIG. 24 demonstrates direct glucose oxidation and recycling through the pentose cycle ($m_1$ lactate) relative to lactate production through the Embden-Meyerhoff-Parnas pathway ($m_2$). It is clear that between 2.5% and 3.5% of the glycolytic glucose flux undergoes direct oxidation by the pentose cycle in both near-term and immature fibroblasts in 21% oxygen. Upon hyperoxic exposure, direct glucose oxidation via the pentose cycle indicated significant, 62%, 58%, and 80.5% decreases after 4, 7 and 10 passages, respectively, in immature rat fibroblasts. Although mature fibroblasts also showed significant 54%, 46%, 72% and 28% decreases in pentose cycle activity after 1, 4, 7, and 10 passages, respectively, they demonstrated a less pronounced diminution in their pentose cycle glucose oxidation rates in response to hyperoxia after 10 passages than did the immature fibroblasts. These changes paralleled the increase in lipogenesis in these cells.

Figure 25:
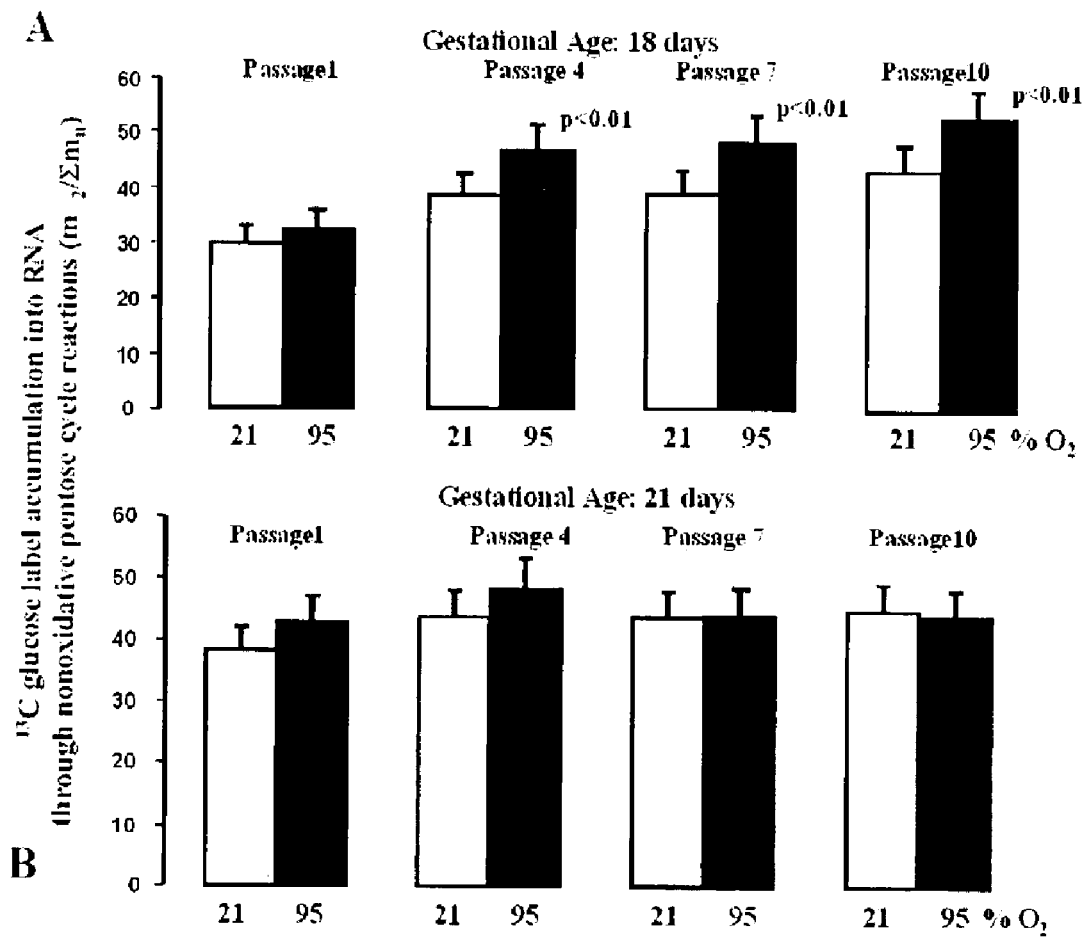
FIGS. 25A and 25B show the contribution of the nonoxidative steps of the pentose cycle to nucleic acid ribose synthesis (m2/$\Sigma m_n$) from glucose in e18 and e21 rat fetal lung fibroblasts in response to normal and high oxygen tensions.

In contrast, glucose carbon incorporation into RNA ribose was significantly increased through the non-oxidative reactions of the pentose cycle (FIG. 25). The data are expressed as the sum of $^{13}C$ incorporated through the nonoxidative steps of the pentose cycle ($m2/\Sigma m_n$) through transketolase and triose phosphate isomerase. Immature fibroblasts demonstrated a significant 9% to 19.8% increase in the accumulation of $^{13}C$ glucose-derived carbons in the ribose moiety of RNA in response to hyperoxic exposure. Near-term fibroblasts showed a less prominent, and progressively diminishing 7%, 8.7%, 0.7%, and 0.4% accumulation of $^{13}C$ glucose in RNA after 1, 4, 7 and 10 passages, respectively, through the nonoxidative reactions of the pentose cycle. Detailed mass isotopomer analysis of nucleic acid ribose indicated that the oxidative steps of the pentose cycle did not directly contribute to ribose synthesis in either the mature or near-term fibroblasts (data not shown).

Figure 26:
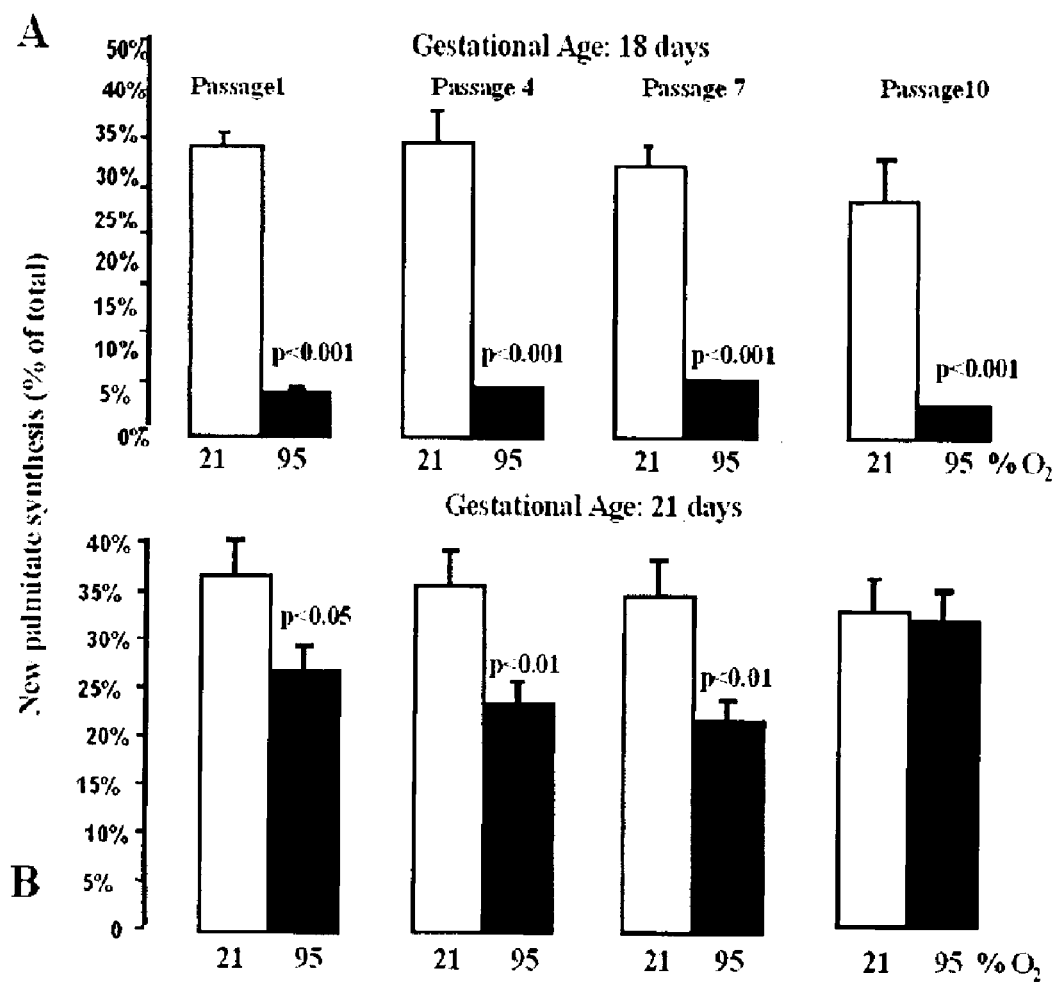
FIGS. 26A and 26B show a comparison of de novo palmitate synthesis from glucose in e18 and e21 day fetal rat lung fibroblasts in response to 21% (open bars) and 95% (black bars) oxygen tensions.

Stable glucose isotope labeling analysis of fetal rat lung fibroblast cultures exposed to hyperoxia, allowed us to characterize other oxygen-induced changes in metabolic activities by measuring carbon flux patterns. The de novo synthetic fraction of palmitate synthesis was between 30% and 35% of total palmitate in both immature and mature fibroblasts under normoxic conditions (FIG. 26). It was apparent from the mass isotopomer data that hyperoxic exposure decreased de novo palmitate synthesis by immature fibroblasts there was a >85% decrease in the rate of de novo palmitate synthesis in immature (e18) fibroblasts in response to hyperoxic exposure, at all passages, in comparison to normoxia-exposed cultures. Mature fibroblasts, on the other hand, showed a less prominent, 32% to 38% decrease in de novo palmitate synthesis on exposure to hyperoxia. However, at passage 10, even after exposure to hyperoxia, de novo palmitate synthesis was equal to control levels in these near-term (e21) fibroblasts.

Figure 27:
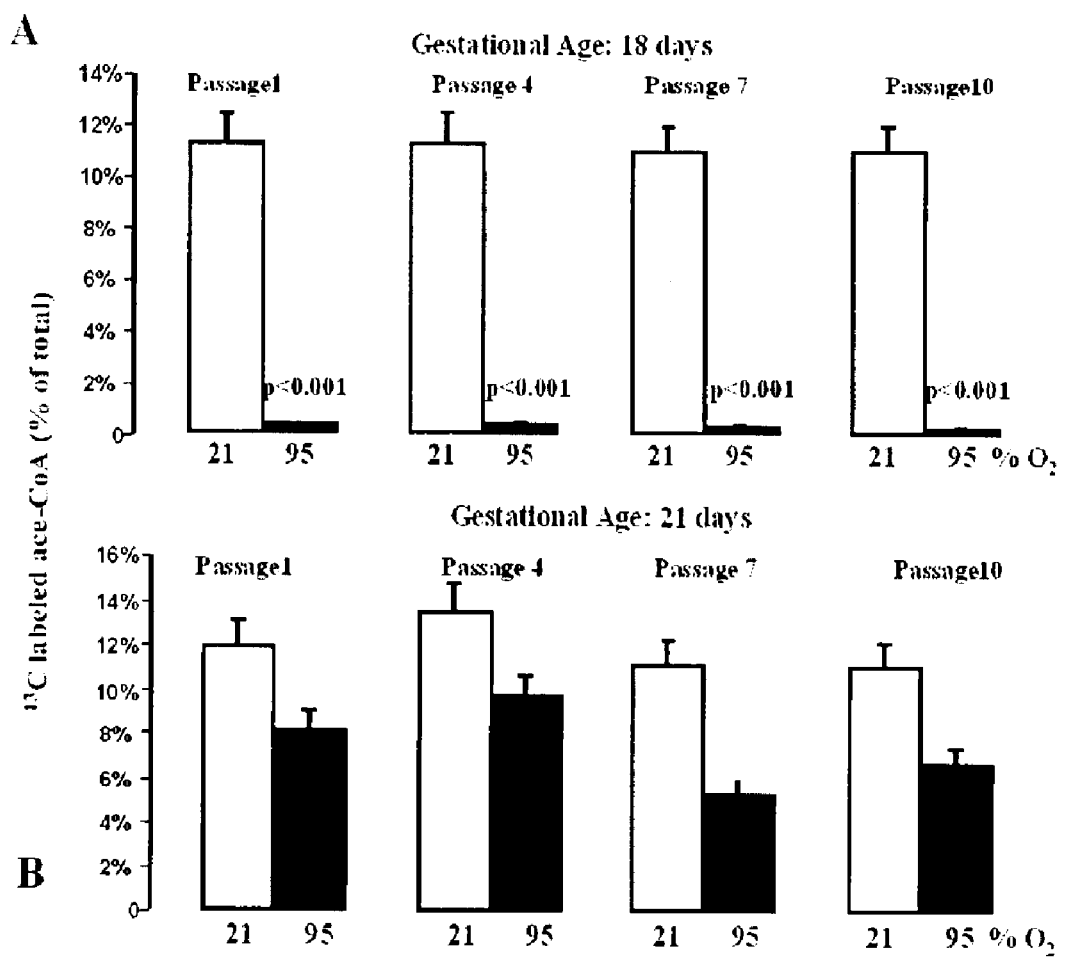
FIGS. 27A and 27B show a comparison of acetyl-CoA $^{13}C$ enrichment in e18 and e21 day rat lung fibroblasts in response to 21% (open bars) and 95% (black bars) oxygen tensions.

The $^{13}C$-glucose carbon labeling of the acetyl-CoA pool of immature and near-term fibroblasts varied between 11.2% and 12.7% under normoxic conditions (FIG. 27). $^{13}C$ labeling of acetyl-CoA in immature fibroblasts showed a dramatic 95% decrease after hyperoxic exposure, as it reached critically low values of 1% to 2% of that seen under control conditions. This indicates a severe imbalance in glucose carbon redistribution towards both the TCA cycle and de novo lipid synthesis in the immature fibroblasts exposed to hyperoxia. On the other hand, near-term fibroblasts showed a greater resistance to high oxygen treatment, as 5.8% to 9.8% of their acetyl-CoA pool was still labeled with $^{13}C$, indicating enhanced carbon flow between glycolysis, lipid synthesis, and the TCA cycle even under hyperoxic conditions.

Discussion:

Our data point to significant alterations in both molecular and metabolic characteristics of the immature and mature fetal rat lung fibroblasts when these cells are repeatedly passaged, exposed to hyperoxia, or both. Overall, there is a decrease in the lipofibroblastic and an increase in the myofibroblastic characteristics of these cells. Therefore, exposure to hyperoxia exacerbates the lipo-to-myofibroblast transdifferentiation, and this effect seems to be more pronounced in the immature, late-passage fibroblasts.

ADRP is localized on the surface of neutral lipid storage droplets, and is a recently identified marker for specialized adipogenic cells (Londos et al. (1999) Semin Cell Dev Biol., 10:51–58). Torday and coworkers have recently determined that ADRP plays an important role in lipid droplet metabolism and surfactant synthesis in the developing lung. As expected, we found that hyperoxia-induced transdifferentiation of lipo-to-myofibroblasts was accompanied by a significant decrease in the expression of ADRP mRNA. In related studies, we have also observed changes in the expression of other molecular markers characteristic of the lipogenic phenotype, such as the PPAR-γ and the PTHrP receptor, and increase in the expression of myogenic markers; particularly α-SMA (Rehan et al. (2001) Academy of Pediatric Societies, Baltimore, April).

Transdifferentiation is also associated with a gradual increase in the synthesis of nucleic acid ribose from glucose through the non-oxidative reactions of the pentose cycle, both with spontaneous passaging (from P1 to P10) and during hyperoxia-induced transdifferentiation of immature lipo-to-myofibroblasts (FIG. 27). This may explain the proliferative phenotypic changes observed in the interstitial fibroblast population of the oxygen damaged immature lung, and is consistent with metabolic changes expected of a proliferative phenotype. We have, previously, noted similar changes in proliferative-invasive transformation of H441 lung epithelial carcinoma cells induced by treatment with TGF-β (Boros et al. (2000) Cancer Res 60:1183–1185). Our data indicate that transdifferentiating immature fetal rat lung fibroblasts exhibit a proliferative metabolic phenotype by recruiting more glucose carbons for nucleic acid synthesis through the transketolase-controlled reactions of the pentose cycle. Increased non-oxidative nucleic acid ribose synthesis, accompanied by decreased direct glucose oxidation, reflects a significant metabolic change in fibroblasts in response to hyperoxia, inducing a more proliferative phenotype.

Oxygen exposure has important consequences for lipid metabolism in these cells other than the metabolic changes associated with transdifferentiation. The metabolic phenotype of cultured lipofibroblasts is characterized by high basal de novo lipogenesis, which derives most of its precursor from glucose carbons. There is a profound decrease in de novo lipid synthesis on exposure to hyperoxia, indicating that immature lipofibroblasts lose their ability to maintain their lipogenic phenotype. The loss of lipogenic potential limits the capacity of these lipofibroblasts to supply neutral lipids to type II pneumocytes for adequate surfactant phospholipid synthesis in the immature fetal lung (Torday et al. (1995) Biochim Biophys Acta. 1254:198–206). On the other hand, more mature fibroblasts demonstrate a relative metabolic resistance to hyperoxia, as they maintain sufficient direct glucose oxidation, and de novo lipid synthesis. Interestingly, the inhibition of lipogenesis is not passage dependent as are the molecular changes of transdifferentiation. Such a difference suggests that the suppression of lipogenesis and the increase in ribose synthesis from glucose may be two separate and distinct effects of hyperoxia. The relative resistance to hyperoxia exposure of lipid metabolic changes in the more mature fibroblasts is consistent with only a modest decrease in ADRP mRNA expression in these more matured cells. These fibroblasts continue to produce lipid-rich compounds, as evidenced by less diminution in the synthesis of palmitate from glucose, even in the face of hyperoxia. Concomitant with these changes in lipid metabolism, there is a gradual decrease in direct glucose oxidation through oxidative steps of the pentose cycle. These metabolic changes diminish the cell's ability to produce adequate amounts of reducing equivalents ($NADP^+$) for lipid synthesis and the regeneration of glutathione. This may explain our recent observation of reduced cytoprotection, against oxidant injury, afforded by fibroblasts with decreased cellular lipid reserves (~myofibroblasts) (Torday et al. (2001) Pediatr. Res. 49(6): 843–849).

These observations suggest, for the first time, that a number of metabolic pathways are primarily involved in hyperoxia induced injury to the premature lung. Hyperoxia induces lipo-to-myofibroblast transdifferentiation in the premature lung, and that pulmonary sensitivity to hyperoxic injury probably depends on the inability of immature fibroblasts to maintain their lipogenic phenotype.

Based on data reported herein, we speculate that there are two distinct glucose metabolic changes associated with oxygen-induced transdifferentiation of lung lipofibroblasts. Both changes in lipogenesis and in pentose cycle metabolism are dependent on the degree of immaturity of the lipofibroblasts. Hyperoxia rapidly induces a reduction in lipogenesis regardless of cell passage number. However, ribose synthesis from glucose and the reduction in glucose oxidation via the pentose cycle are, in addition, passage dependent, and occur gradually over several passages. The metabolic changes that reflect reductions in lipogenesis and direct glucose carbon trafficking toward nucleic acid synthesis likely have serious consequences not only for immature lipofibroblasts, but also for their neighboring type II pneumocytes in the developing lung, as the lipofibroblast phenotype is known to be critical for the growth, differentiation, and stability of the type II pneumocyte (McGowan and Torday (1997) Annu Rev Physiol. 59:43–62). Metabolic enzyme activities and their proportions in the immature lung, e.g., in bronchoalveolar lavage fluid, may serve as functional markers for monitoring the development of BPD, as a consequence of the hyperoxic lung injury. Furthermore, it follows that metabolic enzyme modulators may be utilized as a novel treatment modality for BPD.

Example 4

Parathyroid Hormone-Related Protein is a Gravisensor in Lung and Bone Cell Biology Parathyroid Hormone-related Protein (PTHrP) and its receptor represent a stretch sensitive paracrine signaling mechanism that may detect gravity. PTHrP has been shown to be essential for the development and homeostatic regulation of both lung and bone. Since lung and bone structure and function are affected by microgravity, we hypothesized that 0×g down-regulates PTHrP signaling. To test this hypothesis, we suspended lung and bone cells in the microgravity environment of a Rotating Wall Vessel Bioreactor, which simulates microgravity, for up to 72 hours. During the first 8 hours of exposure to 0×g, PTHrP expression fell precipitously, decreasing by 80–90%; during the subsequent 64 hours, PTHrP expression remained at this newly established level of expression. PTHrP production decreased from 12 pg/ml/hour to 1 pg/ml/hour in culture medium derived from microgravity-exposed cells. The cells were then re-cultured at unit gravity for 24 hours, and PTHrP expression and production returned to normal levels. Based on these findings, we requested bones from rats flown in space for 2 weeks (NASA Mission SL-2). Analysis of PTHrP expression by femurs and tibias from these animals (n=5) revealed that PTHrP expression was 60% lower than in bones from control ground-based rats. Importantly, there were no differences in PTHrP expression by parietal bones from space-exposed versus ground-based animals, indicating that the effect of weightlessness on PTHrP expression is due to the un-weighting of weight-bearing bones. This finding is consistent with other studies of microgravity-induced osteoporosis. The loss of the PTHrP signaling mechanism may be corrected using chemical agents that can up-regulate this pathway.

Introduction

Physical force is vitally important to the normal growth and function of a wide variety of tissues and organs, including muscle, bone, cardiovascular tissue and lungs (Vandenburgh (1992) Am. J. Physiol. 262: R350-R355). Lung development is well known to be influenced by a highly active mechanical environment (Alcorn et al. (1977) J. Anat. 123: 649–660; Moessinger et al. (1990) J. Clin. Invest. 86: 1270–1277). The differentiation of the alveolar epithelium, and the influence of the surrounding mesoderm are critical for preparing the newborn for extrauterine life (Torday (1992) Semin. Perinatol. 16: 130–139), and for repair (Shannon et al. (2001) Am. J. Respir. Cell Mol. Biol. 24: 235–244). The alveoli must be prepared for the transition from 3% to 21% oxygen, and for maintaining their patency by producing pulmonary surfactant (Frank et al. (1996) Biol. Neonate. 70: 116–127; Pinkerton et al. (2000) Biol. Neonate. 77: 243–252).

One possible interpretation of the link between physical force and development is that there are gravisensors that have allowed organisms to physiologically adapt to unit gravity during development (Wolgemuth and Murashov (1995) A.S.G.S.B. Bull. 8: 63–72). We have discovered that the establishment of the lung's cytoarchitecture is exquisitely sensitive to distensive forces within the fluid-filled womb, a process that would allow for the sensing of gravitational forces on the developing conceptus (Example 3, Sanchez-Esteban et al. (1998) Am. J. Med. Sci. 316: 200–204).

The identification of Parathyroid Hormone-related protein as a gravisensing mechanism (Rubin and Torday (2000) Pages 269–297 In: Endocrinology of the Lung. Humana Press, Totowa, N.J.; Torday and Rehan (2002) Am. J. Physiol. Lung Cell. Mol. Physiol. 283: L130–L135b) is an opportunity to determine the gravity sensing mechanism in the lung and other organs and tissues whose development and function are affected by PTHrP (Struckhoff and Turzynski (1995) Brain Res. 676: 1–9; Foley et al. (2001) Development. 128: 513–525; Clemens et al. (2001) Br. J. Pharmacol. 134: 1113–1136), of which there is a growing list.

The possibility that there is a link between adaptation to the gravitational environment and physiologic function is of great importance because if valid, it might change the prevailing attitude towards space-induced changes in bone and lung physiology from one of disease (Carmeliet et al. (2001) Crit. Rev. Eukaryot. Gene Expr. 11: 131–144) to one of adaptation.

Methods

Type II Cell Isolation and Culture

Time-mated Sprague-Dawley rats were obtained from Charles River Breeders, Hollister, Calif. Three to five dams were used per preparation. The dams were killed and the pups were excised and kept on ice. The lungs were removed en bloc in a laminar flow hood under sterile conditions and put into ice-cold sterile Hanks' balanced salt solution without calcium or magnesium. The solution was decanted and 5 volumes of 0.05% trypsin (Worthington) were added to the lung preparation. The lungs were dissociated in a 37° C. water bath using a Teflon™ stirring bar. When the tissue had been completely dispersed into a unicellular suspension the cells were spun down at 500×g for 10 min at room temperature in a 50 ml polystyrene centrifuge tube. The supernatant was discarded and the cell pellet was resuspended in Hepes buffer containing DNase (30:g/ml) without calcium.

The type II cells were isolated by Nycodenz gradient (Viscardi et al. (1992) *Exp. Lung Res.* 18: 225–245). At the termination of the lung dissociation the cell suspension was sequentially filtered through 2- and 4-ply gauze, then 37- and 15-:m nylon mesh, and washed. The cells were centrifuged at 130×g for 10 min at 20° C. and resuspended in DMEM with 2% fetal bovine serum for addition to Nycodenz gradients. Identity of fetal type II cells was documented by staining for the presence of glycogen and reaction with specific type II cell markers, Maclura pomifera lectin, and antibody to cytokeratins 8 and 18, and found to be more than 90% pure by these criteria.

Space Bones.

Bones from rats flown in space (NASA mission SLS-2) were provided courtesy of Dr. Paul Callahan, National Aeronautics and Space Administration, Ames Research Center, Moffett Field, Calif.

PTHrP ELISA:

PTHrP was determined using an enzyme-linked immunosorbent assay (courtesy of Dr. Delbert Fisher, Quest Diagnostics, San Juan Capistrano, Calif.).

RNA Isolation/Northern Hybridization:

Total cellular RNA was isolated using the method of Chomczynski et al. (1987) *Anal. Biochem.* 162: 156–159 with modification. Twenty microgram samples of RNA were denatured at 65° C. for 5 minutes and then fractionated by electrophoresis in 1.4% agarose/2.2M formaldehyde gels. The RNA was blotted, transferred to GeneScreen (NEN) nylon membranes in 10×SSC and immobilized by UV cross-linking. Antisense cRNA probes were synthesized from linearized recombinant phagemid templates using an in vitro transcription kit (Promega), the appropriate RNA polymerase and $^{32}$P-UTP (Amersham). The unincorporated nucleotides were separated from the RNA probes by affinity chromatography in Elutip columns (Schleicher & Schuell). Blots were hybridized to the probe for 18–22 hours at 65° C. and washed in 0.1×SSC/1% SDS at the same temperatures.

All blots were co-hybridized to a riboprobe synthesized to the constitutively expressed GAPDH. Blots were exposed to X-ray film with intensifying screens at −80° C. The intensity of mRNA bands of interest in each lane were normalized to the intensities of the corresponding GAPDH bands to control for variations in sample loading, RNA integrity and transfer efficiency among lanes. The resultant mRNA bands on the autoradiograms were quantified by image analysis.

Rotating Wall Vessel (RWV) Bioreactor

A rotating wall vessel (RWV) bioreactor (see, e.g., Schwarz et al. (1992) *J. Tissue Cult. Methods.* 14: 51–57), a NASA-approved apparatus, was operated based on the manufacturer's recommendations (Synthecon, Houston, Tex.). It is a horizontally rotated, bubble-free culture vessel with membrane diffusion gas exchange. The culture medium, cells and cell aggregate particles rotate with the vessel and do not collide with the vessel walls or any other damaging objects. Destructive shear forces are minimized because this system has no impellers, airlifts, bubbles or agitators. Cells establish a uniform, very low shear, fluid suspension orbit within the horizontally rotating culture vessel.

Cells of interest are attached to sterile collagen-coated Cytodex 3 microcarrier beads (Sigma, St. Louis, Mo.) in a humidified $CO_2$ incubator (5% $CO_2$, air balance, 37° C.) for 24 hours. At the initiation of the 0×g experiment, cells attached to the beads are put into the RWV bioreactor and rotated at 15 rpm in the $CO_2$ incubator. To control for 1×g conditions, some of the cells attached to beads are cultured in plastic culture dishes for the same period of time as those in the RWV bioreactor and are used as the control for any variation in gene activity due to culture, etc., at unit gravity. Cell-bead complexes can be sampled from the 1×g and 0×g conditions at various times to compare genes and gene products under these two conditions.

Competitive Reverse Transcribed-Polymerase Chain Reaction (RT-PCR)

First-strand cDNA is prepared using 10 μg total RNA and Moloney Murine Leukemia Virus reverse transcriptase (2 units, BRL, Gaithersburg, Md.), and random hexamers in a total volume of 10 μL of 50 mM Tris-HCL (pH 8.3), 75 mM KCl, 10 mM DTT, and 3 mM $MgCl_2$ for 60 min at 42° C. One μL of this reaction was used for each PCR reaction.

PCR reactions are carried out with HotTub thermostable DNA polymerase (Amersham). Briefly, 1 μL of the reverse-transcribed RNA mixture is added to 2.5 μL of 20× Reaction Buffer, 1.25 μL of 2 mM dATP, dGTP, dCTP and dTTP, 1 μL (1 unit) HotTub and 38.5 μL deionized water, each tube overlaid with 30 μL of mineral oil and subjected to 35 cycles of denaturation (0.5 min/93° C.), annealing (1.0 min/50° C.), and extension (1.5 min/72° C.) using a Programmable Thermal Cycler (Stratagene). The products of the reaction are analyzed on 4% agaraose gels and Southern blots are carried out by standard techniques, being probed with T4 kinase end-labelled probes using 30 bp primers corresponding to internal cDNA sequence of each gene analyzed and hybridized at 42° C. with the appropriate blot for 18 hours.

For semi-quantitative RT-PCR, conditions are determined such that the number of cycles yields approximately one-third maximal band intensity on Southern blots probed with a third internal oligonucleotide specific for the gene of interest. Thus, with a certain number of cycles for a given gene, we are within the linear range of detection. Furthermore, increased control positive RNAs (0.05–20 μL RT-PCR reaction product) are utilized to actually demonstrate a linear increase in RT-PCR signal for GAPDH and the gene of interest.

We have employed a commercially available primer and competimer™ for 18S ribosomal RNA (Ambion, Austin, Tex.) to control for PCR reaction and aliquot loading variability across samples.

GFP-PTHrP Construct

PCMV-GFP is made by removing GFP cDNA (Yu and Rasenick, 2002) and then ligating this DNA to the promoter for the PTHrP gene. Thus, GFP coding sequences are transcribed under the control of this specific distension-sensitive gene. Structural elements within the PTHrP promoter that are associated with distension have been identified by deletion analysis of a cloned portion of the promoter region of the gene. We have PCRed the 5' flanking region of the PTHrP gene from rat genomic DNA. This 1315 bp fragment corresponds to bp 831–2145 of Accession M24348 and is almost identical to bp 392–1691 of Accession X14304 and comprises all of the P3 region and approximately 800 bp of the P2 promoter region. This part of the promoter contains two putative transcription control elements, termed Shear Stress Response Elements (SSREs) at 484 and 539 bp 5' to the translation start site. This 1315 bp product has been cloned into plasmid TOPO-TA (Invitrogen) from which it was excised using the restriction enzyme EcoRI. Inserts into plasmid TOPO-TA are flanked by EcoRI restriction sites, and there are no such restriction sites within this portion of the PTHrP promoter. The intact 1315 bp insert now having EcoRI ends was ligated into the promoter-less reporter plasmid pEGFP-1 (Clontech). To determine whether the cloned portion of the PTHrP promoter was sufficient to drive gene expression by these transfected cells, we determined the amounts of GFP protein produced using Western analysis and GFP antibody (Clontech) to detect GFP protein in lysates from cells transfected with PTHrP promoter-pEGFP-1 constructs compared to lysates from cells transfected with promoterless pEGFP-1. In order to calibrate the effect of distension on the PTHrP-GFP fusion gene construct, we subjected the transfected cells to controlled distension using the Flexcell 3000 cell distension apparatus (Flexcell, McKeesport, Pa.). Resulting changes in GFP production were determined by Western analysis. When the cells transfected with this construct are exposed to microgravity, the amount of GFP produced changes commensurately.

Transfection

Prior to transfecting the cells, they were plated at 50–80% of confluence without antibiotics. The DNA preparation was complexed with Lipofectamine Plus reagent (GibcoBRL), added to the cell culture, and incubated for 3 hours at 37° C./5% $CO_2$. The cells were analyzed for the fusion construct within 24–48 hours after the start of the transfection.

Validation of the Transfection

To determine whether the cells had been successfully transfected, they were first examined by Laser Scanning Confocal microscopy (excitation maximum=488 nanometers; emission maximum=507 nanometers). We subsequently analyzed the cells for EGFP-N2 and PTHrP mRNAs by Northern Blot analysis and for their protein products by Western blot. The GFP-PTHrP complexes were immunoprecipitated using GFP monoclonal antibody #8362-1, which is specific for the EGFP protein. The blots were processed for the PTHrP-GFP complex, which co-migrated on the gel.

Statistics

All data were analyzed by Analysis of Variance. Differences were considered to be significant at the $p<0.05$ level.

Results

Figure 28:
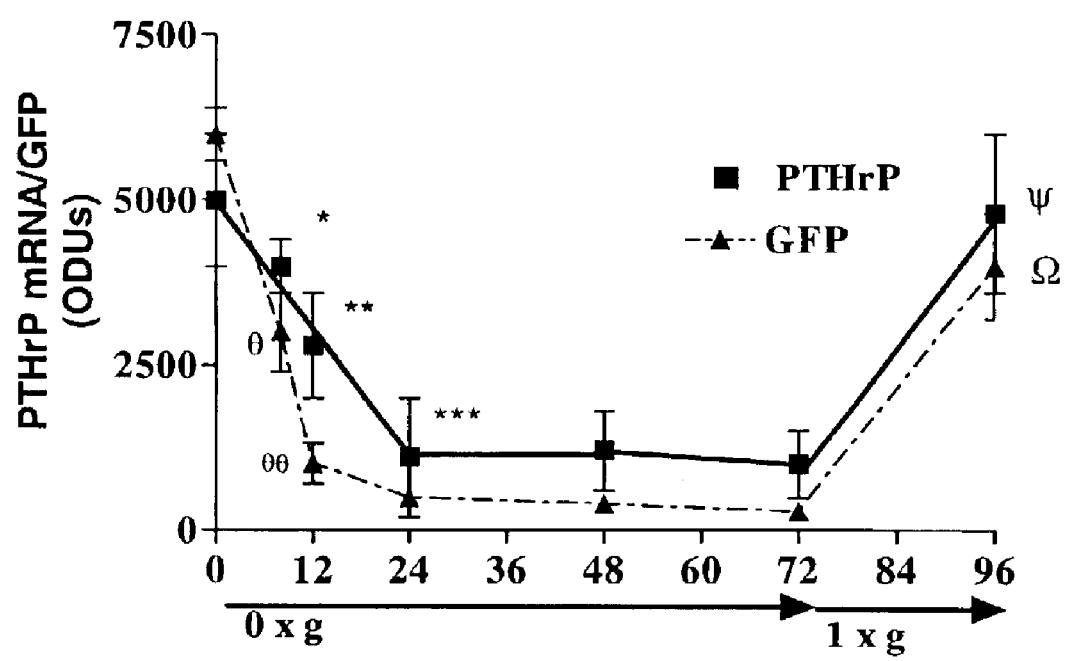
FIG. 28 shows PTHrP expression in fetal rat lung epithelial type II cells maintained in a rotating wall vessel for up to 72 hours. At the end of that time, the cells were put back in unit gravity for 24 hours. Cells were analyzed for PTHrP expression using both RT-PCR and GFP fluorescence n=6; *,$p<0.02$; ,$p<0.01$; *,$p<0.001$; P, $p<0.05$;2,$p<0.01$; 22,$p<0.001$; $\Sigma$, $p<0.05$ versus time-0 by analysis of variance.

Initially, fetal lung alveolar epithelial cells transfected with Green Fluorescent Protein inserted into the PTHrP promoter were attached to Sephadex beads and allowed to "free fall" in the NASA-approved RWV for up to 72 hours. As can be seen in FIG. 28, PTHrP expression, as determined by RT-PCR and normalized to GAPDH decreased precipitously within the first 8 hours, decreasing by 40% from the levels observed at unit gravity. There was a further decrease to 50% of 1×g expression levels at 12 hours, reaching a nadir at 80% of 1×g expression values after 24 hours' exposure to 0×g. This new baseline of PTHrP mRNA expression remained stable over the following 48 hours. The cells were then put back in culture at 1×g, and there was a return of PTHrP mRNA expression to the levels originally observed at 1×g. Similar results were obtained by monitoring for GFP fluorescence.

Figure 29:
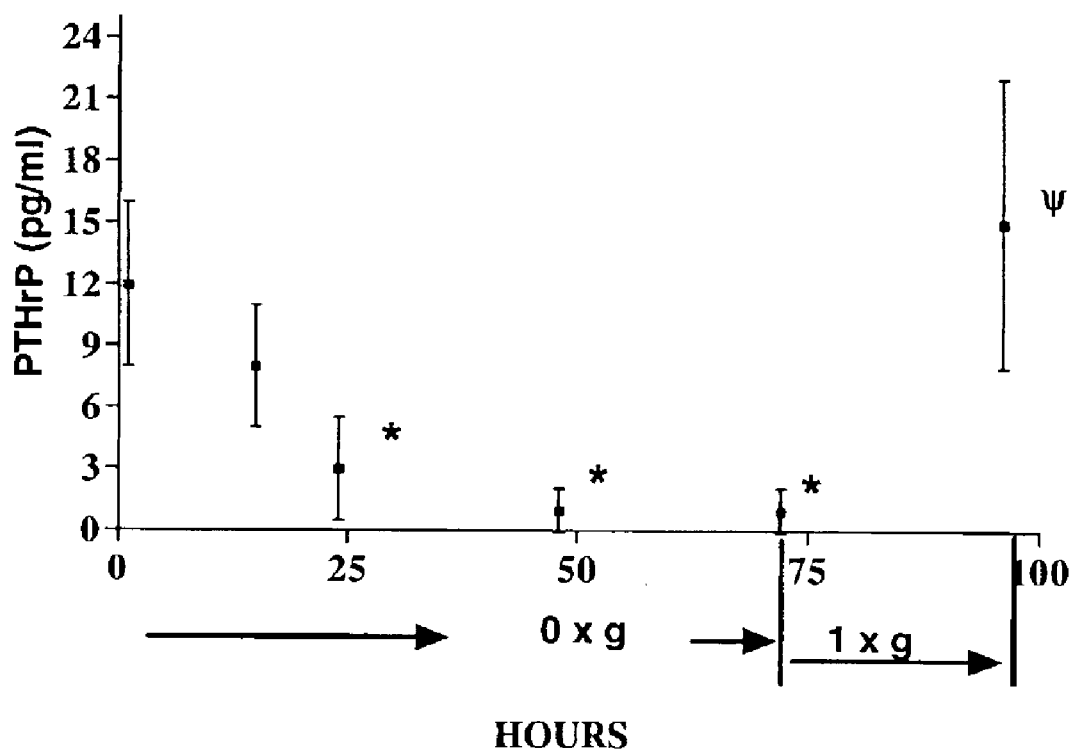
FIG. 29 illustrates PTHrP expression in fetal rat lung epithelial type II cells were maintained in a rotating wall vessel. Fetal rat lung epithelial type II cells were maintained in a rotating wall vessel for up to 72 hours. At the end of that time the cells were put back in unit gravity for 24 hours. Cells were analyzed for PTHrP expression. n=6; *,$p<0.01$; P,$p<0.05$ versus time=0 by Analysis of Variance.

As can be seen in FIG. 29, the production of PTHrP showed a decline similar to that for PTHrP mRNA expression. PTHrP production declined from 12∀4, to 8∀3, to 3∀2.5 pg/ml over the first 24 hours, and maintained the new baseline of production for the following 48 hours. Returning the cells to 1×g resulted in a return of PTHrP production to the pre-0×g levels.

Figure 30:
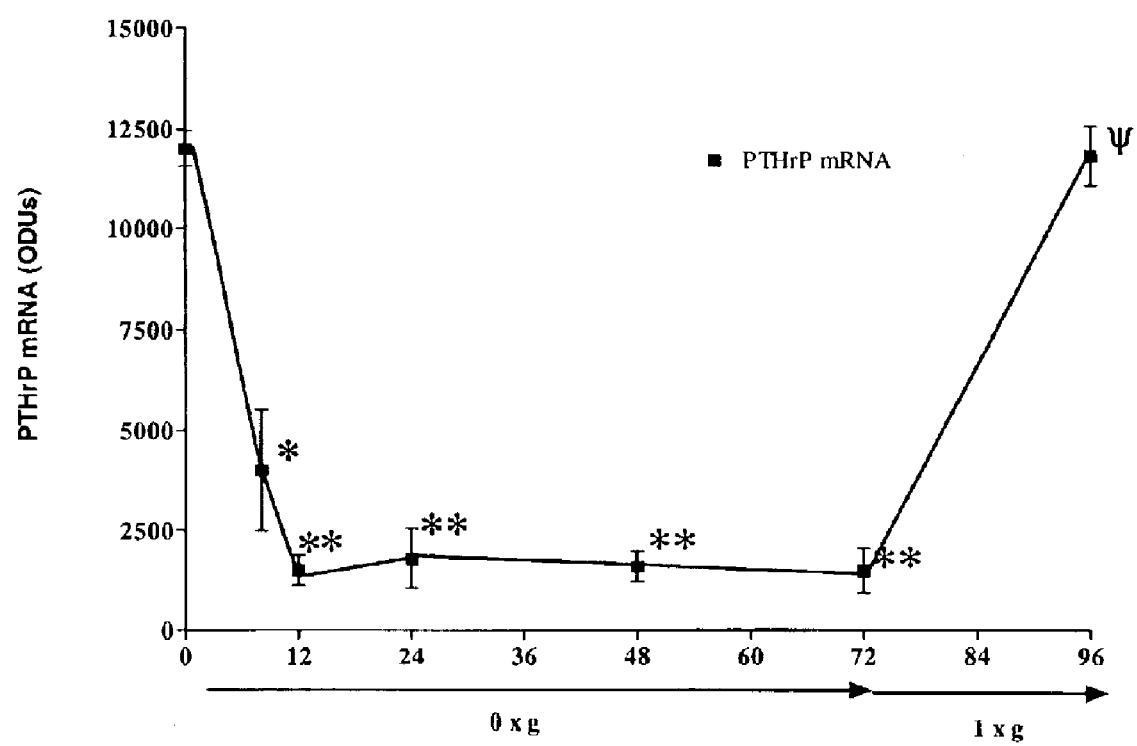
FIG. 30 illustrates RT-PCR analysis for PTHrP mRNA. Human UMR106 bone cells were maintained in a Rotating Wall Vessel for up to 72 hours. At the end of that time the cells were put back in unit gravity for 24 hours. Cells were analyzed for PTHrP mRNA by RT-PCR. n=6; *,$p<0.00001$; **,$p<0.000001$;P, $p>0.05$ versus time=0 by Analysis of Variance.

We subsequently tested the effect of 0×g on bone cells (FIG. 30). Human UMR106 osteoblasts were attached to Sephadex beads and placed in the Rotating Wall Vessel for up to 72 hours. There was a 64% decrease in PTHrP mRNA expression over the course of the first 8 hours of microgravity, followed by a further fall to about 10% of the 1×g levels, reaching a nadir by 12 hours' exposure. The mRNA levels remained at this new baseline for the remaining 60 hour exposure time. At the end of the microgravity exposure, the remaining cells were returned to 1×g. PTHrP mRNA expression returned to its pre-0×g levels within 24 hours.

Figure 31:
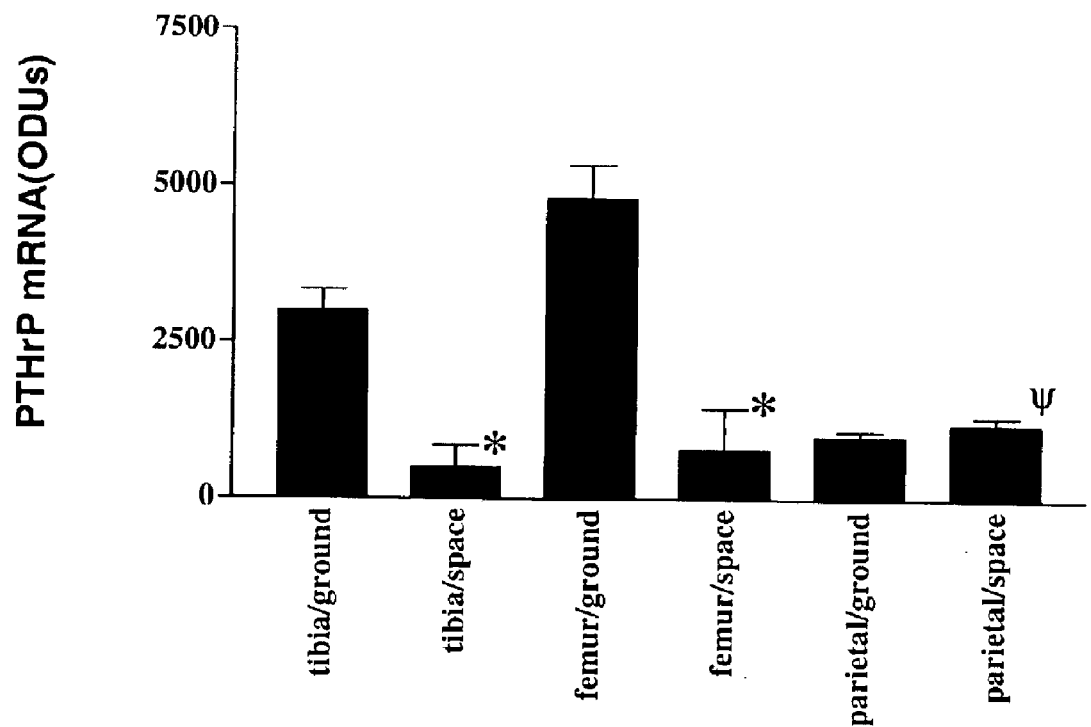
FIG. 31 illustrates PTHrP mRNA expression by bones from rats flown in space for 2 weeks were compared to ground-based rat bones. n=5; *, p<0.001; P, p<0.05 versus ground controls, by Student's t-test.

In order to determine whether the in vitro effects of the artificial gravity environment of the RWV reflected the effects of microgravity on PTHrP expression, we requested bones from rats that had flown in space by NASA. We determined PTHrP mRNA expression in femurs and tibias from "space-exposed" rats which had flown on the NASA SL-2 satellite to femurs and tibias from ground-based control rats. Parietal bones of the skull were analyzed as a control for the weight-bearing bones of the legs. We observed (FIG. 31) a dramatic 85 to 90% decrease in the amount of PTHrP mRNA in the femurs and tibias of the space-exposed rats. In contrast to this, there was no detectable effect of 0×g on PTHrP mRNA expression in the parietal bones, consistent with an effect on weight-bearing bones.

Discussion

In the present series of experiments, we have tested the hypothesis that microgravity down-regulates PTHrP expression. Consistent with this hypothesis, we observed a progressive decrease in PTHrP mRNA expression by lung epithelial cells, paralleled by a similar decrease in GFP fluorescence by the GFP gene inserted into the PTHrP promoter. There was a concomitant decrease in PTHrP production by these cells under the influence of microgravity, which was readily and completely restored simply by returning these cells to unit gravity.

Similarly, exposure of human UMR106 bone cells to microgravity decreased PTHrP mRNA expression by 90% over a 24-hour exposure; putting these cells back in 1×g returned PTHrP mRNA expression back to pre-0×g conditions. Based on these observations, we requested bones from rats flown in a NASA satellite for 2 weeks to test the hypothesized effects of microgravity on PTHrP expression in vivo. We observed a marked 85–90% decrease in PTHrP mRNA expression by cells removed from the bone shafts of the femurs and tibias. In contrast to this, we saw no effect of microgravity on PTHrP gene expression by the non-weight bearing bones of the skull, strongly suggesting that it is the weight-bearing bones whose PTHrP expression is up-regulated at 1×g, and is down-regulated in response to the un-weighting of these bones due to microgravity. The down-regulation of PTHrP expression due to microgravity may explain the bone decalcification and osteoporosis resulting from space travel, since PTHrP is a calciotropic hormone produced locally by bone cells.

There are two pathophysiologic consequences of human space travel-osteoporosis (Douglas et al. (1970) *Space Life Sci.* 2(2):151–157) and altered lung homeostasis (Venturoli et al. (1998) *Acta Astronaut.* 42: 185–204). These changes have been viewed as maladaptations or diseases up until now. We believe that, because we have evolved in adaptation to earth's gravitational environment, the physiologic changes that occur in response to 0×g constitute a resetting of physiologic homeostatic mechanisms in adaptation to changes in the physical environment. If this is the case, it would be dealt with differently than if it were considered an illness per se. By understanding the mechanisms that established the earth-oriented set point, we will be better able to cope with the resetting of the set point due to microgravity. And we may gain new insights into chronic illnesses that may be brought on by physical forces applied over the course of a lifetime.

The development of organs and tissues like lung and bone are initiated by the association of cells of different embryonic origins, followed by their paracrine interactions, leading to normal growth and differentiation of their cellular constituents (Zimmermann et al. (1988) *Cell Differ. Dev.* 25: 145–154;). Dispersed cells can reassemble themselves into histotypic structures that have many of the functional attributes of these same tissues in vivo (Zimmermann et al. (1988) *Cell Differ. Dev.* 25: 145–154; Engle et al. (1980) *Biochim Biophys Acta.* 617: 225–236;). For example, embryonic lung mesenchymal and epithelial cells will, under appropriate experimental conditions, reaggregate as organotypic lung tissue, comprised of epithelial cell spheres surrounded by mesenchyme, delimited by a basal lamina (Post et al. (1984) *Lung Res.* 7: 53–65; Torday et al. (1985) *Am. J. Physiol.* 249: C173–C176). These cell aggregates will actively secrete fluid into a central lumen, a process that appears necessary for subsequent in vitro cytodifferentiation of the mesenchymal and epithelial constituents, and results in the production of pulmonary surfactant by fully differentiated type II pneumonocytes. This kind of "self-organizing" system, characterized by small, incremental changes of a non-linear nature, contrasts to the large linear changes characteristic of "controlled" systems (Bak et al. (1995) *Proc. Natl. Acad. Sci. USA.* 92: 6689–6696). It is reasoned that in the same sense the mechanisms that lead to cellular homeostasis may, if molecularly disrupted, lead to disease in ways that have not previously been considered. This approach may provide novel approaches to both the physiologic problems created by space travel, and to many chronic fibrotic diseases that heretofore have remained idiopathic, and therefore untreatable (Kunkel et al. (1996) *Sarcoidosis Vasc. Diffuse Lung Dis.* 13: 120–128).

Example 5

Figure 32:
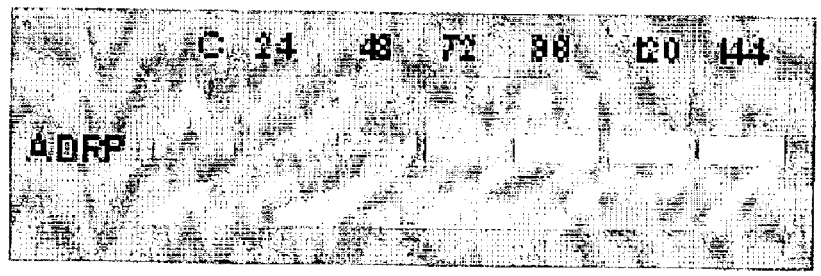
FIG. 32 illustrates the effect of rosiglitazone on Myofibroblast Re-expression of ADRP. Myofibroblasts were treated with rosiglitasone (1 μM) for up to 6 days, and screened for ADRP expression by RT-PCR.

Rosiglitazone Treatment Prevents Hyperoxia-Induced Neonatal Pulmonary Lipofibroblast-To-Myofibroblast Transdifferentiation In Vivo Recently, we have shown that in vitro exposure to hyperoxia accelerates transdifferentiation of pulmonary lipofibroblast to myofibroblast, and this could be a central molecular event in the pathogenesis of bronchopulmonary dysplasia. However, such a mechanism has not been demonstrated in vivo and strategies to prevent BPD remain largely unknown. Pulmonary lipofibroblasts are characterized by the expression of Peroxisomal Proliferator Activated Receptor (PPAR) gamma, Adipocyte Differentiation Related Protein (ADRP), Parathyroid Hormone related Protein Receptor (PTHrPR), while myofibroblasts characteristically express alpha smooth muscle actin (SMA); type II cells are characterized by expression of Cholinephosphate Cytidyltransferase (CP-CYT). Thus, we hypothesized that hyperoxic exposure of one day old neonatal rat pups would 1) decrease the expression of PPAR gamma, ADRP, PTHrPR, CP-CYT 2) increase the expression of alpha-SMA, and 3) treatment with PPAR gamma ligand, rosiglitazone, would attenuate the hyperoxia-induced effects. One-day-old rat (Sprague-dawley) pups were exposed for 24 h to either room air or hyperoxia (95% $O_2$+5% $CO_2$) and were administered either placebo or rosiglitazone at 1 or 3 mg/kg (intraperitoneally) at the beginning of the experimental period (n=4 for each group). After 24 h, rat pups were sacrificed and lung tissue analyzed for the expressions of PPARgamma, ADRP, PTHrPR, CP-CYT and (X-SMA mRNA (using RT-PCR) and protein (Western hybridization). We observed significant decreases in PPARgamma (−%), ADRP (−31%), PTHrPR (−17%), and CP-CYT (−49%) mRNA and corresponding protein expressions ($p<0.05$ vs normoxic controls for all), and a significant increase in alpha SMA (+40%) mRNA expression after 24 h exposure to hyperoxia (see FIG. 32). The decreases in PPARgamma, ADRP, PTHrPR, and CP-CYT expression and the increase in alpha SMA expression were partially (1 mg/kg) or completely (3 mg/kg) prevented by the simultaneous treatment with rosiglitazone at the beginning of the hyperoxic exposure. Our data provides the first evidence of in vivo lipo-to-myofibroblast transdifferentiation during hyperoxic exposure of neonatal rat pups and its complete prevention by the simultaneous administration of rosiglitazone. We believe treatment with PPAR gamma ligands is likely to be a key effective preventive and therapeutic strategy for bronchopulmonary dysplasia.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting lipofibroblast to myofibroblast transdifferentiation in a mammal, said method comprising:
administering to said mammal a PPAR gamma ligand in a concentration sufficient to partially or fully inhibit lipofibroblast to myofibroblast transdifferentiation in said mammal when said mammal is exposed to a hyperoxic condition.

2. The method of claim 1, wherein said PPAR gamma ligand is a thiozolidinedione (TZD).

3. The method of claim 1, wherein said PPAR gamma ligand is selected from the group consisting of rosiglitazone, troglitazone, farglitazar, phenylacetic acid, GW590735, GW677954, rosiglitazone maleate, rosiglitazone maleate+ metformin, ciglitazone, 15-deoxy-prostaglandin J2 (15PGJ2), 15-deoxy-delta-12,14-PGJ2, GW-9662, and MCC-555.

4. The method of claim 1, wherein said PPAR gamma ligand is rosiglitazone or an analogue thereof.

5. The method of claim 1, wherein said PPAR gamma ligand is administered in a concentration of at least 0.5 mg/kg.

6. The method of claim 1, wherein said PPAR gamma ligand is administered in a concentration of at least 1 mg/kg.

7. The method of claim 1, wherein said mammal is a non-human mammal.

8. The method of claim 1, wherein said mammal is a human.

9. The method of claim 1, wherein said mammal is a human having or at risk for bronchopulmonary dysplasia.

* * * * *

SEQUENCE LISTING

<160> NUMBER OF SEQ ID NOS: 23

<210> SEQ ID NO 1
<211> LENGTH: 33
<212> TYPE: PRT
<213> ORGANISM: Homo sapiens
<220> FEATURE:
<221> NAME/KEY: misc_feature
<222> LOCATION: (15)..(15)
<223> OTHER INFORMATION: Xaa is isoleucine
<220> FEATURE:
<221> NAME/KEY: misc_feature
<222> LOCATION: (28)..(28)
<223> OTHER INFORMATION: Xaa is isoleucine

```
<220> FEATURE:
<221> NAME/KEY: misc_feature
<222> LOCATION: (31)..(31)
<223> OTHER INFORMATION: Xaa is isoleucine

<400> SEQUENCE: 1

Ala Val Ser Glu His Gln Leu Leu His Asp Lys Gly Lys Ser Xaa Gln
1               5                   10                  15
Asp Leu Arg Arg Arg Phe Phe Leu His His Leu Xaa Ala Glu Xaa Thr
            20                  25                  30
Ala

<210> SEQ ID NO 2
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 2
tacacagtac ttctactaga tg                                          22

<210> SEQ ID NO 3
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 3
ccttgtggtc acttgtcgga ta                                          22

<210> SEQ ID NO 4
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 4
cctatctttt ctatgtccaa gc                                          22

<210> SEQ ID NO 5
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 5
gtcagatggt tgtctaggag tg                                          22

<210> SEQ ID NO 6
<211> LENGTH: 20
<212> TYPE: DNA
<213> ORGANISM: artificial
<220> FEATURE:
<223> OTHER INFORMATION: Synthetic nucleic acid primer.

<400> SEQUENCE: 6
tactttggaa gccctgatg                                              20

<210> SEQ ID NO 7
<211> LENGTH: 20
<212> TYPE: DNA
```

```
<213> ORGANISM: artificial
<220> FEATURE:
<223> OTHER INFORMATION: Synthetic nucleic acid primer.

<400> SEQUENCE: 7
gcacgtcagt gagtcacgaa                                              20

<210> SEQ ID NO 8
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 8
ttatgttcaa gcagtgccta tc                                           22

<210> SEQ ID NO 9
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 9
ctgtaagaag ttgtcaacct ac                                           22

<210> SEQ ID NO 10
<211> LENGTH: 20
<212> TYPE: DNA
<213> ORGANISM: artificial
<220> FEATURE:
<223> OTHER INFORMATION: Synthetic nucleic acid primer.

<400> SEQUENCE: 10
accttcagtt ccagattcga                                              20

<210> SEQ ID NO 11
<211> LENGTH: 20
<212> TYPE: DNA
<213> ORGANISM: artificial
<220> FEATURE:
<223> OTHER INFORMATION: Synthetic nucleic acid primer.

<400> SEQUENCE: 11 cccctttagtc tggttagagt                                             20

<210> SEQ ID NO 12
<211> LENGTH: 48
<212> TYPE: DNA
<213> ORGANISM: artificial
<220> FEATURE:
<223> OTHER INFORMATION: Synthetic nucleic acid primer.

<400> SEQUENCE: 12
gaacaaaggt cctcattatg gtcattcaca gctcacttat ggtcgtgc               48

<210> SEQ ID NO 13
<211> LENGTH: 48
<212> TYPE: DNA
<213> ORGANISM: artificial
<220> FEATURE:
<223> OTHER INFORMATION: Synthetic nucleic acid primer.

<400> SEQUENCE: 13
cttgtttcca ggagtaatac cagtaagtgt cgagtgaata ccagcacg               48
```

<210> SEQ ID NO 14
<211> LENGTH: 24
<212> TYPE: DNA
<213> ORGANISM: artificial
<220> FEATURE:
<223> OTHER INFORMATION: Synthetic nucleic acid primer.

<400> SEQUENCE: 14
ctcttcttga ctgttgtcgc tggt                                    24

<210> SEQ ID NO 15
<211> LENGTH: 21
<212> TYPE: DNA
<213> ORGANISM: artificial
<220> FEATURE:
<223> OTHER INFORMATION: Synthetic nucleic acid primer.

<400> SEQUENCE: 15
tggttgacca tgggtcctct t                                       21

<210> SEQ ID NO 16
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 16
tacacagtac ttctactaga tg                                      22

<210> SEQ ID NO 17
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 17
ccttgtggtc acttgtcgga ta                                      22

<210> SEQ ID NO 18
<211> LENGTH: 22
<212> TYPE: DNA
<213> ORGANISM: artificial
<220> FEATURE:
<223> OTHER INFORMATION: Synthetic nucleic acid primer.

<400> SEQUENCE: 18
atcgtggttg tggtggtagt cc                                      22

<210> SEQ ID NO 19
<211> LENGTH: 20
<212> TYPE: DNA
<213> ORGANISM: artificial
<220> FEATURE:
<223> OTHER INFORMATION: Synthetic nucleic acid primer.

<400> SEQUENCE: 19
ggctaagact aagaagaccc                                         20

<210> SEQ ID NO 20
<211> LENGTH: 48
<212> TYPE: DNA
<213> ORGANISM: artificial
<220> FEATURE:

```
<223> OTHER INFORMATION: Synthetic nucleic acid primer.

<400> SEQUENCE: 20
gaacaaaggt cctcattatg gtcattcaca gctcacttat ggtcgtgc        48

<210> SEQ ID NO 21
<211> LENGTH: 48
<212> TYPE: DNA
<213> ORGANISM: artificial
<220> FEATURE:
<223> OTHER INFORMATION: Synthetic nucleic acid primer.

<400> SEQUENCE: 21
gcacgaccat aagtgagctg tgaatgacca taatgaggac ctttgttc        48

<210> SEQ ID NO 22
<211> LENGTH: 21
<212> TYPE: DNA
<213> ORGANISM: artificial
<220> FEATURE:
<223> OTHER INFORMATION: Synthetic nucleic acid primer.

<400> SEQUENCE: 22
gagatggcca ctgctgcttc c                                     21

<210> SEQ ID NO 23
<211> LENGTH: 21
<212> TYPE: DNA
<213> ORGANISM: artificial
<220> FEATURE:
<223> OTHER INFORMATION: Synthetic nucleic acid primer.

<400> SEQUENCE: 23
gccgccgatc cagacagaat a                                     21
```